(12) United States Patent
Ahmed et al.

(10) Patent No.: US 9,821,157 B2
(45) Date of Patent: Nov. 21, 2017

(54) CHARGE-ENHANCED NEURAL ELECTRIC STIMULATION SYSTEM

(71) Applicants: Zaghloul Ahmed, Staten Island, NY (US); Andrzej Wieraszko, Princeton, NJ (US)

(72) Inventors: Zaghloul Ahmed, Staten Island, NY (US); Andrzej Wieraszko, Princeton, NJ (US)

(73) Assignee: The Research Foundation of the City University of New York, New York, NY (US)

( * ) Notice: Subject to any disclaimer, the term of this patent is extended or adjusted under 35 U.S.C. 154(b) by 330 days.

(21) Appl. No.: 14/157,689

(22) Filed: Jan. 17, 2014

(65) Prior Publication Data

US 2014/0135858 A1 May 15, 2014

Related U.S. Application Data

(63) Continuation of application No. 13/635,929, filed as application No. PCT/US2011/022283 on Jan. 24, (Continued)

(51) Int. Cl.
*A61N 1/36* (2006.01)
*A61N 1/20* (2006.01)
*A61N 1/05* (2006.01)

(52) U.S. Cl.
CPC .......... *A61N 1/205* (2013.01); *A61N 1/0551* (2013.01); *A61N 1/36003* (2013.01); (Continued)

(58) Field of Classification Search
CPC ............ A61N 1/36025; A61N 1/36103; A61N 1/36003; A61N 1/36067; A61N 1/36153; (Continued)

(56) References Cited

U.S. PATENT DOCUMENTS 4,813,399 A 3/1989 Gordon
4,926,864 A 5/1990 Dufresne et al.
(Continued)

FOREIGN PATENT DOCUMENTS

WO 2008106174 A1 9/2008
WO 2011050255 A2 4/2011
WO 2011119251 A2 9/2011

OTHER PUBLICATIONS

Office Action Issued in Japan Patent Office dated (Japanese original with English Translation).
(Continued)

*Primary Examiner* — William Levicky
*Assistant Examiner* — Minh Duc Pham
(74) *Attorney, Agent, or Firm* — Burns & Levinson LLP; Orlando Lopez

(57) ABSTRACT

A system and method to treat neural communication impairment is provided. The neural communication impairment is present in a neural pathway, which can be a cortico-neuro-muscular pathway, an intra-brain neural pathway, or in a sensory-cortico pathway. A synchronized external stimulation is applied to a first point in proximity to a first neural component at one end of the neural pathway and to a second point in proximity to a second neural component at the other end of the neural pathway. Two induced neural handshake signals contemporaneously arrive at a neural communication impairment point in the neural pathway, triggering and stimulating a rehabilitation process by which the neural connection is permanently improved. The synchronized applied electrical signals applied to the first and second points may have an opposite polarity in dipolar neural stimulation, or may have identical polarity and waveform in in-phase neural stimulation.

25 Claims, 48 Drawing Sheets

Related U.S. Application Data 2011, now abandoned, which is a continuation-in-part of application No. PCT/US2010/053720, filed on Oct. 22, 2010.

(60) Provisional application No. 61/316,319, filed on Mar. 22, 2010, provisional application No. 61/253,948, filed on Oct. 22, 2009.

(52) U.S. Cl.
CPC ..... *A61N 1/36067* (2013.01); *A61N 1/36071* (2013.01); *A61N 1/36082* (2013.01); *A61N 1/36096* (2013.01); *A61N 1/36103* (2013.01); *A61N 1/36153* (2013.01); *A61N 1/36171* (2013.01); *A61N 1/36175* (2013.01); *A61N 1/36157* (2013.01)

(58) Field of Classification Search
CPC ............ A61N 1/36157; A61N 1/36171; A61N 1/36175; A61N 1/36082; A61N 1/3787; A61B 5/4848; A61B 5/0476; A61B 5/055; A61B 5/7275; A61B 5/1038; A61B 5/1075; A61B 5/4082; A61B 5/4884
USPC .......................................................... 607/3
See application file for complete search history.

(56) References Cited

U.S. PATENT DOCUMENTS

| | | | |
|---|---|---|---|
| 4,926,865 | A | 5/1990 | Oman |
| 5,047,005 | A | 9/1991 | Cadwell |
| 5,100,373 | A | 3/1992 | Liboff et al. |
| 5,224,922 | A | 7/1993 | Kurtz |
| 5,450,859 | A | 9/1995 | Litovitz |
| 5,562,718 | A | 10/1996 | Palermo |
| 5,738,625 | A | 4/1998 | Gluck |
| 6,236,890 | B1 | 5/2001 | Oldham |
| 6,546,290 | B1 | 4/2003 | Shloznikov |
| 6,944,503 | B2 | 9/2005 | Crowe et al. |
| 7,160,241 | B1 | 1/2007 | Herbst |
| 7,254,445 | B2 | 8/2007 | Law et al. |
| 7,758,490 | B2 | 7/2010 | Pilla et al. |
| 2002/0161415 | A1 | 10/2002 | Cohen et al. |
| 2003/0171640 | A1 | 9/2003 | Canedo |
| 2003/0217754 | A1 | 11/2003 | Thomas et al. |
| 2004/0172097 | A1 | 9/2004 | Brodard et al. |
| 2006/0052657 | A9 | 3/2006 | Zabara |
| 2006/0116720 | A1 | 6/2006 | Knoblich |
| 2008/0208287 | A1 | 8/2008 | Palermo et al. |
| 2009/0204175 | A1 | 8/2009 | Zanella et al. |

OTHER PUBLICATIONS

Ahmed, Z. "Dipolar cortico-muscular electrical stimulation: a novel method that enhances motor function in both—normal and spinal cord injured mice", Journal of Neuroengineering and Rehabilitation, Biomed Central, London, GB, vol. 7, No. 1,Sep. 17, 2010 (Sep. 17, 2010), p. 46.

International Search Report of the International Searching Authority, International Application No. PCT/US2010/053720, filed on Oct. 22, 2010.

International Search Report of the International Searching Authority, International Application No. PCT/US2011/022283, filed on Jan. 24, 2011.

Laycock, D.C. Pulse Magnetic Field Therapy and the Physiotherapist, http://www.tgselectronics.com.au/physio.html, Jul. 1997.

Agrawal, S. K. et al. Mechanisms of secondary injury to spinal cord axons in vitro: role of Na+, Na(+)-K(+)-ATPase, the Na(+)-H+ exchanger, and the Na(+)-Ca2+ exchanger. J. of Neuroscience 16(2): 545-552, 1996.

Wieraszko, A. Dantrolene Modulates the Influence of Steady Magnetic Fields on Hippocampal Evoked Potentials in Vitro, Bioelectromagnetics 21:175-182 (2000).

Normal

Normal

SCI

Lesion Epicentre

Baseline

2 sec

Paired Stim.

44 sec

After

2 g 2 sec

Baseline 2 sec

Paired Stim.

44 sec

After 2 g 2 sec

To be rendered realistically

CHARGE-ENHANCED NEURAL ELECTRIC STIMULATION SYSTEM

CROSS-REFERENCE TO RELATED APPLICATIONS

This application is a continuation of co-pending U.S. patent application Ser. No. 13/635,929 which is a U.S national stage application under 35 U.S.C. 371 of International Application No. PCT/US11/22283 filed on Jan. 24, 2011 and entitled CHARGE-ENHANCED NEURAL ELECTRIC STIMULATION SYSTEM, which in turn claims the benefit of priority from U.S. Provisional Application No. 61/316,319, filed on Mar. 22, 2010 and which is also a continuation-in-part of PCT/US10/053720 filed on Oct. 22, 2010, which in turn claims the benefit of priority from U.S. Provisional Application No. 61/253, 948, filed on Oct. 22, 2009, the entire contents of which are incorporated herein by reference and for all purposes.

FIELD OF THE INVENTION

The present invention generally relates to the field of providing stimulation of central nervous system tissue, muscles, nerves, or combinations thereof, and more particularly to a system and method for improving neural or neuromuscular communication impairment through multi-point stimulation.

BACKGROUND OF THE INVENTION

The nervous system comprises the central and the peripheral nervous system. The central nervous system is composed of the brain and the spinal cord, and the peripheral nervous system consists of all of the other neural elements, namely the nerves and ganglia outside of the brain and spinal cord.

Damage to the nervous system may result from a traumatic injury, such as penetrating trauma or blunt trauma, or a disease or disorder including, but not limited to Alzheimer's disease, multiple sclerosis, Huntington's disease, amyotrophic lateral sclerosis (ALS), diabetic neuropathy, senile dementia, stroke and ischemia.

After spinal cord injury (SCI), spared regions of the central nervous system are spontaneously capable of repairing the damaged pathway, although the process is very limited. Moreover, despite the many promising treatment strategies to improve connections across the damaged spinal cord, the strength of connectivity and functional recovery of the impaired spinal cord are still unsatisfactory. It is well known that spared axons sprout after SCI. See Murray M., Goldberger M. E., Restitution of function and collateral sprouting in the cat spinal cord: the partially hemisected animal, J. Comp. Neurol., 158(1):19-36 (1974); Bareyre F. M., Kerschensteiner M., Raineteau O., Mettenleiter T. C., Weinmann O., Schwab M. E., The injured spinal cord spontaneously forms a new intraspinal circuit in adult rats, Nat. Neurosci. 7:269-77 (2004); Brus-Ramer M., Carmel J. B., Chakrabarty S., Martin J. H., Electrical stimulation of spared corticospinal axons augments connections with ipsilateral spinal motor circuits after injury, J, Neurosci. 27:13793-13901 (2007). But fine-tuning of the process of sprouting of spared axons after SCI as well as synapse stabilization might be dependent on precise pathway-selective activity.

Electrical stimulation of the central and peripheral nervous systems improves neuronal connectivity, and can be employed used to improve functional recovery after neuronal injury. It is an effective method that promotes reactive sprouting through which an increase in the number of functional connections may be possible. Electrical stimulation can also improve functional connections by strengthening the weak existing synapses and/or by promoting synaptogenesis. One of the emerging concepts is that the nervous system contains latent pathways that can be awoken by electrical stimulation or pharmacological manipulation.

The majority of the methods employing electrical stimulation utilize a one-point experimental paradigm in which unipolar or bipolar stimuli are delivered at one point of the sensorimotor pathway. The effectiveness of this stimulation depends on active propagation of an action potential through spared axons. Practically, one-point stimulation would be only effective if the neuronal connections exist and can support active and successful propagation of generated potentials. Therefore, one-point stimulation would be restricted in its efficacy and inclined toward stronger connections.

The loss of neuromuscular activity after SCI leads to inevitable abnormalities that limit the effectiveness of one-point stimulation by blocking excitatory responses from traveling across the sensorimotor pathway. Some of these abnormalities are muscle atrophy and peripheral nerve inexcitability. In addition, changes of the sensorimotor pathway below and above the lesion may involve several different mechanisms; some of them may be maladaptative. This maladaptive function will bias stimuli toward connections with better integrity, further limiting the effectiveness of localized stimulation.

According to the Habbian plasticity principle, physiological processes strengthen synaptic connections when presynaptic activity correlates with postsynaptic firing. See, for example, Hebb D, Organization of Behavior, New York, Wiley (1949). This phenomenon is known as long term potentiation ("LTP"). LTP could be induced by high-frequency presynaptic stimulation or by pairing low-frequency stimulation with postsynaptic depolarization. LTP can also be induced if a pre-synaptic input is activated concurrently with post-synaptic input. In addition, direct current passed through a neural pathway can modulate the excitability of that pathway depending on the current polarity and neuronal geometry. In that, anodal stimulation would excite while cathodal stimulation inhibits neuronal activity.

Thus, there is a great desire to improve the effectiveness of electrical stimulation when treating neural or neuromuscular communication.

SUMMARY OF THE INVENTION

The present invention provides method and apparatus in a system for stimulating effectiveness of communication between neuronally coupled sites in a vertebrate being. This is useful for treatment of neural and neuromotor issues for the infirm such as for reversal of a condition such as paralysis or for neural and muscular treatment and conditioning of healthy beings. The invention features charge-enhanced neural stimulation (CENS), wherein stimulation is applied in a manner that the natural communication process between neuronally coupled sites is invigorated. Preferred embodiments of the invention achieve lasting neuronal improvement, advantageously taking advantage of the Habbian plasticity principal and leveraging the phenomenon of long term potentiation ("LTP"). The pathway to be treated can be a cortico-neuromuscular pathway, an intra-brain neural pathway, or a sensory-cortico pathway. In implanted embodiments stimulation is applied subcutaneously, while in non-invasive embodiments it is applied externally, or combinations of the two.

There are two species of CENS: iCENS and aCENS. In both CENS cases, charge-enabled neural handshake signals meet on the neural pathway of interest and cause the natural restorative processes of the vertebral being to be invigorated with the result of improving communication between associated neural components of interest. In cases of injury or paralysis, such invigoration leads to improvement such as reversal of paralysis, in the case of healthy individuals such invigoration leads to improvement in neural performance and improvement in function.

In practice of the invention, neuronally coupled sites are neural components of a neural pathway. A unique combination of signals is applied to neuronally coupled sites and neural components thereof, e.g., at a brain location and at a muscle location. These applied stimulation signals generate neural handshake signals from each stimulated neural component. A charge signal is applied to the neural pathway, and the neural handshake signals converge on the neural pathway, such as at a neural communication trigger site, all contemporaneously. This charge-enhanced signal coupling or "handshake" associates the neuronally coupled sites with each other and strengthen the neural pathway of interest by stimulating the natural processes of neuronal growth and repair.

The charge signal may be inherently applied to the neural pathway as part of the stimulation signals or directly adjacent a trigger site, e.g., at a spinal trauma location or at a neuronal junction at the spine such as at a given vertebral location associated with a neural communication condition of interest, e.g., for achieving a desired action or for improving an impairment so as to increase communication intensity along the neural pathway of interest.

We have found that a vertebrate being with a level of capability in regard to achieving a particular outcome has a neural pathway trigger site associated with achieving the particular outcome, e.g., resolving paralysis. We have found that once the handshake signals couple in the charged environment of the invention, that communication between the neural components is greatly enhanced, with the level of applied charge signal being chosen wherein the neural handshake signals will interact and thus increase the neural responsiveness of the neural pathway. The increase in responsiveness is measurable as an improvement in the level of capability of the vertebrate being in regard to achieving the particular outcome, such as reducing paralysis. Once this handshake occurs, we have found that the natural neuronal processes of that vertebrate being are stimulated to enhance and improve such communication and thus improvement naturally continues after completion of the stimulation.

iCENS stands for inherent charge-enhanced neural stimulation mode of treatment. In an illustrative electronic embodiment of the invention, there is a single circuit established between two neural components in a neural pathway to be invigorated. A first stimulation signal is applied to a first of the neural components and generates a first neural handshake signal that propagates along the neural pathway and a second stimulation signal is applied to a second of the neural components and generates a second neural handshake signal that propagates along the neural pathway. A current flows in the neural pathway between the two neural components to provide a biased charge to the neural pathway. In one illustrative embodiment, with stimulation applied between a neural component associated with the motor cortex and a neural component associated with an extremity, the motor cortex is stimulated with a positive going signal and the extremity with a negative going signal as the source of the biased charge in the pathway.

In iCENS, the handshake signals are related but preferably inverted. The charge signal flows in the neural pathway simultaneously with the handshake signals. The charge-enabled neural handshake signals meet on the neural pathway stimulating neuronal growth and causing the natural restorative processes of neural generation to be invigorated with the result of improving communication between the associated neural components and achieving improved function.

aCENS stands for augmented charge-enhanced neural stimulation mode of treatment. In a preferred embodiment, at least three independent circuits provide three independent sources of signal, with at least one pair of stimulators (such as electrodes) from each of the three isolated sources applied to a neural pathway of interest. In one illustrative example of electrical treatment of lower body paralysis, a first pair of electrodes is placed on or about the motor cortex associated with the extremity of interest, defining a first neural component and stimulation of which creating a first neural handshake signal that propagates along the neural pathway. A second pair of electrodes is placed on or about the extremity of interest, defining a second neural component and stimulation of which creating a second neural handshake signal that also propagates along the neural pathway.

A third pair of electrodes is used to apply a charge signal from a third independent circuit, with a first electrode (preferably negative biased) placed on or about a neural communication trigger site associated with the neural pathway, such as at a spinal location notated by vertebral location. This trigger site may be a site of spinal injury or a location of a neural junction associated with a neural function of a distal neural component (such as associated with the abdomen or elsewhere on the body trunk). At least a second electrode (preferably positively biased) is applied distal from the trigger site such as adjacent to the distal neural competent. In this illustration, a lead is placed at such a vertebral location and a second lead or split leads are applied to the distal neural competent. An essentially negative charge signal thus applied between the electrodes at the trigger site and the distal neural component. The charge signal is applied to the neural pathway simultaneously with the flow of the neural handshake signals generated at the stimulated neural components, which invigorates the associated neural bundle within that neural pathway. Thus the natural neural restorative processes at that neural pathway are invigorated with the result of improving communication between the associated neural components adequately so as to repair infirmity, e.g., paralysis being. The neural handshake signals have identical or very similar characteristics. Stimulation may be applied subcutaneously or externally.

After a treatment session, neural communication continues in a form that is approximating or indeed is what would be normal for that vertebrate being. In such event, the natural communication process between such neuronally coupled components is further invigorated, with stimulation of neuronal growth occurring over time even without further stimulation although continued sessions are preferred.

These signals may be electronic, electromagnetic, sonic, or the like, but preferably the externally applied stimulation is electrical stimulation and is applied in the form of electrical signals. In some embodiments the external stimulation includes sonic stimulation, ultrasonic stimulation, magnetic stimulation (in which a steady state or dynamic magnetic field is applied), light stimulation, thermal stimulation (in which heat is applied), cryogenic stimulation (in which one or more neural element is subjected to exposure to a cold surface or a cold object), vibrational stimulation, pressure stimulation, vacuum stimulation, or any other sensory signal that may be applied in lieu of or in conjunction with external electrical stimulation.

In one embodiment, the applied stimulation can be electrical stimulation applied in the form of voltage signals. Alternately, the external stimulation may include any sonic stimulation, ultrasonic stimulation, magnetic stimulation (in which a steady state or dynamic magnetic field is applied), light stimulation, thermal stimulation (in which heat is applied), cryogenic stimulation (in which one or more neural element is subjected to exposure to a cold surface or a cold object), vibrational stimulation, pressure stimulation, vacuum stimulation, or any other sensory signal that may be applied in lieu of an applied electrical stimulation or in conjunction with an applied electrical stimulation.

If an applied stimulation is an electrical stimulation in the form of an externally applied voltage signal, such stimulation is applied across a pair of an active electrode and a corresponding reference electrode. The reference electrode provide a reference voltage level relative to which the signal applied to the corresponding active electrode is defined, and provides local electrical ground and a current return path for the electrical voltage applied through the corresponding active electrode.

In a first embodiment, first and second neural components can be a neuron in a motor cortex and a lower motoneuron at a muscle, respectively. For example, the first neural component can be a neuron in a motor cortex controlling the movement of the upper leg and the second neural component can be a femural nerve for treatment of paralysis related to the calf muscle. In this case, a charging signal, which is synchronous with the electrical signals applied to the motor cortex and the femural nerve, can be applied to the a point in the middle of the pathway such as a vertebrae in the spine. In a second embodiment, both the first and second neural components can be neurons in different cortexes that need to be in communication. For example, the first neural component can be a frontal lobe and the second neural component can be a parietal lobe for the treatment of an autistic spectrum disorder. The neural communication impairment point can be stimulated by application of two electrical signals to the two neural components without employing a charging signal. In a third embodiment, the first neural component can be a sensory nerve and the second neural component can be a sensory cortex.

Such external stimulation of paired neural components induces generation and transmission of respective neural handshake signals in the neural pathway. These handshake signals converge and meet at the neural communication impairment point, by means of which the neural components can reestablish communication. Depending on embodiment, this handshake can occur in presence of, or in the absence of, a charging signal. If a charging signal is employed as in the case of the aCENS method, charging the pathway amplifies the neural handshake signals and makes the handshake more likely to succeed. The charging signal enhances the coupling of the two induced neural handshake signals and invigorates communication between the stimulated first and second neural components. An active electrode is placed on a neural pathway trigger site located on the neural pathway under treatment. The charging signal is applied across the active electrode and a counterelectrode that is placed far away from the neural pathway. The charging signal is a constant negative direct current (DC) voltage relative to the counterelectrode.

In the iCENS mode, an active electrode is placed in proximity to one of the first and second neural components and a reference electrode is placed in proximity to the other of the first and second neural components. Because a neural pathway under treatment is present between the first and second neural components, the neural pathway is located between an active electrode and a reference electrode, and an external electrical signal is applied across the first neural component and the second neural component in the iCENS mode.

In the aCENS mode, a first stimulation signal is provided to a motor cortex in the form of a first electrical voltage signal across a first active electrode located at the first point and a first reference electrode located in the vicinity of the first point. The first point is located in proximity to a first neural element such as a mortor cortex. A second stimulation signal is provided to a second point in the form of a second electrical voltage signal across a second active electrode located at the second point and a second reference electrode located in the vicinity of the second point. The second point is located in proximity to a second neural element such as a motoneuron functionally related to a muscle. A charging signal is provided to a neural pathway trigger site located at a neural pathway between the first neural component and the second neural component. The charging signal is a constant voltage signal, and is preferably, a negative voltage signal. The treated neural pathway is thus located between a first active electrode to which the first electrical voltage signal is applied and a second active electrode to which the second electrical voltage signal is applied. The first and second electrical voltage signals can have the same waveform and polarity, and may be identical to each other.

Following removal of these signals, communication continues in a form that is approximating or in deed is what would be normal for that living being had there been no dysfunction. In such event, the natural communication process between such neuronally coupled components is invigorated, with stimulation of neuronal growth occurring over time. Preferably the stimulation and charging is done simultaneously. These signals may be electromagnetic or sonic or the like, but are preferably electronic.

In a preferred embodiment, a synchronized applied electrical stimulation signal is applied to a first point in proximity to a first neural component at one end of a neural pathway of interest and to a second point in proximity to a second neural component at the other end of the neural pathway of interest. Two induced neural signals are generated and arrive at a neural communication impairment point in the neural pathway, with the intent of triggering and stimulating a natural neural rehabilitation process by which the neural connection between such neural components is improved.

According to an aspect of the present invention, a method of improving neural communication impairment of a vertebrate being is provided. The method includes: placing a first electrode on a first point located in proximity to a first neural component of a vertebrate being; placing a second electrode on a second point located in proximity to a second neural component of the vertebrate being, wherein a neural communication impairment point exists in a neural pathway between the first neural component and the second neural component; and enhancing a neural connection between the first neural component and the second neural component by synchronously applying stimulation signals to the first point and to the second point.

In one embodiment, the first neural component is a motor cortex and the second neural component is a lower motoneuron. The lower motoneuron can be located in a limb of a vertebrate being and on the opposite side of the motor cortex relative to a spine of the vertebrate being. The method can further include: placing a third electrode on a muscle that the lower motoneuron controls; and applying an additional electrical stimulation signal to the third electrode, wherein the additional applied electrical stimulation signal is synchronous with the applied stimulation signals. The second point can be selected from an inner wrist, a fibular nerve ending, and a sole.

In another embodiment, the method can further include: placing at least another second electrode on at least another second point located in proximity to at least another second neural component, wherein a neural communication impairment point exists in another neural pathway between the first neural component and the other second neural component; and applying another stimulation signal that is synchronous with the applied stimulation signals to the at least another second electrode.

In even another embodiment, the vertebrate being is a human, and the neural communication impairment is selected from an injury suffered at a location in the spinal column, cerebral palsy, amyotrophic lateral sclerosis, traumatic brain injury, stroke, peripheral palsy, Erb's palsy, sciatica, and other peripheral nerve injuries due to nerve compression, tension, or torsion, and wherein the enhancing of the neural connection alleviates or reduces the one neural communication impairment.

In yet another embodiment, the first neural component is a first neuron in a first cortex of the vertebrate being and the second neural component is a second neuron in a second cortex of the vertebrate being. The neural communication impairment can be an autistic spectrum disorder or a disruption in neural communication between the right hemisphere of the brain of the vertebrate being and the left hemisphere of the brain of the vertebrate being.

In still another embodiment, the first neural component is a sensory neuron and the second neural component is a neuron in a sensory cortex. For example, the first neural component can include an optical nerve and the second neural component includes a neuron in a visual cortex. Alternately or additionally, the first neural component can include an auditory nerve and the second neural component includes a neuron in an auditory cortex.

In still yet another embodiment, the applied stimulation signals include a pair of synchronous electrical stimulation signals. Each of the pair of synchronous electrical stimulation signals can include electrical voltage pulses having synchronous rising edges and synchronous falling edges. A first applied electrical stimulation signal applied to the first point can have a first waveform as a function of time, and a second applied electrical stimulation signal applied to the second point can have a second waveform as a function of time, and the second waveform can be a scalar multiple of the first waveform. The first applied electrical stimulation signal and the second applied electrical stimulation signal can have the opposite polarities. Further, The first applied electrical stimulation signal and the second applied electrical stimulation signal are mirror image signals of each other.

In a further embodiment, a first stimulation signal applied to the first electrode and a second stimulation signal applied to the second electrode include simultaneous electrical pulses having opposite polarities, and an electrical current flows between the first point and the second point while the simultaneous electrical pulses are turned on. The first and second stimulation signals can be supplied by a pair of a positive output electrode and a negative output electrode of a signal generator, and the electrical current can flow through the signal generator.

In an even further embodiment, the first electrode is a first active electrode and the second electrode is a second active electrode, and the method further includes: placing a first reference electrode in the vicinity of the first active electrode on the vertebrate being; and placing a second reference electrode in the vicinity of the second active electrode on the vertebrate being, wherein the first reference electrode is the most proximate to the first active electrode among all electrodes on the vertebrate being and the second reference electrode is the most proximate to the second active electrode among all electrodes on the vertebrate being, wherein a first stimulation signal is applied across the first active electrode and the first reference electrode and a second stimulation signal is applied across the second active electrode and the second reference electrode.

In a yet further embodiment, the first and a second stimulation signals have the same polarity. The first and a second stimulation signals can be identical in waveform, phase, and polarity.

In a still further embodiment, the first and second stimulation signals are supplied by two synchronized signal generators, and a first electrical current flows across the first point and a point contacting the first reference electrode and through one of the two synchronized signal generators, and a second electrical current flows across the second point and a point contacting the second reference electrode and through the other of the two synchronized signal generators.

In a still yet further embodiment, the method further includes: placing a third electrode at a third point located on the neural pathway between the first neural component and the second neural component; and applying a charging signal having a constant direct current (DC) voltage to the third electrode.

In further another embodiment, the charging signal is a negative voltage that remains constant throughout application of the stimulation signals.

In even further another embodiment, the pair of synchronous electrical stimulation signals includes a first applied electrical stimulation signal that is applied to the first point and having a first waveform as a function of time and a second applied electrical stimulation signal that is applied to the second point and having a second waveform as a function of time, and first and second waveforms are scalar multiples of each another. The pair of synchronous electrical stimulation signals can have the same polarity. The pair of synchronous electrical stimulation signals can include signals that are identical in waveform, phase, and polarity.

In yet further another embodiment, the third point is the neural communications impairment point. The neural communication impairment can be a spinal injury, and the third point can be a spinal vertebra at which the spinal injury is present.

Alternately, the third point may not be the neural communication impairment point, but is a location known to be associated with the neural communication impairment. The third point may be a site of a neural branch within the communication pathway. The third point may be a location where spinal cord neurons branch out to innervate the upper extremities or branch out to innervate the lower extremities.

In still further another embodiment, the method includes determining an optimal signal magnitude for the applied stimulation signals, wherein the applied stimulation signals are applied at the optimal signal magnitude. The optimal signal magnitude can be determined by gradually increasing a magnitude of test signals applied to the first and second points, wherein the optimal signal magnitude is set at a signal magnitude at which a muscle associated with the first or second neural element begins to react to the test signals.

The applied stimulation signals includes pulses can be repeated at least 20 times and at most 100,000 times. The application of the stimulation signals can be repeated multiple times with at least two days of interval between consecutive sessions. The applied stimulation signals can be applied at magnitudes that induce a first neural handshake signal in the first neural element and induce a second neural handshake signal in the second neural element. The first neural handshake signal in the first neural element and the second neural handshake signal converge at the neural communication impairment point with a temporal overlap to provide a handshake at the neural communication impairment point.

The method can further include: placing a third electrode at a third point located on the neural pathway between the first neural component and the second neural component; and applying a charging signal having a constant direct current (DC) voltage to the third electrode.

In still yet further another embodiment, each of the applied stimulation signals are selected from an electrical voltage signal, a sonic stimulation signal, an ultrasonic stimulation signal, a magnetic stimulation signal in which a steady state or dynamic magnetic field is applied, a light stimulation signal, a thermal stimulation signal, a cryogenic stimulation signal, a vibrational stimulation signal, a pressure stimulation signal, a vacuum suction stimulation signal, and any other sensory signal that the vertebrate being is capable of sensing. At least one of the applied stimulation signals can be provided by an implanted device that is temporarily or permanently implanted in the vertebrate being or a portable device that is carried by the vertebrate being.

The applied stimulation signals can include periodic pulses of identical waveform. The applied stimulation signal can have a frequency that does not exceed 100 Hz, and the periodic pulses can have a duration from 40 microseconds to 10 milliseconds. The method can further include: placing a third electrode at a third point located on the neural pathway between the first neural component and the second neural component; and applying a charging signal having a constant direct current (DC) voltage to the third electrode.

According to another aspect of the present invention, a system for improving neural responsiveness of a neural pathway of a vertebrate being is provided. The system includes: a first means for inducing a first neural handshake signal, the first means configured to supply a first applied stimulation signal to a first neural component of a neural pathway of interest, the first applied stimulation signal including a first set of signal pulses having a magnitude that induces the first neural component to issue the first neural handshake signal on the neural pathway; a second means for inducing a second neural handshake signal, the second means configured to supply a second applied stimulation signal to a second neural component of the neural pathway of interest, the second applied stimulation signal including a second set of signal pulses having a magnitude that induces the second neural component to issue the second neural handshake signal on the neural pathway contemporaneously with the first neural handshake signal, the neural pathway having a base charge potential prior to application of the first and second applied stimulation signals; and a charging signal source for applying a charging signal to a neural pathway trigger site while the first and second neural handshake signals are present in the neural pathway, wherein the first and second neural handshake signals interact and increase neural responsiveness of the neural pathway, the increase in neural responsiveness being measurable as an improvement in a level of capability of the vertebrate being in regard to achieving an outcome that depends on a functional level of the neural pathway.

In one embodiment, the charging signal source is configured to apply a constant negative voltage to the neural pathway trigger site.

In another embodiment, the system further includes a signal characteristics selector for selecting characteristics of the first and second applied stimulation signals and the charging signal.

In yet another embodiment, the signal type selector includes an input device for identifying at least one of a type of the neural pathway of interest and a type of the outcome, wherein the input device adjusts first and second applied stimulation signals and the charging signal according to an input to the input device and selected from predetermined menu of signal characteristics.

In still another embodiment, at least one of the first means and the second means is configured to supply periodic pulses at a frequency that does not exceed 100 Hz, the periodic pulses having a duration from 40 microseconds to 10 milliseconds.

In a further embodiment, the periodic pulses have a magnitude from 1 V to 35 V and the at least one of the first means and the second means is capable of supplying a current from 1 mA to 35 mA while the periodic pulses are on.

In an even further embodiment, the system is configured to apply a series of the periodic pulses, wherein a total number of the periodic pulses is from 20 to 100,000.

In a yet further embodiment, the system is configured such that a first waveform of the first applied stimulation signal as a function of time and a second waveform of the second applied stimulation signal as a function of time are scalar multiples of each another.

In a still further embodiment, the first and second waveforms are identical in characteristics, magnitude, and polarity.

According to even another aspect of the present invention, a system for improving neural responsiveness of a neural pathway of a vertebrate being is provided. The system includes: a first means for inducing a first neural handshake signal, the first means configured to supply a first applied stimulation signal to a first neural component of a neural pathway of interest, the first applied stimulation signal including a first set of signal pulses having a magnitude that induces the first neural component to issue the first neural handshake signal on the neural pathway; and a second means for inducing a second neural handshake signal, the second means configured to supply a second applied stimulation signal to a second neural component of the neural pathway of interest, the second applied stimulation signal including a second set of signal pulses having a magnitude that induces the second neural component to issue the second neural handshake signal on the neural pathway contemporaneously with the first neural handshake signal, the neural pathway having a base charge potential prior to application of the first and second applied stimulation signals, wherein at least one of the first means and the second means is an implanted device that is temporarily or permanently implanted in the vertebrate being or a portable device that is carried by the vertebrate being.

In one embodiment, both of the first means and the second means are implanted or portable devices that are temporarily or permanently implanted in the vertebrate being or carried by the vertebrate being.

In another embodiment, the system further includes a charging signal source for applying a charging signal to a neural pathway trigger site while the first and second neural handshake signals are present in the neural pathway, wherein the first and second neural handshake signals interact and increase neural responsiveness of the neural pathway, the increase in neural responsiveness being measurable as an improvement in a level of capability of the vertebrate being in regard to achieving an outcome that depends on a functional level of the neural pathway, wherein the charging signal source is another implanted device that is temporarily or permanently implanted in the vertebrate being or carried by the vertebrate being.

According yet another aspect of the present invention, a system for improving neural communication impairment of a vertebrate being is provided. The system includes: a first signal generating means configured to generate a first stimulation signal having a first set of pulsed signals and having the characteristic of inducing first pulsed neural signals; a first signal transmission means configured to apply the first stimulation signal to a first point in proximity to a first neural component of a vertebrate being; a second signal generating means configured to generate a second stimulation signal having a second set of pulsed signals that is synchronized with the first set of pulsed signals and having the characteristic of inducing a second pulsed neural signal synchronously with the first pulsed neural signals; a second signal transmission means configured to apply the second stimulation signal to a second point in proximity to a second neural component of a vertebrate being, wherein the second neural component is located at an end of a neural pathway extending to the first neural component; and a signal monitoring means configured to detect a handshake of the first periodic neural signals and the second periodic neural signals at a point in the neural pathway. For example, an oscilloscope or any other signal capturing electronic device can be wired to enable detection of a voltage signal or a current signal at the point in the neural pathway, which can be a neural pathway trigger site.

In one embodiment, at least one of the first and second signal generating means is configured to generate electrical pulses.

In another embodiment, the first and second signal generating means are configured to maintain the first set of pulsed signals and the second set of pulsed signals to have synchronous rising edges and synchronous falling edges.

In even another embodiment, the first set of pulsed signals and the second set of pulsed signals are periodic electrical signals.

In yet another embodiment, the first set of pulsed signals has a first waveform and the second set of pulsed signals has a second waveform that is a scalar multiple of the first waveform.

In still another embodiment, the first and second signal generating means are embodied in a single signal generator having a positive output electrode and a negative output electrode, wherein one of the positive and negative output electrodes supplies the first stimulation signal and the other of the positive and negative output electrodes supplies the second stimulation signal.

In still yet another embodiment, the system further includes: yet another electrode configured to be placed at a third point located on the neural pathway between the first neural component and the second neural component; and a charging signal generating means configured to generate a charging signal having a constant direct current (DC) voltage to the third electrode.

In a further embodiment, the yet another electrode is configured to be placed on a spinal vertebra.

In an even further embodiment, the yet another electrode is configured to be placed on a location where spinal cord neurons branch out to innervate the upper extremities or branch out to innervate the lower extremities.

In a yet further embodiment, the system includes a computer configured to synchronize application of the first and second stimulation signals.

In a still further embodiment, the computer includes a program for determining an optimal signal magnitude by gradually increasing a magnitude of at least one test signal applied to the first and second points, wherein the optimal signal magnitude is set at a signal magnitude at which a muscle associated with the first or second neural element begins to react to the at least one test signal.

In a still yet further embodiment, the computer is configured to provide the first and second applied stimulation signals as signal pulses repeated at least 20 times and at most 100,000 times.

In further another embodiment, the first and second stimulation signal are selected from an electrical voltage signal, a sonic stimulation signal, an ultrasonic stimulation signal, a magnetic stimulation signal in which a steady state or dynamic magnetic field is applied, a light stimulation signal, a thermal stimulation signal, a cryogenic stimulation signal, a vibrational stimulation signal, a pressure stimulation signal, a vacuum suction stimulation signal, and any other sensory signal capable of sensed by a vertebrate being.

In even further another embodiment, one of the first and second stimulation signal is an electrical voltage signal, and the other of the first and second stimulation signal is selected from a sonic stimulation signal, an ultrasonic stimulation signal, a magnetic stimulation signal in which a steady state or dynamic magnetic field is applied, a light stimulation signal, a thermal stimulation signal, a cryogenic stimulation signal, a vibrational stimulation signal, a pressure stimulation signal, a vacuum suction stimulation signal, and any other sensory signal capable of sensed by a vertebrate being.

In yet further another embodiment, the first and second stimulation signals have a frequency that does not exceed 100 Hz, and the periodic pulses have a duration from 40 microseconds to 10 milliseconds.

In still further another embodiment, one of the first and second signal transmission means is configured to apply a stimulation signal to a cortex of a vertebrate being and the other of the first and second signal transmission means is configured to apply another stimulation signal to a location in a limb of the vertebrate.

In still yet further another embodiment, the other of the first and second signal transmission means is configured to apply the other stimulation signal to a location selected from an inner wrist, a fibular nerve ending, and a sole of a human being.

Further, the first signal transmission means can be configured to apply a stimulation signal to a first cortex of a vertebrate being and the second signal transmission means can be configured to apply another stimulation signal to another cortex of the vertebrate being.

In addition, one of the first and second signal transmission means can be configured to apply a stimulation signal to a cortex of a vertebrate being and the other of the first and second signal transmission means can be configured to apply another stimulation signal to a sensory neuron of the vertebrate being.

The system can further include a signal characteristics selector for selecting characteristics of the first and second stimulation signals. The signal type selector can include an input device for identifying at least one of a type of the neural pathway of interest and a type of the outcome, wherein the input device adjusts first and second applied stimulation signals according to an input to the input device and selected from predetermined menu of signal characteristics.

BRIEF DESCRIPTION OF THE DRAWINGS

FIGS. 14 A and 14B are examples of spontaneous activity recorded before (baseline), during, and after a-tsDC (A) or c-tsDC (B) are shown.

In FIG. 14C, the firing frequency during a-tsDC showed a significant effect of condition (F=135.40, p<0.001, repeated measures ANOVA). Post hoc tests revealed a higher firing frequency during a-tsDC steps +1, +2, and +3 mA.

In FIG. 14D, firing frequency during c-tsDC also showed a significant effect of condition (F=338.00, p<0.001, repeated measures ANOVA). Post hoc testing revealed a significant difference during c-tsDC steps −2, and −3 mA.

In FIG. 14E, spike amplitude during a-tsDC showed a significant effect of condition (H=738.14 p=0.001, Kruskal-Wallis ANOVA). Post hoc tests revealed a higher spike amplitude during a-tsDC +2 and +3 mA.

In FIG. 14F, spike amplitude during c-tsDC also showed an effect of condition (H=262.40, p≤0.001, Kruskal-Wallis ANOVA). Post hoc tests revealed a higher spike amplitude during c-tsDC. Error bars represent S.E.M. *p<0.05 relative to baseline.

In FIG. 5A, autocorrelogram of a-tsDC-induced activity shows no oscillation or bursting. In FIG. 5B, autocorrelogram of c-tsDC-induced activity shows strong bursts by 10 ms and oscillations. In FIG. 5C, oscillatory activity was also induced by injecting the glycine and GABA receptor blockers picrotoxin and strychnine into the spinal cord at L3-L4.

In FIG. 16A, examples of TS twitches evoked before (baseline), during, and immediately after a-tsDC are shown. Note that a-tsDC depressed the ability of the motor cortex to elicit TS twitches during stimulation, but facilitated twitches after stimulation. In FIG. 16B, however, c-tsDC improved the ability of the motor cortex to elicit TS twitches during stimulation, but not afterwards. For each animal (n=5/group), the average of ten TS twitches was analyzed before stimulation (baseline), during the five intensity steps, and after stimulation (0, 5, and 20 min) with a-tsDC as illustrated in FIG. 16C or c-tsDC as illustrated in FIG. 16D.

In FIG. 17A, latencies of tibial nerve potentials, measured from the stimulus artifact (SA) to the first deflection of the potential, were prolonged during a-tsDC and shortened after a-tsDC. Dashed vertical lines mark the points of measurement. Note the difference in the scale bars. In FIG. 17B, latencies of cortically-elicited tibial nerve potentials were shortened during c-tsDC and prolonged afterwards. FIG. 17C illustrate that, for a-tsDC, there was a significant effect of condition (H=30.10, p<0.001, Kruskal-Wallis ANOVA). Post hocs revealed a significantly longer latency during +2 mA and a shorter latency afterwards. FIG. 17D illustrate that, for c-tsDC, there was also a significant effect of condition (H=29.84, p<0.001, Kruskal-Wallis ANOVA). Post hocs revealed a significantly shorter latency during −2 mA and a longer latency afterwards. Error bars represent S.E.M. *p<0.05 relative to baseline.

DETAILED DESCRIPTION OF THE INVENTION

Figure 1A:
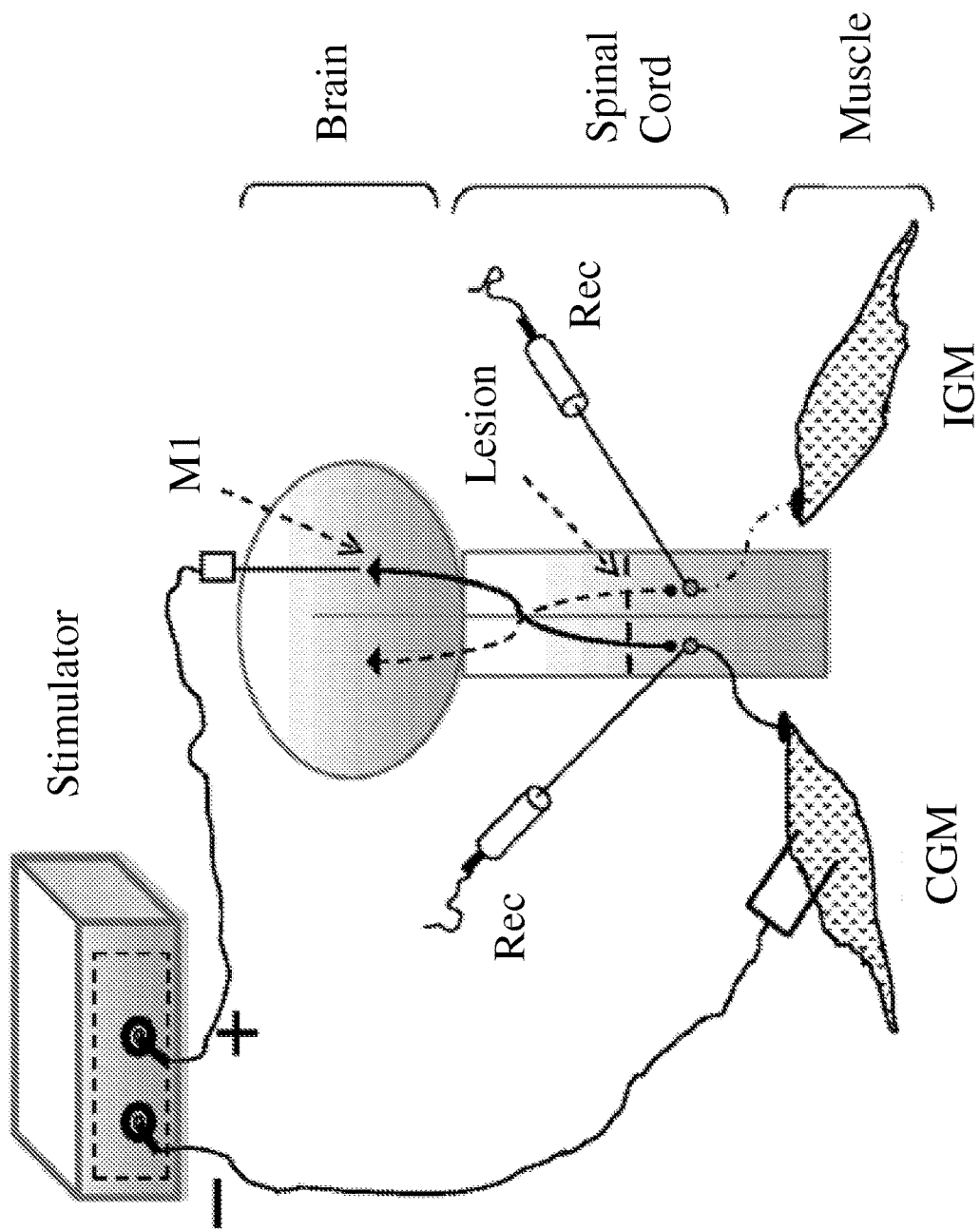
FIG. 1A is an illustration of the basic configuration and setup for utilizing dipole cortico-muscular stimulation (dCMS).

As stated above, the present invention relates to a system and method for treating neuromuscular conditions through applied stimulation, which are now described in detail with accompanying figures. It is also noted that drawings are not necessarily drawn to scale.

As used herein, "neural communication" includes any communication in a nerve or a set of nerves, which may include communication with and without impairment.

As used herein, "neural communication impairment" or an "impairment" includes any weakness, partial or total disruption, degradation, or failure of neural communication in a nerve or a set of nerves, due to biological/genetic causes and/or external/mechanical causes, and includes ab initio neural communication impairment, genetic post-birth neural communication impairment, trauma-induced neural communication impairment, and various dysfunction(s) associated therewith.

As used herein, "ab initio failure of neural communication" refers to neural communication impairment triggered before birth by genetic defects.

As used herein, "genetic post-birth neural communication impairment" refers to neural communication impairment triggered after birth by genetic defects.

As used herein, "trauma-induced neural communication impairment" refers to neural communication impairment triggered by trauma, before or after birth, that weakens, disrupts, degrades, or causes partially or fully to fail, any nerve or set of nerves.

As used herein, a "vertebrate being" refers to any biological animal that has a spinal column, and includes humans and all animals classified under subphyla *Vertebrata*.

As used herein, a "limb" is a leg, an arm, a wing, a flipper, a side of a fin, or any anatomical equivalent thereof of a vertebrate being.

As used herein, a "central nervous system" is the set of a brain and a spinal column of a vertebrate being.

As used herein, a "neural component" is any cell structure that is capable of neural communication, and includes an axon of a neuron, a dendrite of a neuron, or any other natural or artificial biological component capable of generating or receiving neurotransmitters.

As used herein, a first element is placed "in proximity to" a second element if a stimulus applied to the first element induces a non-zero electrical signal a neural component of the second element.

As used herein, a "point" or a "site" refers to a tissue site or a general region of tissue location of an animal or a human.

As used herein, a "neural communication impairment point" or an "impairment point" refers to a tissue site of an animal or a human at which the condition of neural communication impairment is physiologically embodied or manifested as weakened physical condition, partial or total disrupted structure, physical degradation, or the presence or absence of a physical structure that otherwise manifests and embodies the condition of neural communications impairment. or a tissue site that functions as a proxy for neural communication impairment.

As used herein, a "neural pathway" or a "pathway" includes any connecting neural intact or impaired communication linkage between a neural component and another neural component or a part thereof, and may include one or a plurality of neurons connected to respective neural components.

As used herein, a "neural handshake signal" or a "handshake signal" is one of a pair of induced neural signals that propagate toward and contemporaneously converge at a common point in a neural pathway.

As used herein, a "neural communication trigger site" is a location associated with a neural pathway and which is associated with neural communication with a neural component of interest. A neural communications trigger site is a location at which neural handshake signals may interact in the presence of a charge signal in the neural pathway of interest, and may also be a neural communication impairment point.

As used herein, a first induced neural signal and a second induced neural signal that arrive at the same neural communication impairment point are "contemporaneous" if any portion of the waveform in the first induced neural signal overlaps in time with any portion of the waveform in the second induced neural signal.

As used herein, a "handshake" refers to a contemporaneous convergence of a pair of neural signals at a point in a neural pathway.

As used herein, "neural communication rehabilitation" or "rehabilitation" refers to the process of partial or full removal of any weakness, partial or total disruption, degradation, or failure of neural communication in a nerve or a set of nerves employing applied stimulation that causes induced neural signals that arrive at a neural communication impairment point.

As used herein, a "neural communication rehabilitation point" or a "rehabilitation point" refers to a tissue site that was at one point a neural communication impairment point at one point in time, but at which the process of neural communication rehabilitation occurs so that any weakness, partial or total disruption, degradation, or failure of neural communication is partially of fully removed.

As used herein, an element is "configured to" perform an act if the element is shaped, and includes all necessarily intrinsic features, to enable performance of the act as a natural consequence of having the shape and the necessary feature.

As used herein, an "active electrode" is an electrode to which an electrical pulse is applied either as at least one positive voltage pulse or at least one negative voltage pulse. Therefore, an active electrode can be a positive electrode or a negative electrode depending on the polarity of the applied electrical pulse.

As used herein, a "reference electrode" is an electrode that provides a reference voltage to a vertebrate being while an active electrode applies an electrical pulse. A reference electrode may be held at a constant electrostatic potential. For alternating current (AC) signal applications, a reference electrode functions as electrical ground while a corresponding active electrode applies a time-dependent electrical signal.

As used herein, a "counterelectrode" is an electrode that provide a reference voltage for direct current (DC) applications, i.e., in applications in which a corresponding active electrode applies a constant voltage relative to the counterelectrode.

As used herein, a "polarizing current" refers to a direct current electrical current that flows and through a neuron between a first electrode and a second electrode and causes polarization of electrical charges in the neuron.

As used herein, a "lower motoneuron" or a "lower motor neuron" is a motor neuron connecting the spinal column to a muscle fiber(s) and including an axon that terminates at the muscle fiber(s).

As used herein, a first signal and a second signal are "synchronous" or "synchronized" if the rising edges of the first and second signals coincide in time and/or the falling edges of the first and second signals coincide in time. Each of the first and second signals can be an electrical voltage signal, a sonic stimulation signal, an ultrasonic stimulation signal, a magnetic stimulation signal in which a steady state or dynamic magnetic field is applied, a light stimulation signal, a thermal stimulation signal, a cryogenic stimulation signal, a vibrational stimulation signal, a pressure stimulation signal, a vacuum suction stimulation signal, or any other sensory signal that a vertebrate being is capable of sensing.

As used herein, a device is "implanted" is the device is placed in or on a vertebrate being and is self-powered, i.e., powered by a power source such as a battery.

As used herein, a device is "implantable" if the device is configured to enable implantation in or on a vertebrate being.

As used herein, a device is "portable" is the device can be affixed to the body or clothing or an accessory of a vertebrate being and is self-powered.

Embodiments of the present invention disclose methods and systems for treating neural communication impairment in a nerve or a set of nerves. Also, healthy individuals will benefit from practice of the present invention although they are without apparent neural impairment, such as for athletic purposes.

Certainly, those with neural impairment do benefit from the present invention. Neural neural communications impairment may be ab initio neural communication impairment, genetic post-birth neural communication impairment, trauma-induced neural communication impairment, or a combination of thereof. For purposes of this disclosure, it will be appreciated that the embodiments of the invention illustrated below are directed to improvement and repair of neural impairment however such principals and procedures may be applied to healthy individuals for their own neural improvement interests with equal validity.

In broad terms, a neural pathway to be improved is identified. In the example of a neural impairment, this may be referred to as a neural pathway or a dysfunctional neural pathway or the like. Two neural components in the neural pathway to be stimulated are identified. External stimulation is applied to simultaneously generate two neural handshake signals at the two neural components, which propagate along the pathway to the neural communication impairment point in the neural pathway in the presence of a charging signal. The handshake of the two neural handshake signals in the charged environment at the neural communication impairment initiates and facilitates a natural biological rehabilitation process.

The present invention provides applied stimulation at a neural communication impairment point at which the condition of neural communication impairment is physiologically embodied. The neural communication impairment point may be a region including weakened, disrupted, degraded, or failed nerve structure or a region in which a nerve connection is absent where that nerve connection is supposed to be present for a normally functioning nerve or neuromuscular system.

Prior to the application of the external stimulation, a first neural element functionally connected to a first neural component and a second neural element functionally connected to a second neural component are present at the neural communication impairment point without a fully functional neural connection therebetween. The first neural component may be a neuron in one part of the brain, and second neural component may be a neuron in a muscle or a neuron in a different part of the brain. The lack of the fully function neural connection, whether in the form of a degraded neural connection or the absence of a neural connection, is a characteristic of the neural communication impairment point. In other words, the first neural element and the second neural element are either weakly linked or not linked for the purposes of neural communication therebetween. The first neural component may be one end of an axon, and the second neural component may be an end of another axon. Alternately, the first neural component may be a first portion of an axon, and the second neural component may be a second portion of the same axon, provided that the neural communication between the first portion and the second portion is impaired for any reason.

The first neural component is located in a first body part, and the second neural component is located in a second body part that is different from the first body part. In a normally functioning vertebrate being, a functional communication pathway exists between the first body part and the second body part. A neural signal is generated by the first neural component, is transmitted through the functional communication pathway, and arrives at the second neural component with sufficient signal strength so that the second neural component can trigger additional activities in other neurons or muscles that are functionally related to the second neural component. When neural communication impairment is present in the neural communication pathway, neural communication is possible but attenuated such that a neural signal cannot be transmitted from the first neural component to the second neural component with sufficient strength, and therefore, the second neural component does not trigger any additional activity in a vertebrate being.

In a first embodiment, the first neutral component is a neuron located in a cortex and the second neural component is a lower motoneuron functionally related to the neuron in the cortex, i.e., the lower motoneuron is designed to actuate a muscle controlled by the neuron in the cortex in a normally functioning vertebrate being. A cortico-neuromuscular pathway for transmission of a neural signal exists between the first neural component and the second neural component in a normally functioning vertebrate being. In many cases, the cortico-neuromuscular pathway may run through a spinal cord. The neural communication impairment occurs in the cortico-neuromuscular pathway in this case. Thus, the neural communication impairment point may be present in the spinal cord or within the portion of the cortico-neuromuscular pathway located in one of the limbs of the vertebrate being.

In a second embodiment, the first neural component is a first neuron located in a first portion of a cortex and the second neural component is a second neuron located in a second portion of the same cortex or in a portion of a different cortex. For example, it has been recently known that individuals with autistic spectrum disorder have reduced level of neural interconnection between the frontal lobe (forebrain) and parietal lobe (posterior brain) compared with normal individuals. The low level of neural interconnection between the frontal lobe (forebrain) and parietal lobe in this case is neural communication impairment. Ab initio neural communication impairment accompanies many types of autistic spectrum disorder, and in the case of Rhett syndrome, the impairment can be genetic post-birth neural communication impairment. In this case, the neural communication impairment point can be the interface between the frontal lobe and the parietal lobe at which additional neural connection is supposed to be present. In another example, disruption in neural communication between the right hemisphere of the brain and the left hemisphere of the brain may be caused by external injury or by genetic causes. The disrupted neural communication between the right hemisphere of the brain and the left hemisphere of the brain constitutes neural communication impairment. In this case, the neural communication impairment point can be the interface between the right hemisphere and the left hemisphere at which additional neural connection is supposed to be present.

In a third embodiment, the first neural component is a sensory neuron located in a sensory component of a vertebrate being and the second neural component is a receptor neuron located in a cortex of the vertebrate being. The sensory neuron may be a neuron designed to detect vision, hearing, temperature, pressure, taste, smell, movement or actuation of a body muscle, or any other sensory function that a normal vertebrate being has the capacity for. The neuron communication impairment can be, for example, cortical blindness which occurs at optical nerves located between the retina and the visual cortex. In this case, the first neural component is one of the light-sensitive cells in the retina, the second neural component is the neuron in the visual cortex that is functionally related to the light-sensitive cells, and the neural communication pathway is the neural connection between the light-sensitive cell and the functionally related neuron in the visual cortex. The neural communication impairment point is the location at which the optical nerve connection is weakened or otherwise disrupted. In another example, the neuron communication impairment can be tinnitis, which occurs at auditory nerves located between the superior caliculus (located next to the inner ear) and the auditory cortex. In this case, the first neural component is one of the neurons located in the nerves of the superior caliculus, the second neural component is the neuron in the auditory cortex that is functionally related to the neuron at the superior caliculus, and the neural communication pathway is the neural connection between the neuron at the superior caliculus and the functionally related neuron in the auditory cortex.

Applied external stimulation is provided to the first neural component and the second neural component. Application of the external stimulation the first neural component and the second neural component is simultaneous in order to induce neural signals originating from the first neural component and the second neural component to reach the neural communication impairment point with minimal time differential. In order to simultaneously provide the external stimulation to the first and second neural components, a synchronous signal generating device can be employed in conjunction with multiple output electrodes. At least one output electrode among the multiple output electrodes, which is herein referred to a first electrode, is connected to a first point, which is located in the vicinity of the first neural component so that an electrical voltage applied to the first electrode induces a neural response in the first neural component. At least another output electrode among the multiple output electrodes, which is herein referred to a second electrode, is connected to a second point, which is located in the vicinity of the second neural component so that an electrical voltage applied to the second electrode induces a neural response in the second neural component.

Alternately, the applied stimulation may include any sonic stimulation, ultrasonic stimulation, magnetic stimulation (in which a steady state or dynamic magnetic field is applied), light stimulation, thermal stimulation (in which heat is applied), cryogenic stimulation (in which one or more neural element is subjected to exposure to a cold surface or a cold object), vibrational stimulation, pressure stimulation, vacuum stimulation, or any other sensory signal that may be applied in lieu of an applied electrical stimulation or in conjunction with an applied electrical stimulation. If employed, these external stimulations are applied simultaneously with application of other electrical or non-electrical stimulations.

Such external stimulation of paired neural components, which include a first neural component and a second neural component, induces generation and transmission of respective neural handshake signals in the neural pathway. The stimulation signals are applied to the first and second neural components simultaneously with application of the charge signal, and induce generation of a first neural handshake signal that originates from the first neural element and a second neural handshake signal that originates from a second neural element. As the two neural handshake signals converge and meet at the neural communication impairment point coincidentally, i.e., with a temporal and spatial overlap, paired neural components can reestablish communication. Even after removal of externally applied signals, neural communication arises between the paired neural components in a form that is essentially normal for the vertebrate being, i.e., in a manner that would occur had there been no dysfunction in the neural pathway. The rehabilitation process thus includes stimulation of neuronal growth over time at or around the neural communication impairment point, and the natural communication process between such neuronally coupled components is invigorated. Preferably, application of the applied signals and induced charging of the neural pathway are performed simultaneously at both the first and second neural components. The applied signals may be electromagnetic or sonic, but are preferably electrical.

In a preferred inherent charge-enhanced neural stimulation (iCENS), the charge is generated inherently as part of the process that generates the handshake signals. In an iCENS system a single circuit is formed extending from the first neural component to the second via the neural pathway of interest. It is this circuit latter that creates the required charge signal. In a preferred embodiment, no additional electrical or non-electrical stimulation is applied to the neural pathway under treatment while the first external stimulation is applied to the first neural component and the second external stimulation is applied to the second neural component.

In augmented charge-enhanced neural stimulation (aCENS), a charging signal is directly applied to a portion of the neural pathway from a signal source independent of the relevant sources stimulating the neuronal handshake signals. In an aCENS system the signals are isolated from each other wherein each set of electrodes of a respective signal source forms a separate isolated circuit applied to the site of interest. The charge signal is applied in its own isolated circuit.

Further, in CENS embodiments, the use of charging signal enhances the likelihood of a successful handshake, in a sense by amplifying the handshake neural signals in the pathway near the neural communication impairment points of interest.

Any such charging signal in a sense amplifies the effect of at least one handshake neural signal within the neural pathway, and makes the handshake more likely to succeed. Thus, the synchronized application of charging signal enhances the coupling of the two induced handshake neural signals, and invigorates communication between the stimulated first and second neural components. The charging signal is a signal having the function of electrically charging the neural pathway. The charging signal can be a direct current signal, a rectangular wave signal, one or more pluses, or a varying waveform. The charging signal can be applied proximate to the neural communication impairment point at the same time as the synchronized applied electrical stimulation signals are applied to the first and second neural components. Preferably the stimulation and charging is done simultaneously.

Figure 20:
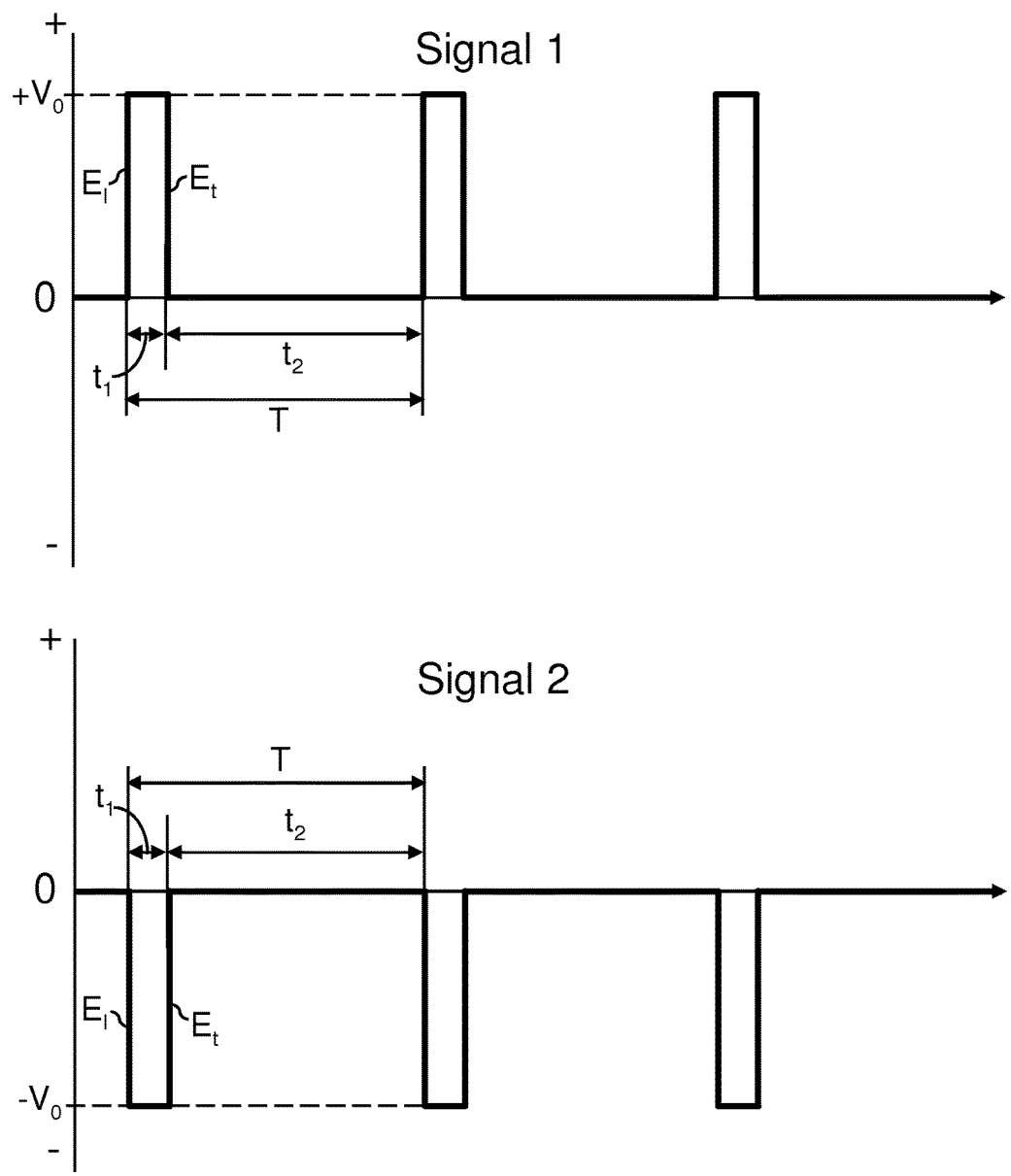
FIG. 20 show graphs illustrating exemplary external stimulation waveforms that can be employed in inherent charge-enhanced neural stimulation (iCENS).

Referring to FIG. 20, two graphs illustrate exemplary external stimulation waveforms employed in inherent charge-enhanced neural stimulation (iCENS). The external stimulation waveforms may be applied as electrical voltage signals applied to a first point located in proximity to a first neural component and a second point located in proximity to a second neural component. In this case, a first electrical voltage signal having the waveform represented by "Signal 1" can be applied to the first point through a first conductive electrode, and a second electrical voltage signal having the waveform represented by "Signal 2" can be applied to the second point through a second conductive electrode.

The first electrical voltage signal and the second electrical voltage signal can be a series of electrical voltage pulses that are simultaneously turned on. Each pulse may have a leading edge that represents a transition in voltage from a zero voltage potential to a non-zero voltage potential. Further, each pulse may have a trailing edge that represents a transition in voltage from a non-zero voltage potential to a zero voltage potential. Here, the leading edges $E_l$ of the first electrical voltage signal are referred to as first leading edges, and the trailing edges $E_t$ of the first electrical voltage signal are referred to as first trailing edges. Likewise, the leading edges $E_l$ of the second electrical voltage signal are referred to as second leading edges, and the trailing edges $E_t$ of the second electrical voltage signal are referred to as second trailing edges.

In a preferred embodiment, each first leading edge coincide temporally with, i.e., occurs simultaneously with, a second leading edge, and vice versa. Likewise, each first trailing edge coincides temporally with a second trailing edge, and vice versa. Both the first electrical voltage signal and the second electrical voltage signal can be, but does not necessarily have to be, a periodic signal provided that sufficient time is allowed between each pair of consecutive electrical pulses to allow stimulated neural pathway to return to a steady state, i.e., a sufficiently long period of time without neural excitation. The time required to allow sufficient relaxation of the stimulated neural pathway differs depending on the nature of the stimulated neural pathway, and is at least 0.01 second (corresponding to 100 Hz), and is typically at least 0.1 second (corresponding to 10 Hz), and is preferably at least 0.5 second (corresponding to 2 Hz).

If periodic signals are employed, i.e., if the pulses have the same time period between each consecutive leading edges $E_1$, the period T of the periodic signal may be from 0.01 second to 1200 seconds, and is typically from 0.1 second to 120 seconds, and is preferably from 0.5 second to 10 seconds. The duty cycle, i.e., the ratio of the duration of each pulse relative to the period T, of each pulse may be from 0.001% to 10%, and is typically from 0.005% to 2%, and is preferably from 0.01% to 1%, although lesser and greater duty cycles can also employed provided the periodic electrical signal is sufficient to induce neural signals in the first neural component and the second neural component. In FIG. 20, the duty cycle is the ratio of $t_1$ to $(t_1+t_2)$, i.e., $t_1/(t_1+t_2)=t1/T$. The duration of each electrical pulse can be from 40 microseconds to 10 milliseconds, and can be typically from 200 microseconds to 2 milliseconds, and can be preferably from 400 microseconds to 1 millisecond, although lesser and greater pulse durations can also be employed.

The total repetition of electrical pulses delivered to a vertebrate being in one treatment session can be from 20 pulses to 100,000 pulses, and can be typically from 200 pulses to 10,000 pulses, and can be preferably from 1,000 pulses to 4,000 pulses, although lesser and greater number of electrical pulses can be employed in a single treatment session. Multiple sessions, each separated by a cell recuperation period to allow natural recovery and cell growth in the neural communication impairment point, can be employed. The optimal time interval between consecutive sessions depends on the nature and cell growth speed of the nerve pathway, and is typically from 3 days to 3 weeks, although lesser and greater time intervals can also be employed.

In one embodiment, the polarity of the first electrical voltage signal and the second electrical voltage signal can be the opposite. For example, the first electrical voltage signal can consist of a series of positive signals and the second electrical voltage signal can consist of a series of negative signals that are synchronous with the first electrical voltage signal, or vice versa. While constant magnitude electrical pulses are illustrated in FIG. 20, the electrical pulses of the first electrical voltage signal and the second electrical voltage signal can in general have any functional waveform provided that the two electrical voltage signals are synchronous. A pair of electrical signals with opposite polarity has shown superior results in clinical trials in practice of this method and is preferred, while other practices of the invention are possible.

In addition, it is possible for each of the first electrical voltage signal and the second electrical voltage signal to include a mixture of positive and negative pulses provided that each pulse in a signal is applied simultaneously with application of another pulse in the other signal. Further, each pulse may be unipolar, i.e., may consist of a single period of a positive voltage or a single period of a negative voltage, as illustrated in FIG. 20, or may be bipolar (includes a positive pulse immediately followed by a negative pulse or vice versa), or multipolar (includes more than two pulses of different polarities). Among clinically tested and proven waveforms for the purpose of iCENS, unipolar pulses tended to produce the best results so far. Further, each pulse in an electrical voltage signal can have an arbitrary waveform provided that a corresponding pulse exists in the other electrical voltage signal. Thus, the first electrical voltage signal and the second electrical voltage signal can be represented as a scalar multiple of a common waveform f(t) as a function of time t, i.e., the first electrical voltage signal can be represented as $\alpha_1 \cdot f(t)$ and the second electrical voltage signal can be represented as $\alpha_2 \cdot f(t)$ in which $\alpha_1$ and $\alpha_2$ are non-zero real numbers. As discussed above, $\alpha_1 \cdot \alpha_2$ is preferably negative in a preferred embodiment (i.e., for a set of signals with different polarities), but it is possible to practice this embodiment of the present invention such that $\alpha_1 \cdot \alpha_2$ is positive (i.e., for a set of signals with the same polarities). As discussed above, a time interval at which the voltage of each electrical voltage signal is at zero volt is present between each consecutive electrical pulses.

The amplitude $V_0$ of each electrical pulse can be adjusted depending on the nature of the neural pathway and the nature and degree of the neural communication impairment therein. The amplitude $V_0$ herein refers to the absolute value of the maximum voltage deviation from zero volt in the waveform, which may consist of rectangular pulses or may include other types of pulses (such as triangular pulses). The optimal value for the amplitude $V_0$ of each electrical pulse can be determined by applying a series of test pulses, which can have the same functional waveform as the electrical pulses to be employed during treatment but has less amplitude. The amplitude of the test pulses can be increased iteratively until a neural response is observed in the vertebrate being under treatment. For example, if the treatment is directed to paraplegic conditions, the appropriate neural response may be twitching of muscles targeted for treatment and the amplitude of the test pulses can be increased until such a twitching of muscles is observed in a dysfunctional limb. In general, an optimal signal magnitude for applied stimulation signals of any type can be determined so that the applied stimulation signals for the purpose of treatment are applied at the optimal signal magnitude. The optimal signal magnitude can be determined, for example, by gradually increasing a magnitude of test signals applied to the first and second points. The optimal signal magnitude is set at a signal magnitude at which a muscle associated with the first or second neural element begins to react to the test signals.

As an illustrative example, the typical current density needed to treat paraplegic conditions in humans can be from 15 A/m$^2$ to 60 A/m$^2$, and preferably from 25 A/m$^2$ to 38 A/m$^2$, although lesser and greater current density may be used depending on the nature of the disability, the duration of each pulse, and the size of the individual under treatment. Such current density levels typically translate to about 20 V in the pulse magnitude of the applied electrical signals.

In inherent charge-enhanced neural stimulation (iCENS) mode, an active electrode is placed in proximity to one of the first and second neural components and a reference electrode is placed in proximity to the other of the first and second neural components. Because a neural pathway under treatment is present between the first and second neural components, the neural pathway is located between an active electrode and a reference electrode, and an external electrical signal is applied across the first neural component and the second neural component in the iCENS mode.

In the iCENS mode, a single circuit established between a pair of two neural components, i.e., the first neural component and the second neural component, in a neural pathway worthy of invigoration. A first stimulation signal is applied to the first neural component and generates a first neural handshake signal that propagates along the neural pathway, and a second stimulation signal is applied to the second neural components and generates a second neural handshake signal that propagates along the neural pathway. In general, the first stimulation signal and the second stimulation signal may be a signal of any type provided that the first and second stimulation signals are synchronized. For example, the first stimulation signal and the second stimulation signal can be electrical pulses of opposite polarities. An electrical current flows in the neural pathway between the first and second components to provide a biased charge to the neural pathway. In an embodiment in which the first neural element is a neuron in a cortex and the second neural element is located in an extremity, e.g., a limb of a vertebrate being, the charge signal has a positive electrical flow from the cortex down the neural pathway toward the associated extremity of interest.

In the iCENS mode, the charge signal is part of the interaction of the stimulation signals applied across the two neural components. In one illustrative embodiment, with stimulation applied between a neural component associated with the motor cortex and a neural component associated with an extremity, the motor cortex is held at a positive level relative to a relatively negative level at the extremity. The handshake signals are related but inverted. The charge signal is relatively constant at least in pertinent part and flows in the neural pathway simultaneously with the handshake signals. The charge-enabled neural handshake signals meet on the neural pathway, and cause the natural restorative processes of that vertebral being to be invigorated, resulting in the improvement in communication between the two neural components adequately so as to revive the natural processes of neural generation and to reverse, for example, paralysis of the treated vertebral being.

Figure 21A:
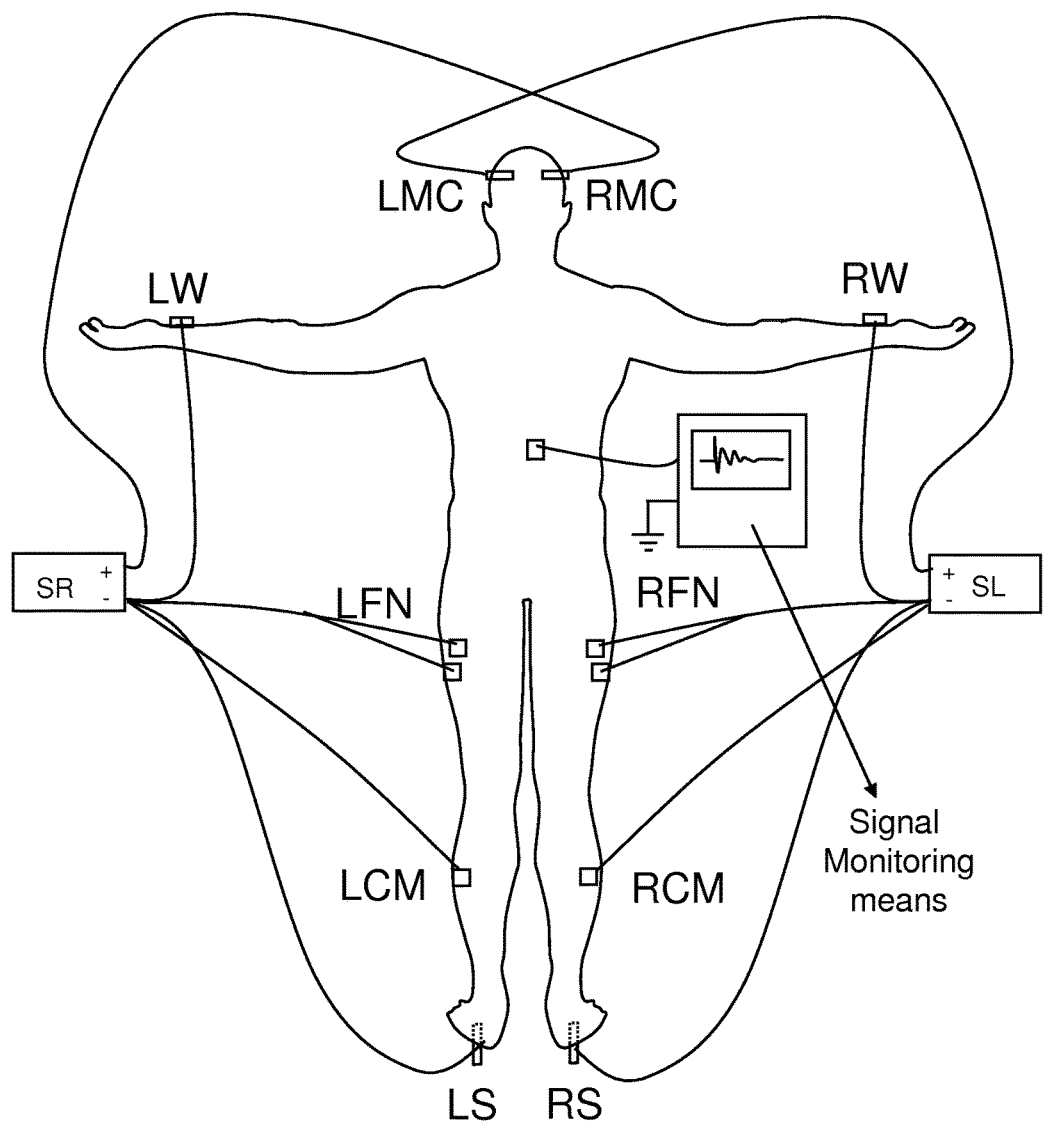
FIG. 21A is an illustration of a first exemplary electrode configuration for inherent charge-enhanced neural stimulation (iCENS) for the purpose of cortico-motor stimulation.

Referring to FIG. 21A, a first exemplary electrode configuration for iCENS is illustrated for the first embodiment, in which the first neural component is a neuron in a motor cortex and the second neural component is a lower motoneuron controlling the movement of a muscle. Because a neural pathway between a motor cortex and a muscle is stimulated, this configuration is referred to as dipolar cortico-muscular stimulation (dCMS).

In this configuration, a first stimulation signal is provided to a motor cortex in the form of a first electrical voltage signal, and a second stimulation signal is provided to at least one muscle region in the form of a second electrical voltage signal. In the case of a patient with a single disability in a limb, a set of a first electrode and a second electrode may be employed to form a single stimulation circuit including a single neural pathway within a vertebrate being. In some cases, a set of a first electrode and multiple second electrodes may be employed to form a single stimulation circuit including a single neural pathway or multiple overlapping or non-overlapping stimulation circuits including multiple neural pathways. If a patient includes a first disability located in a right side limb and a second disability located in a left side limb, two sets of first electrodes and second electrodes may be employed to form at least one stimulation circuit including at least one neural pathway starting from a right side motor cortex and at least another stimulation circuit including at least one neural pathway. In the case of a patient with multiple disabilities, multiple stimulation circuits may be present in a single configuration as illustrated in FIG. 21A. For example, in the case of a quadriplegic patient who has disabilities in the movement of the right arm, left arm, right leg, and left leg, multiple muscle regions may be stimulated simultaneously or in rotation in conjunction with stimulation at a corresponding motor cortex, which can be the left side motor cortex for disabilities in movement in the right side of the body or the right side motor cortex for disabilities in movement in the left side of the body.

Each stimulation circuit includes an electrical signal generator unit or a subunit thereof that has a positive output electrode and a negative output electrode, a first lead wire from one of the one of the positive and negative output electrodes to a first electrode, a second lead wire from the other of the positive and negative output electrodes to a second electrode, the first electrode contacting a first point in proximity to a first neural component, the second electrode contacting a second point in proximity to a second neural component, a region between the first point and the first neural component, a region between the second point and the second neural component, and a neural pathway between the first neural component and the second neural component. While FIG. 21A shows a configuration in which the positive output electrode (labeled "+") of a signal generator unit (SR or SL) is connected to a first electrode and the negative output electrode (labeled "−") is connected to second electrodes, the opposite configuration is also possible.

In any given stimulation circuit including a neural pathway in an iCENS configuration, one of the first electrode and the set of at least one second electrodes is an active electrode and the other of the first electrode and the set of at least one second electrodes is a reference electrode. Thus, an external electrical signal is applied across the first electrode and the set of at least one second electrodes. For a first electrode is placed on the right side motor cortex, each of the second electrode(s) in the corresponding set of at least one second electrode is placed on the left side of the body in the configuration in FIG. 21A. Likewise, for a first electrode is placed on the left side motor cortex, each of the second electrode(s) in the corresponding set of at least one second electrode is placed on the right side of the body in the configuration in FIG. 21A.

In the illustrated example of FIG. 21A representing an electrode placement configuration for a quadriplegic patient, two first electrodes and eight second electrodes may be employed. One of the first electrodes is placed on the right side motor cortex of the patient. Preferably, this electrode is placed at a right side junction between Bregma area and the coronal suture. This electrode is hereafter referred to as a right motor cortex (RMC) electrode. The RMC electrode is placed such that an electrical voltage signal is applied to the neurons of the right side motor cortex and induces a first neural handshake signal therefrom. Another of the first electrodes is placed on the left side motor cortex of the patient. Preferably, this electrode is placed at a left side junction between Bregma area and the coronal suture. This electrode is hereafter referred to as a left motor cortex (LMC) electrode. The LMC electrode is placed such that an electrical voltage signal is applied to the neurons of the left side motor cortex and induces a first neural handshake signal therefrom.

The eight second electrodes can be placed, respectively, at the right side inner wrist, at the lest side inner wrist, at the right side fibular nerve ending, at the left side fibular nerve ending, at the belly of the right side calf muscle, at the belly of the left side calf muscle, at the side sole, and at the left sole respectively. The eight electrodes are herein referred to as a right wrist (RW) electrode, a left wrist (LW) electrode, a right fibular nerve (RFN) electrode, a left fibular nerve (LFN) electrode, a right calf muscle (RCM) electrode, a left calf muscle (LCM) electrode, a right sole (RS) electrode, and a left sole (LS) electrode, respectively. Each of the eight electrodes is placed such that an electrical voltage signal is applied to the neurons of the underlying area and induces a second neural handshake signal therefrom.

Six neural pathways are present in this configuration. A first neural pathway extends from the right side motor cortex to the left side wrist between the RMC electrode and the LW electrode. A first electrical voltage signal applied to the RMC electrode and a second electrical voltage signal applied to the LW electrode, which are synchronized so that electrical pulses are applied simultaneously, induce two neural handshake signals that propagate along the neural pathway between the right side motor cortex and the left side wrist and converge at a neural communication impairment point located within the impaired neural pathway. The handshake at the neural communication impairment point provides biological stimulation to the cells at the neural communication impairment point. In general, the location of the neural communication impairment point depends on the nature of trauma or genetic defect.

A second neural pathway extends from the left side motor cortex to the right side wrist between the LMC electrode and the RW electrode. Another first electrical voltage can be applied to the LMC electrode and another second electrical voltage signal can be applied to the RW electrode, either simultaneously with or alternately with the application of the first and second electrical voltage signals applied to the RMC electrode and the LW electrode. The second neural pathway may be stimulated, by applying electrical signals to the LMC electrode and the RW electrode, simultaneously, alternately, or independently with stimulation of the first neural pathway.

In one embodiment, a first common signal can be applied to the RMC electrode and the LMC electrode, and a second common signal can be applied to the LW electrode and the RW electrode. In this case, the first common signal and the second common signal may have the opposite polarity as illustrated in FIG. 20. Experimental data generated from clinical trials suggest that applying positive electrical pulses to the RMC electrode and the LMC electrode while applying negative electrical pulses to the LW electrode and the RW electrode produces superior results than applying negative electrical pulses to the RMC electrode and the LMC electrode while applying positive electrical pulses to the LW electrode and the RW electrode.

A third neural pathway extends from the right side motor cortex to the left side fibular nerve between the RMC electrode and the LFN electrode. The left side fibular nerve includes a lower motoneuron that actuates the left side calf muscle. A first electrical voltage signal applied to the RMC electrode and a second electrical voltage signal applied to the LCM electrode, which are synchronized so that electrical pulses are applied simultaneously, induce two neural handshake signals that propagate along the neural pathway between the right side motor cortex and the left side fibular nerve and converge at a neural communication impairment point located within the impaired neural pathway. The handshake at the neural communication impairment point provides biological stimulation to the cells at the neural communication impairment point. In general, the location of the neural communication impairment point depends on the nature of trauma or genetic defect. The third neural pathway may be stimulated, by applying electrical signals to the RMC electrode and the LFN electrode, simultaneously, alternately, or independently with stimulation of the first neural pathway and/or the second neural pathway.

The LCM electrode placed on the belly of the left calf muscle can reinforce rehabilitation of the neural communication impairment point by providing movement of the left calf muscle while the two neural handshake signals converge at the neural communication impairment point between the right side motor cortex and the left fibular nerve. An induced signal is generated at sensory nerves at the left calf muscle by another second electrical voltage signal applied to the LCM electrode, and may be transmitted to the right side motor cortex through a different neural pathway, which is a sensory-cortico pathway. The electrical signal applied to the LCM electrode can be the same as the electrical signal applied to the LFN electrode.

A fourth neural pathway extends from the left side motor cortex to the right side fibular nerve between the LMC electrode and the RFN electrode. The right side fibular nerve includes a lower motoneuron that actuates the right side calf muscle. A first electrical voltage can be applied to the LMC electrode and a second electrical voltage signal can be applied to the RFN electrode, either simultaneously with or alternately with the application of the first and second electrical voltage signals applied to the LMC electrode and the RFN electrode. The fourth neural pathway may be stimulated, by applying electrical signals to the LMC electrode and the RFN electrode, simultaneously, alternately, or independently with stimulation of the first neural pathway and/or the second neural pathway and/or the third neural pathway.

The RCM electrode placed on the belly of the right calf muscle can reinforce rehabilitation of the neural communication impairment point by providing movement of the right calf muscle while the two neural handshake signals converge at the neural communication impairment point between the left side motor cortex and the right fibular nerve. An induced signal is generated at sensory nerves at the right calf muscle by another second electrical voltage signal applied to the RCM electrode, and may be transmitted to the left side motor cortex through a different neural pathway, which is a sensory-cortico pathway. The electrical signal applied to the RCM electrode can be the same as the electrical signal applied to the RFN electrode.

A fifth neural pathway extends from the right side motor cortex to neurons on the left sole between the RMC electrode and the LS electrode. A first electrical voltage signal applied to the RMC electrode and a second electrical voltage signal applied to the LS electrode, which are synchronized so that electrical pulses are applied simultaneously, induce two neural handshake signals that propagate along the neural pathway between the right side motor cortex and the neurons located on the left sole and converge at a neural communication impairment point located within the impaired neural pathway. The handshake at the neural communication impairment point provides biological stimulation to the cells at the neural communication impairment point. In general, the location of the neural communication impairment point depends on the nature of trauma or genetic defect. The fifth neural pathway may be stimulated, by applying electrical signals to the RMC electrode and the LS electrode, simultaneously, alternately, or independently with stimulation of the first neural pathway and/or the second neural pathway and/or the third neural pathway and/or the fourth neural pathway A sixth neural pathway extends from the left side motor cortex to the right sole between the LMC electrode and the RS electrode. The right side fibular nerve includes a lower motoneuron that actuates the right side calf muscle. The fifth neural pathway may be stimulated, by applying electrical signals to the LMC electrode and the RS electrode, simultaneously, alternately, or independently with stimulation of the first neural pathway and/or the second neural pathway and/or the third neural pathway and/or the fourth neural pathway and/or the fifth neural pathway.

In one embodiment, a first set of electrical stimulation signals can be applied across the RMC electrode and at least one of the LW electrode, the LFN electrode, the LCM electrode, and the LS electrode. Simultaneously, alternately, or independently, a second set of electrical stimulation signals can be applied across the LMC electrode and at least one of the RW electrode, the RFN electrode, the RCM electrode, and the RS electrode. As discussed above, the amplitude of the electrical signals applied to these electrodes are selected to be above the threshold amplitude above which the limbs move, for example, by twitching, in response to the applied voltages. Thus, depending on the interrelationship among applied electrical signals, the left side limbs and the right side limbs may move simultaneously, alternately, or independently, in response to the applied electrical signals.

A signal monitoring means can be employed in any iCENS configuration. The signal monitoring means is configured to detect a handshake of the first periodic neural signals and the second periodic neural signals at a point in the neural pathway. For example, an oscilloscope or any other signal capturing electronic device can be wired to enable detection of a voltage signal or a current signal at the point in the neural pathway, which can be a neural pathway trigger site.

However, it will be appreciated that positive indication of such neural handshake is not required in order to successfully practice the present invention. As another matter of observation, the correct signal strength of stimulation may be observed by increasing the signal until a muscle associated with the stimulated neural pathway "twitches", at which time the signal strength is considered to be adequate.

In general, a first means for inducing a first neural handshake signal and a second means for inducing a second neural handshake signal are provided in the iCENS mode. The first means is configured to supply a first applied stimulation signal to a first neural component of a neural pathway of interest. The first applied stimulation signal includes a first set of signal pulses having a magnitude that induces the first neural component to issue the first neural handshake signal on the neural pathway. The second means configured to supply a second applied stimulation signal to a second neural component of the neural pathway of interest. The second applied stimulation signal includes a second set of signal pulses having a magnitude that induces the second neural component to issue the second neural handshake signal on the neural pathway contemporaneously with the first neural handshake signal. The neural pathway has a base charge potential prior to application of the first and second applied stimulation signals, and the charge is applied as part of the stimulation.

Figure 21B:
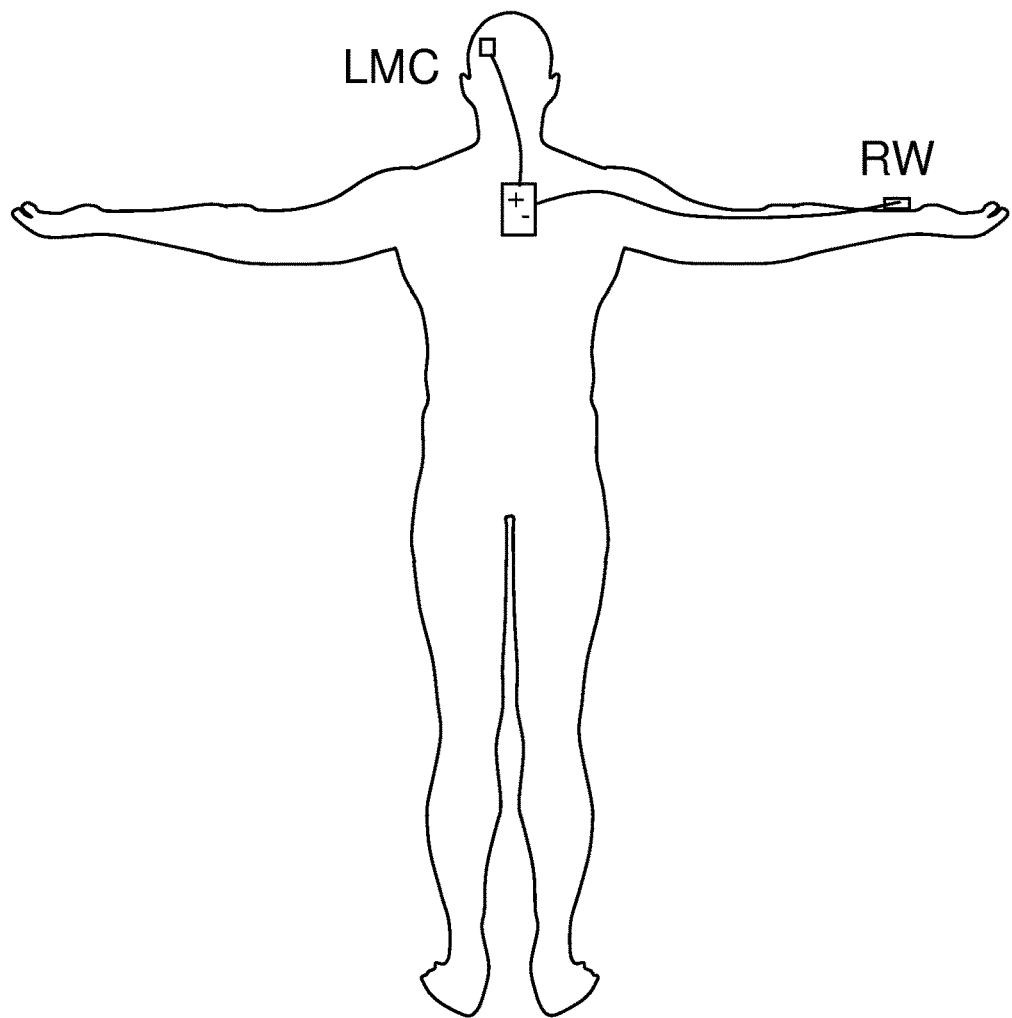
FIG. 21B is an illustration of a second exemplary electrode configuration for iCENS for the purpose of cortico-motor stimulation.

In one embodiment, at least one of the first means and the second means is an implanted device that is temporarily or permanently implanted in the vertebrate being or a portable device carried by the vertebrate being. FIG. 21B illustrates a second exemplary electrode configuration for iCENS for the purpose of cortico-motor stimulation, in which the first means and the second means are integrated as a single implanted or portable device that is implanted, for example, on the backside skin, or carried on the clothing of the vertebrate being, if the vertebrate being is a human being. Thus, a patient can be treated at a convenient time of her own choosing once the implanted or portable device is mounded on her, either temporarily or semi-permanently, i.e., permanently until removal.

Figure 22A:
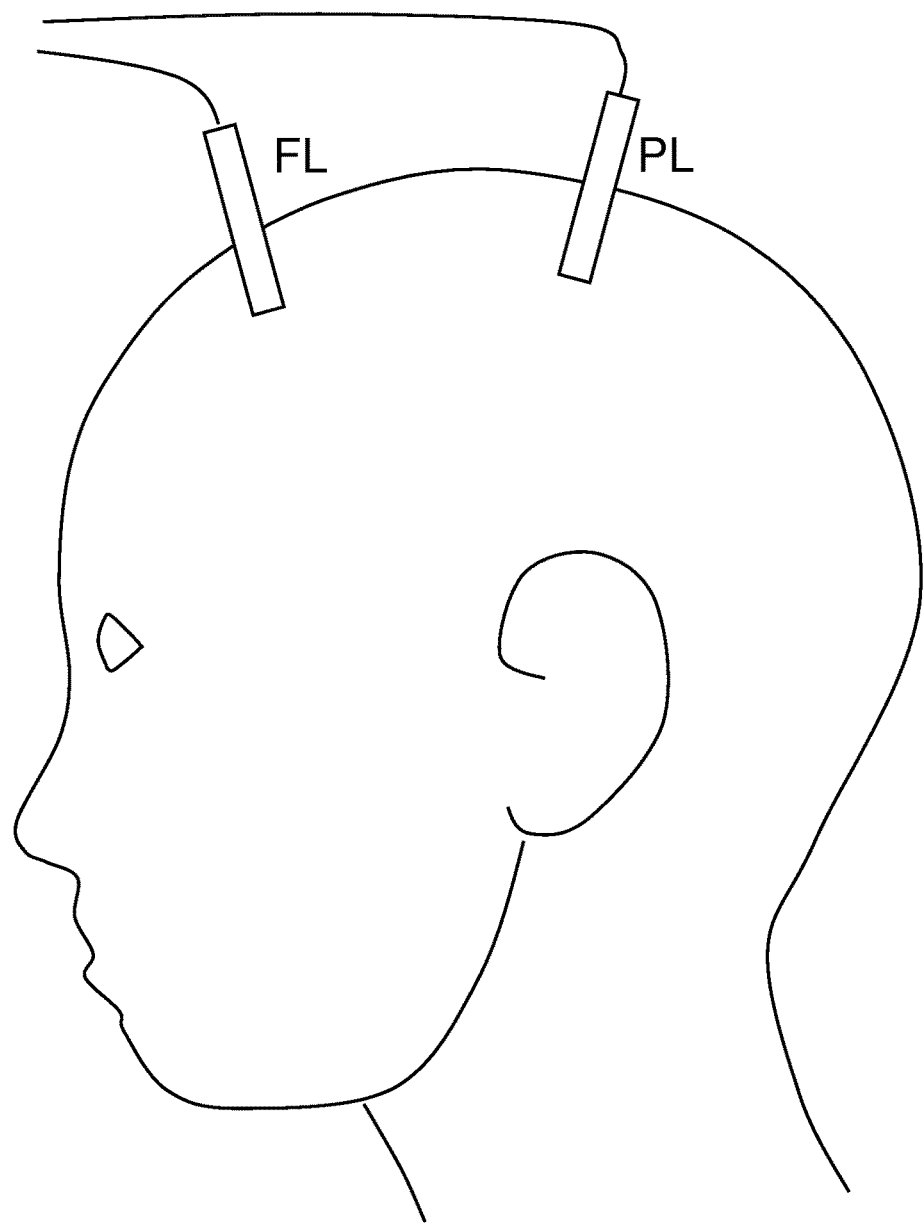
FIG. 22A is an illustration of a third exemplary electrode configuration for iCENS for the purpose of inter-cortex stimulation.

Referring to FIG. 22A, a third exemplary electrode configuration for iCENS is illustrated for the second embodiment, in which the first neural component is a neuron in a first cortex and the second neural component is a neuron in a second cortex In this configuration, a first stimulation signal is provided to a first cortex in the form of a first electrical voltage signal, and a second stimulation signal is provided to a second cortex in the form of a second electrical voltage signal. For example, individuals with autistic spectrum disorder may be treated to enhance the neural connection between the frontal lobe (forebrain) and parietal lobe (posterior brain). A first electrode, which is herein referred to as a frontal lobe (FL) electrode, is placed on the frontal lobe of the brain of the patient, and a second electrode, which is herein referred to as a parietal lobe (PL) electrode, is placed on the parietal lobe of the brain of the patient. The neural communication impairment point can be the interface between the frontal lobe and the parietal lobe at which additional neural connection is supposed to be present. By applying electrical pulse signals across the FL electrode and the PL electrode, a first neural handshake signal is generated from a neuron in the frontal lobe on one end of the neural pathway, a second neural handshake signal is generated from a neuron in the parietal lobe on the other end of the neural pathway. The two induced neural signals converge at the neural communication impairment point along a neural pathway between the two neurons, and generate a handshake, thereby rehabilitating neural communication impairment point, i.e., strengthening the neural pathway.

In another exemplary configuration, individuals with disruption in neural communication between the right hemisphere of the brain and the left hemisphere of the brain may be treated to enhance neural communication between the two hemispheres. The disrupted neural communication between the right hemisphere of the brain and the left hemisphere of the brain constitutes neural communication impairment. In this case, the neural communication impairment point can be the interface between the right hemisphere and the left hemisphere at which additional neural connection is supposed to be present. A first electrode, which is herein referred to as a right hemisphere electrode, is placed on the right hemispehre of the brain of the patient, and a second electrode, which is herein referred to as a left hemisphere electrode, is placed on the left hemisphere of the brain of the patient. By applying electrical pulse signals across the right hemisphere electrode and the left hemisphere electrode, a first neural handshake signal is generated from a neuron in the right hemisphere on one end of the neural pathway, a second neural handshake signal is generated from a neuron in the left hemisphere on the other end of the neural pathway. The two induced neural signals converge at the neural communication impairment point along a neural pathway between the two neurons, and generate a handshake, thereby rehabilitating neural communication impairment point, i.e., strengthening the neural pathway.

In the third embodiment, the first neural component is a sensory neuron located in a sensory component of a vertebrate being and the second neural component is a receptor neuron located in a sensory cortex of the vertebrate being. The sensory neuron may be a neuron designed to detect vision, hearing, temperature, pressure, taste, smell, movement or actuation of a body muscle, or any other sensory function that a normal vertebrate being has the capacity for. The neural pathway to be treated is a sensory-cortico neural pathway that transmits sensation as detected by the sensory neuron to the receptor neuron in the sensory cortex. The external stimulation to the first neural component may be applied as electrical signals, or any other type of signal that can generate a neural response in the sensory neuron. For example, non-electrical signals that can be applied as external stimulation may be pulsed light irradiation in the case of an optical nerve, or can be an auditory pulse in the case of an auditory nerve.

Figure 22B:
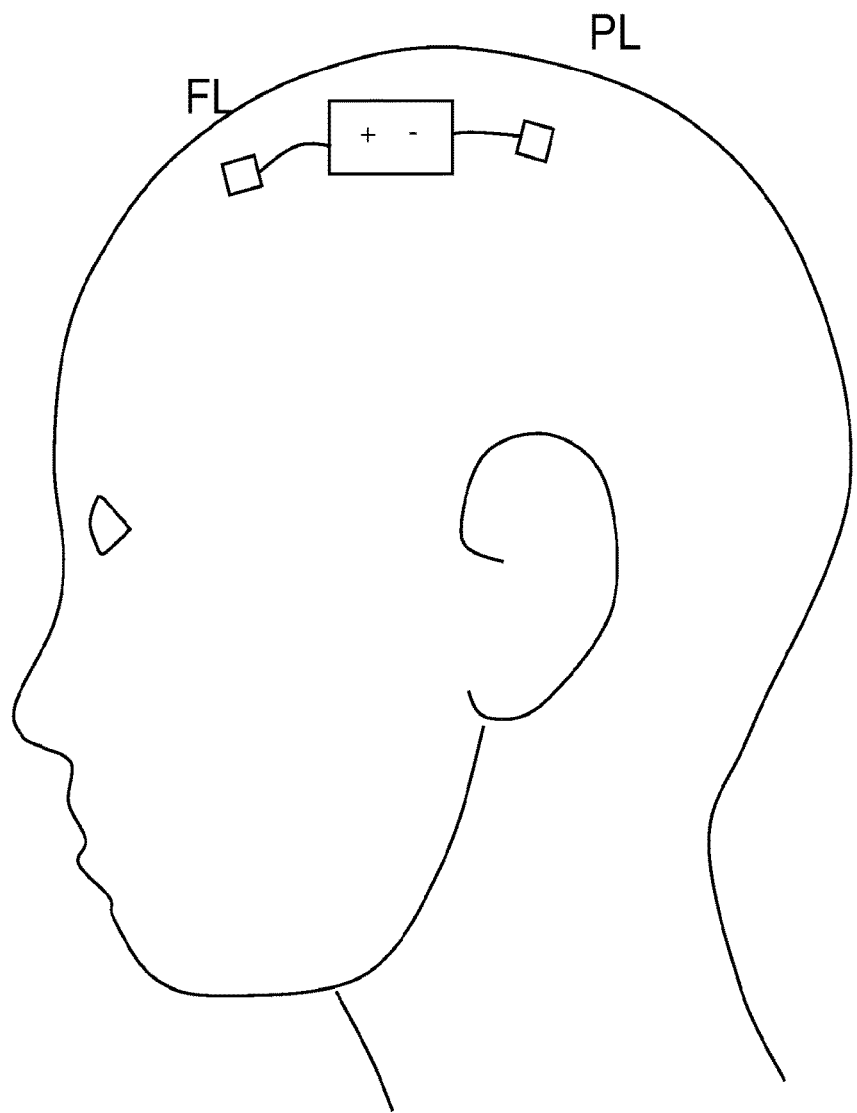
FIG. 22B is an illustration of a fourth exemplary electrode configuration for iCENS for the purpose of inter-cortex stimulation.

At least one of the first means and the second means can be an implanted device that is temporarily or permanently implanted in the vertebrate being or a portable device carried by the vertebrate being in this embodiment as well. Referring to FIG. 22B, a fourth exemplary electrode configuration for iCENS for the purpose of inter-cortex stimulation is illustrated for the second embodiment. The first means and the second means are integrated as a single implanted or portable device that is implanted, for example, on the skin of the head, or carried on in a cap or specifically designed carrying apparatus, if the vertebrate being is a human being. Thus, a patient can be treated at a convenient time of her own choosing once the implanted or portable device is mounded on her, either temporarily or semi-permanently, i.e., permanently until removal.

Figure 23A:
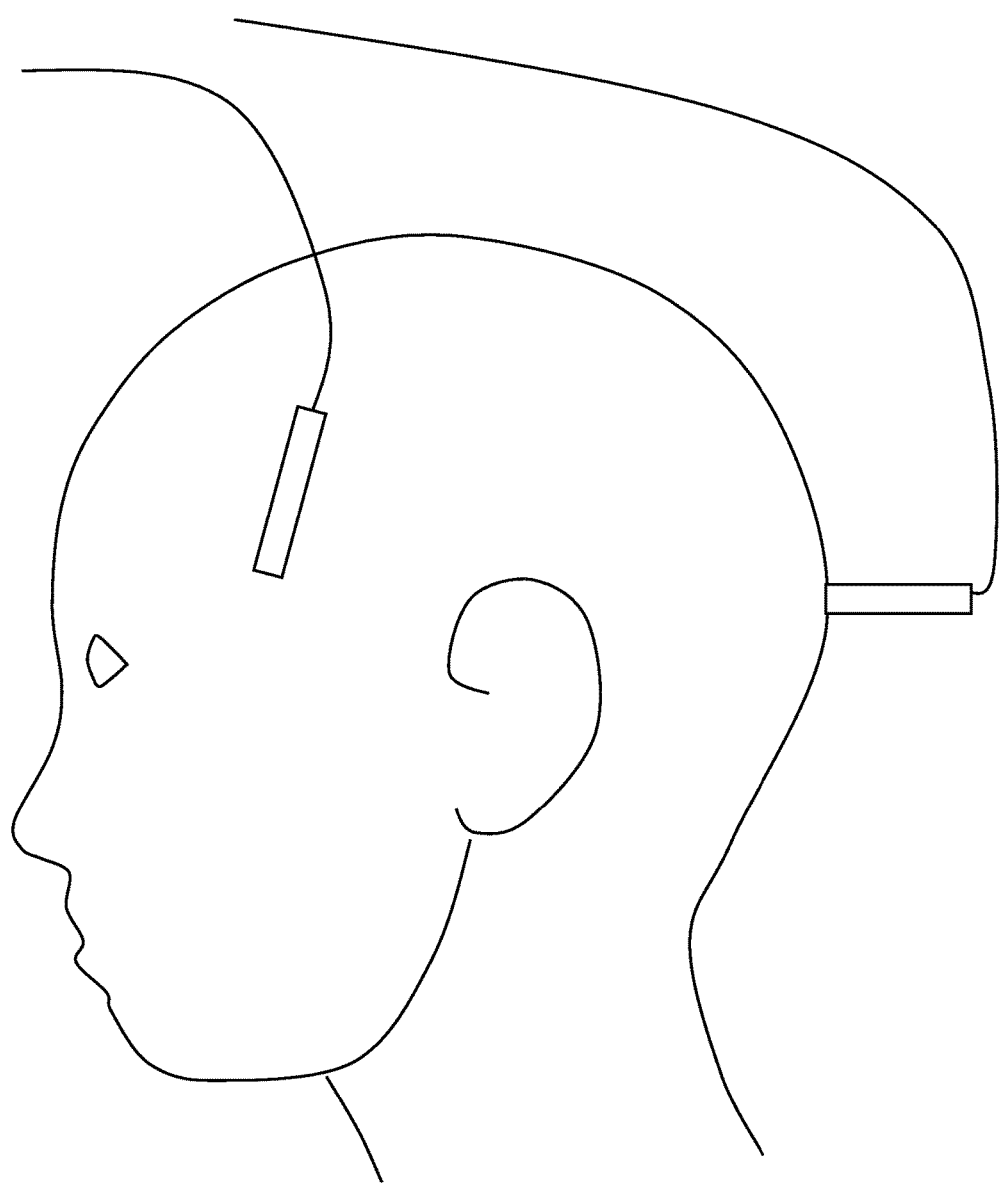
FIG. 23A is an illustration of a fifth exemplary electrode configuration for iCENS for the purpose of sensory-cortico stimulation, in which the first neural component is a light-sensitive cell in the retina and the second neural component is a neuron in the visual cortex.

Referring to FIG. 23A, a fifth exemplary electrode configuration for iCENS is illustrated for the third embodiment for sensory-cortico stimulation, in which the first neural component is a light-sensitive cells in the retina and the second neural component is a neuron in the visual cortex. In this illustrative example, the neuron communication impairment can be cortical blindness which occurs at optical nerves located between the retina and the visual cortex. The neuron in the visual cortex that is functionally related to the light-sensitive cell, i.e., is intended to receive a neural signal indicating detection of light by the light-sensitive cell, and the neural communication pathway is the neural connection between the light-sensitive cell and the functionally related neuron in the visual cortex. The neural communication impairment point is the location at which the optical nerve connection is weakened or otherwise disrupted.

In one case, a first electrode can be placed at any region in proximity to optical nerves, and a second electrode can be placed on the visual cortex. Multiple neural pathways can be stimulated between optical nerves and the neurons in the visual cortex. By applying stimulation signals across the first electrode and the second electrode, first neural handshake signals are generated from optical nerves, and second neural handshake signals are generated from neurons in the visual cortex. A pair of neural signals, including a first handshake signal and a second handshake signal, converges at each neural communication impairment point in each neural pathway, and generates a handshake, thereby rehabilitating neural communication impairment point, i.e., strengthening the neural pathway. Alternately, the electrical stimulation of the optical nerves may be replaced by pulsed light illumination that is synchronized with the application of an electrical signal having the same duration as the light illumination at each pulse, and the light illumination can be used to induce the first neural handshake signal.

Figure 23B:
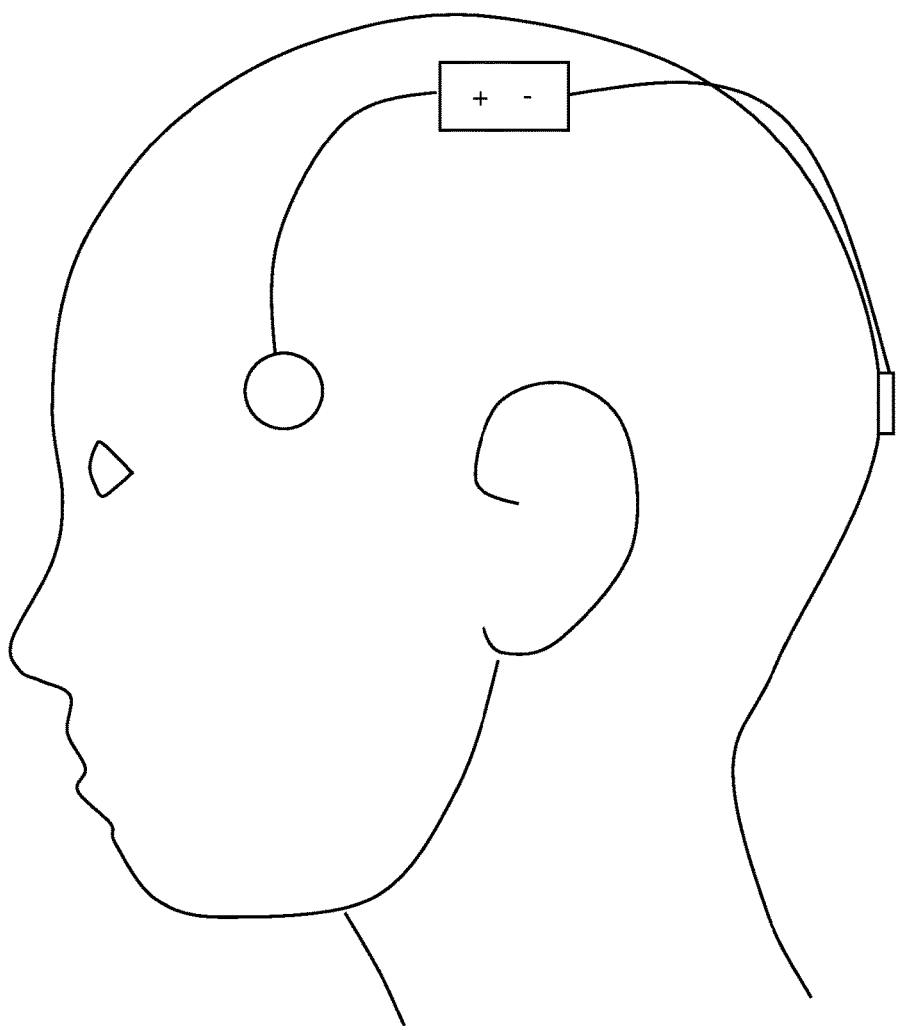
FIG. 23B is an illustration of a sixth exemplary electrode configuration for iCENS for the purpose of sensory-cortico stimulation, in which the first neural component is a light-sensitive cell in the retina and the second neural component is a neuron in the visual cortex.

At least one of the first means and the second means can be an implanted device that is temporarily or permanently implanted in the vertebrate being or a portable device carried by the vertebrate being in this embodiment as well. Referring to FIG. 23B, a sixth exemplary electrode configuration for iCENS for the purpose of sensory-cortico stimulation is illustrated for the third embodiment. The first means and the second means are integrated as a single implanted or portable device that is implanted, for example, on the skin of the head, or carried on in a cap or specifically designed carrying apparatus, if the vertebrate being is a human being. Thus, a patient can be treated at a convenient time of her own choosing once the implanted or portable device is mounded on her, either temporarily or semi-permanently, i.e., permanently until removal.

Figure 23C:
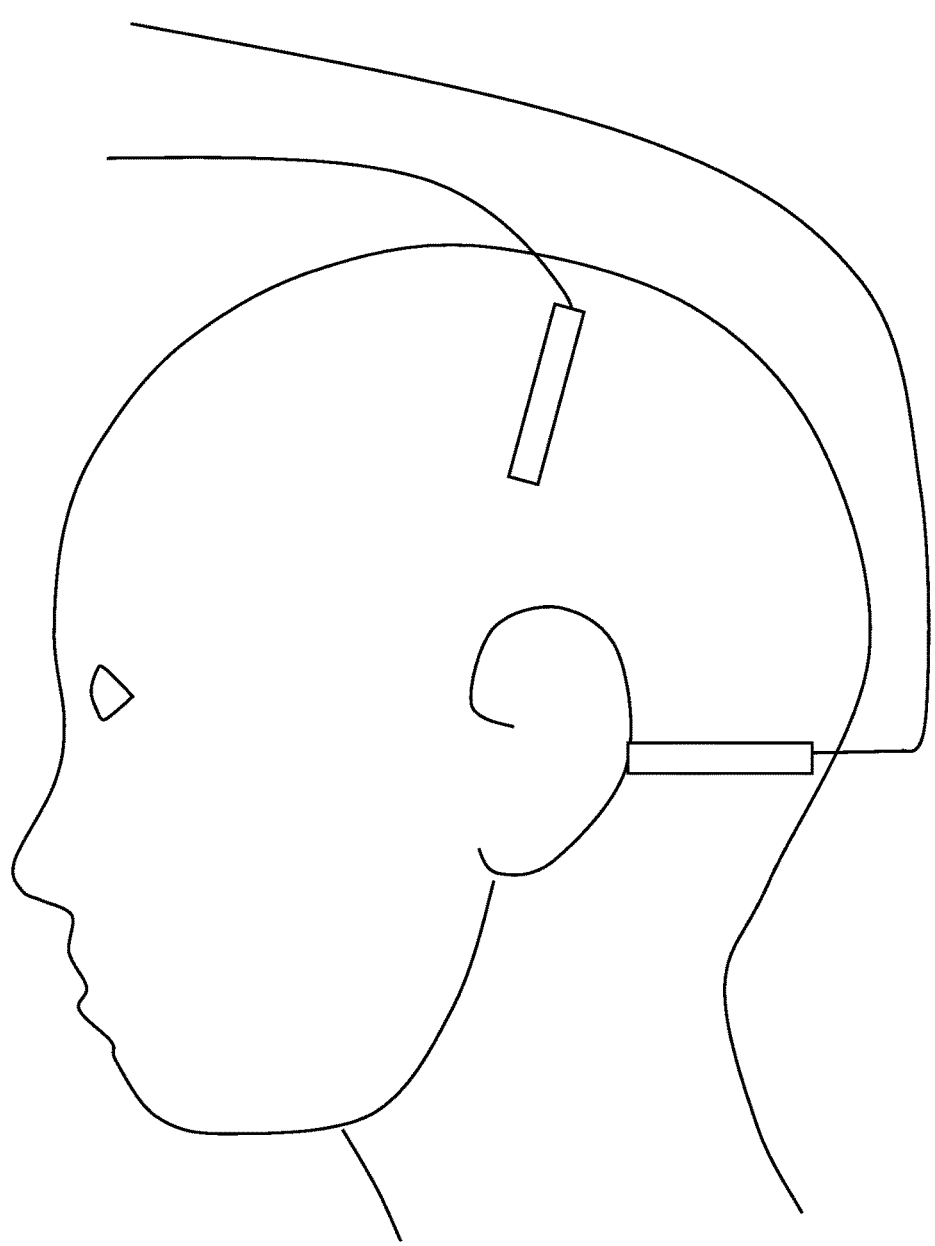
FIG. 23C is an illustration of a seventh exemplary electrode configuration for iCENS for the purpose of sensory-cortico stimulation, in which the first neural component is an auditory nerve and the second neural component is the auditory cortex.

Referring to FIG. 23C, a seventh exemplary electrode configuration for iCENS is illustrated for the third embodiment for sensory-cortico stimulation, in which the first neural component is an auditory nerve and the second neural component is the auditory cortex. In this illustrative example, the neuron communication impairment can be tinnitus, which occurs at auditory nerves located between the superior caliculus (located next to the inner ear) and the auditory cortex. The neuron in the auditory cortex that is functionally related to the auditory nerve, i.e., is intended to receive a neural signal indicating detection of sound by the auditory nerve, and the neural communication pathway is the neural connection between the auditory nerve and the functionally related neuron in the auditory cortex. The neural communication impairment point is the location at which the auditory connection is weakened or otherwise disrupted.

In one case, a first electrode can be placed at any region in proximity to the auditory nerves, and a second electrode can be placed on the auditory cortex. Multiple neural pathways can be stimulated between auditory nerves and the neurons in the auditory cortex. By applying stimulation signals across the first electrode and the second electrode, first neural handshake signals are generated from auditory nerves, and second neural handshake signals are generated from neurons in the auditory cortex. A pair of neural signals, including a first handshake signal and a second handshake signal, converges at each neural communication impairment point in each neural pathway, and generates a handshake, thereby rehabilitating neural communication impairment point, i.e., strengthening the neural pathway. Alternately, the electrical stimulation of the auditory nerves may be replaced by pulsed sonic stimulation that is synchronized with the application of an electrical signal having the same duration as the sonic stimulation at each pulse, and the sonic stimulation can be used to induce the first neural handshake signal.

Figure 23D:
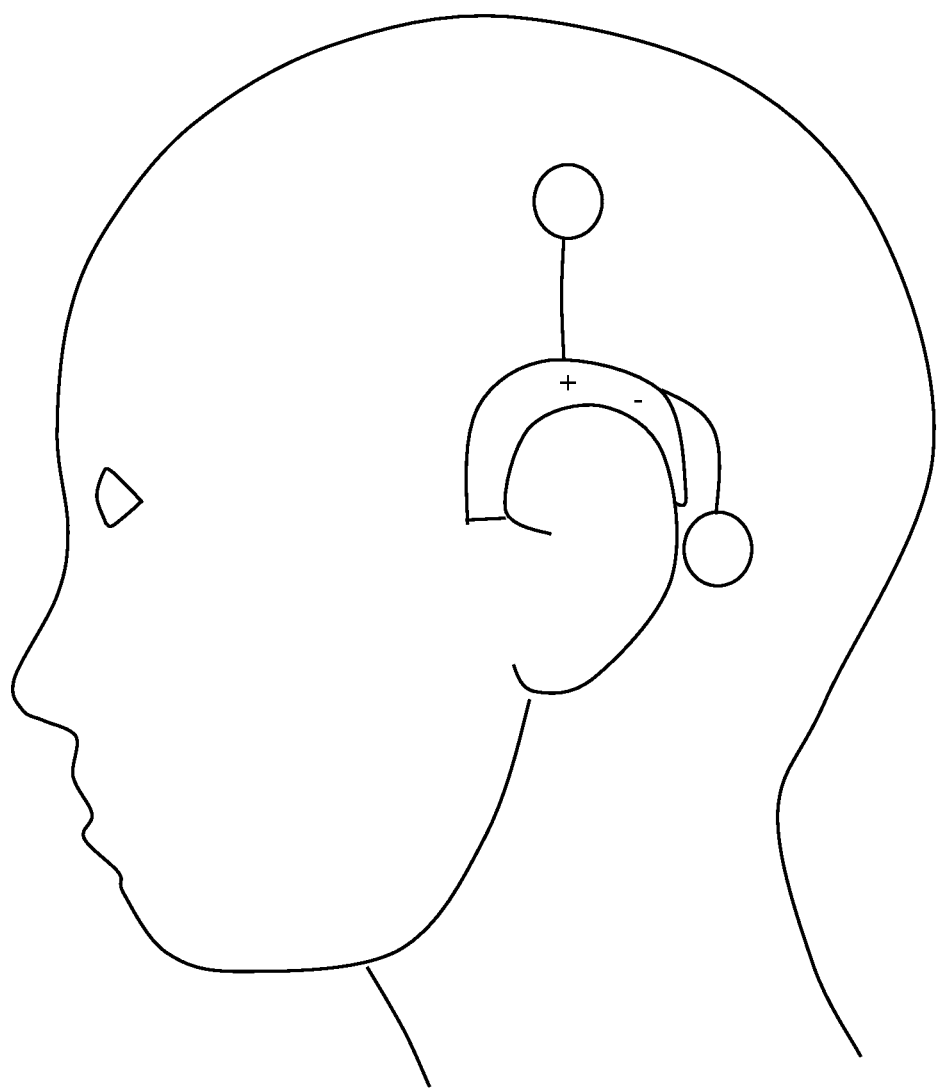
FIG. 23D is an illustration of an eighth exemplary electrode configuration for iCENS for the purpose of sensory-cortico stimulation, in which the first neural component is an auditory nerve and the second neural component is the auditory cortex.

At least one of the first means and the second means can be an implanted device that is temporarily or permanently implanted in the vertebrate being or a portable device carried by the vertebrate being in this embodiment as well. Referring to FIG. 23D, an eighth exemplary electrode configuration for iCENS for the purpose of sensory-cortico stimulation is illustrated for the third embodiment. The first means and the second means are integrated as a single implanted or portable device that is implanted, for example, on the skin of the head, or carried on in a cap or specifically designed carrying apparatus such as a device configured to be placed between the head and an earlobe, if the vertebrate being is a human being. Thus, a patient can be treated at a convenient time of her own choosing once the implanted or portable device is mounded on her, either temporarily or semi-permanently, i.e., permanently until removal.

In general, an applied electrical stimulation signal or any other sensory signal that can induce a neural signal can be employed to generate a first neural handshake signal, provided that a second electrode connected to a sensory cortex is provided with an applied electrical stimulation signal that is synchronized with the application of the signal that generates the first neural handshake signal. The alternative applied stimulation signals include sonic stimulation signals, ultrasonic stimulation signals, magnetic stimulation signals (in which a steady state or dynamic magnetic field is applied), light stimulation signals, thermal stimulation signals (in which heat is applied), cryogenic stimulation signals (in which one or more neural element is subjected to exposure to a cold surface or a cold object), vibrational stimulation signals, pressure stimulation signals, vacuum suction stimulation signals, any other sensory signal, or a combination thereof.

Figure 24:
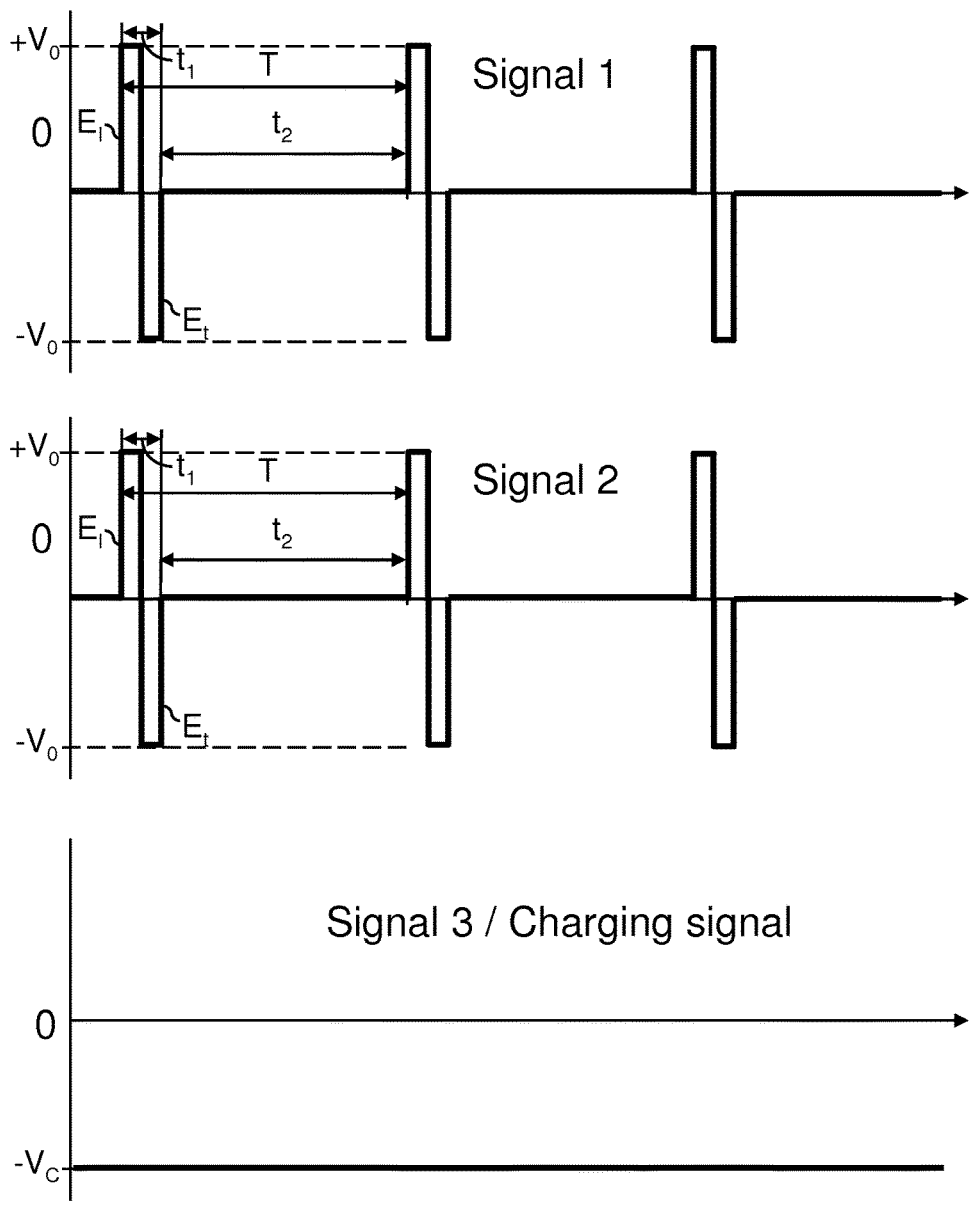
FIG. 24 shows graphs illustrating exemplary external stimulation waveforms that can be employed in augmented charge-enhanced neural stimulation (aCENS).

Referring to FIG. 24, exemplary external stimulation waveforms that may be employed in augmented charge-enhanced neural stimulation (aCENS) are illustrated. The external stimulation waveforms may be applied as electrical voltage signals applied across multiple sets of at least one active electrode and at least one reference electrode. In each set of at least one active electrode and at least one reference electrode placed on a living being, the at least one active electrode is placed in proximity to a neural element or a muscle, and the corresponding at least one reference electrode is placed farther away from the neural element or the muscle. The charge signal is separately applied A first active electrode is placed on a first point located in proximity to a first neural element, and a second active electrode is placed on a second point located in proximity to a second neural component. In this case, a first electrical voltage signal having the waveform represented by "Signal 1" can be applied to the first point through a first conductive electrode, and a second electrical voltage signal having the waveform represented by "Signal 2" can be applied to the second point through a second conductive electrode. In addition, a third electrical voltage signal represented by "Signal 3" can be applied to a third point, which is located in the middle of the neural pathway between the first neural element and the second neural element. As an illustrative example, the first neural element can be a right side motor cortex, the second neural element can be a left femoral nerve ending, and the third point may be a vertebra located on a spine, which is in the middle of the neural pathway between the right side motor cortex and the left femoral nerve ending.

The third point is a neural pathway trigger site, which is located on a neural pathway and associated with the control of the functionality of the neural pathway. Such neural pathway trigger sites are points at which control of the functionality of the neural pathway is centralized, and may be a particular vertebra on a spine or a site of a neural branching point associated with the neural pathway. The third point may coincide with the neural communication impairment point, it if is known. Alternately, if the neural communication impairment point is not known, the third point may be selected as a location known to be associated with the type of neural communication impairment under treatment. The third electrical voltage signal is also referred to as a "charging signal" because the effect of application of the third electrical voltage is to electrically charge the third point with another induced electrical signal.

In general, the charging signal is a signal having a charging function. As such, the charging signal can be a direct current (DC) signal, and is preferably a constant negative voltage signal that remains constant throughout a treatment session. Preferably, the charging signal is applied proximate to the neural communication impairment point of interest at the same time as the synchronized applied electrical stimulation signals are applied to the first and second neural components. In other words, the stimulation of the first and second neural elements and the charging of the third point can be done simultaneously.

The first and second electrical voltage signals can be a series of electrical voltage pulses that are simultaneously turned on. Each pulse may have a leading edge that represents a transition in voltage from a zero voltage potential to a non-zero voltage potential. Further, each pulse may have a trailing edge that represents a transition in voltage from a non-zero voltage potential to a zero voltage potential. Here, the leading edges $E_l$ of the first electrical voltage signal are referred to as first leading edges, and the trailing edges $E_t$ of the first electrical voltage signal are referred to as first trailing edges. Likewise, the leading edges $E_l$ of the second electrical voltage signal are referred to as second leading edges, and the trailing edges $E_t$ of the second electrical voltage signal are referred to as second trailing edges.

In a preferred embodiment, each first leading edge coincide temporally with a second leading edge, and each first trailing edge coincide temporally with a second trailing edge. The first and second electrical voltage signals can be, but does not necessarily have to be, a periodic signal provided that sufficient time is allowed between each pair of consecutive electrical pulses to allow stimulated neural pathway to return to a steady state, i.e., a sufficiently long period of time without neural excitation. The time required to allow sufficient relaxation of the stimulated neural pathway differs depending on the nature of the stimulated neural pathway, and is at least 0.01 second, and is typically at least 0.1 second, and is preferably at least 0.5 second.

If periodic signals are employed, i.e., if the pulses have the same time period between each consecutive leading edges $E_l$, the period T of the periodic signal may be from 0.01 second to 1200 seconds, and is typically from 0.1 second to 120 seconds, and is preferably from 0.5 second to 10 seconds. The duty cycle, i.e., the ratio of the duration of each pulse relative to the period T, of each pulse may be from 0.001% to 10%, and is typically from 0.005% to 2%, and is preferably from 0.01% to 1%, although lesser and greater duty cycles can also employed provided the periodic electrical signal is sufficient to induce neural signals in the first neural component and the second neural component. In FIG. 24, the duty cycle is the ratio of $t_l$ to $(t_1+t_2)$, i.e., $t_1/(t_1+t_2)=t_1/T$. The duration of each electrical pulse can be from 40 microseconds to 10 milliseconds, and can be typically from 200 microseconds to 2 milliseconds, and can be preferably from 400 microseconds to 1 millisecond, although lesser and greater pulse durations can also be employed.

The total repetition of electrical pulses delivered to a vertebrate being in one treatment session can be from 20 pulses to 100,000 pulses, and can be typically from 200 pulses to 10,000 pulses, and can be preferably from 1,000 pulses to 4,000 pulses, although lesser and greater number of electrical pulses can be employed in a single treatment session. Multiple sessions, each separated by a cell recuperation period to allow natural recovery and cell growth in the neural communication impairment point, can be employed. The optimal time interval between consecutive sessions depends on the nature and cell growth speed of the nerve pathway, and is typically from 3 days to 3 weeks, although lesser and greater time intervals can also be employed.

In one embodiment, the first and second electrical voltage signals can have the same polarity. For example, the first and second electrical voltage signals can consist of a series of signals having the same polarity whenever the signal is non-zero. While bipolar electrical pulses are illustrated in FIG. 20, the electrical pulses of the first and second electrical voltage signals can in general have any functional waveform provided that the two electrical voltage signals are synchronous. In some cases, the first and second electrical voltage signals may be identical, i.e., have the same phase, amplitude, and polarity. While employment of an identical voltage waveform for the first and second electrical voltage signals has shown good results in clinical trials of this embodiment and is a preferred method, it is possible to practice this embodiment of the present invention such that the amplitude of one of the first and second electrical voltage signals is modulated by a constant positive scalar number from the other.

In addition, it is possible for each of the first and second electrical voltage signals to include another types of mixture of positive and negative pulses provided that each pulse in a signal is applied simultaneously with application of another pulse in the other signal. Further, each pulse may be unipolar, i.e., may consist of a single period of a positive voltage or a single period of a negative voltage, or may be bipolar as illustrated in FIG. 24, or multipolar. Among clinically tested and proven waveforms for the purpose of aCENS, bipolar pulses tended to produce the best results so far. Further, each pulse in an electrical voltage signal can have an arbitrary waveform provided that a corresponding pulse exists in the other electrical voltage signal. Thus, the first and second electrical voltage signals can be represented as a positive scalar multiple of a common waveform f(t) as a function of time t, i.e., the first electrical voltage signal can be represented as $\beta_1 \cdot f(t)$, and the second electrical voltage signal can be represented as $\beta_2 \cdot f(t)$. In this case, $\beta_1$ and $\beta_2$ are both positive or both negative. As discussed above, a time interval at which the voltage of each electrical voltage signal is at zero volt is present between each consecutive electrical pulses.

The amplitude $V_0$ of each electrical pulse can be adjusted depending on the nature of the neural pathway and the nature and degree of the neural communication impairment therein. The amplitude $V_0$ herein refers to the absolute value of the maximum voltage deviation from zero volt in the waveform, which may consist of rectangular pulses or may include other types of pulses (such as triangular pulses). The optimal value for the amplitude $V_0$ of each electrical pulse can be determined by applying a series of test pulses, which can have the same functional waveform as the electrical pulses to be employed during treatment but has less amplitude. The amplitude of the test pulses can be increased iteratively until a neural response is observed in the vertebrate being under treatment. For example, if the treatment is directed to paraplegic conditions, the appropriate neural response may be twitching of muscles targeted for treatment and the amplitude of the test pulses can be increased until such a twitching of muscles is observed in a dysfunctional limb.

Figure 25A:
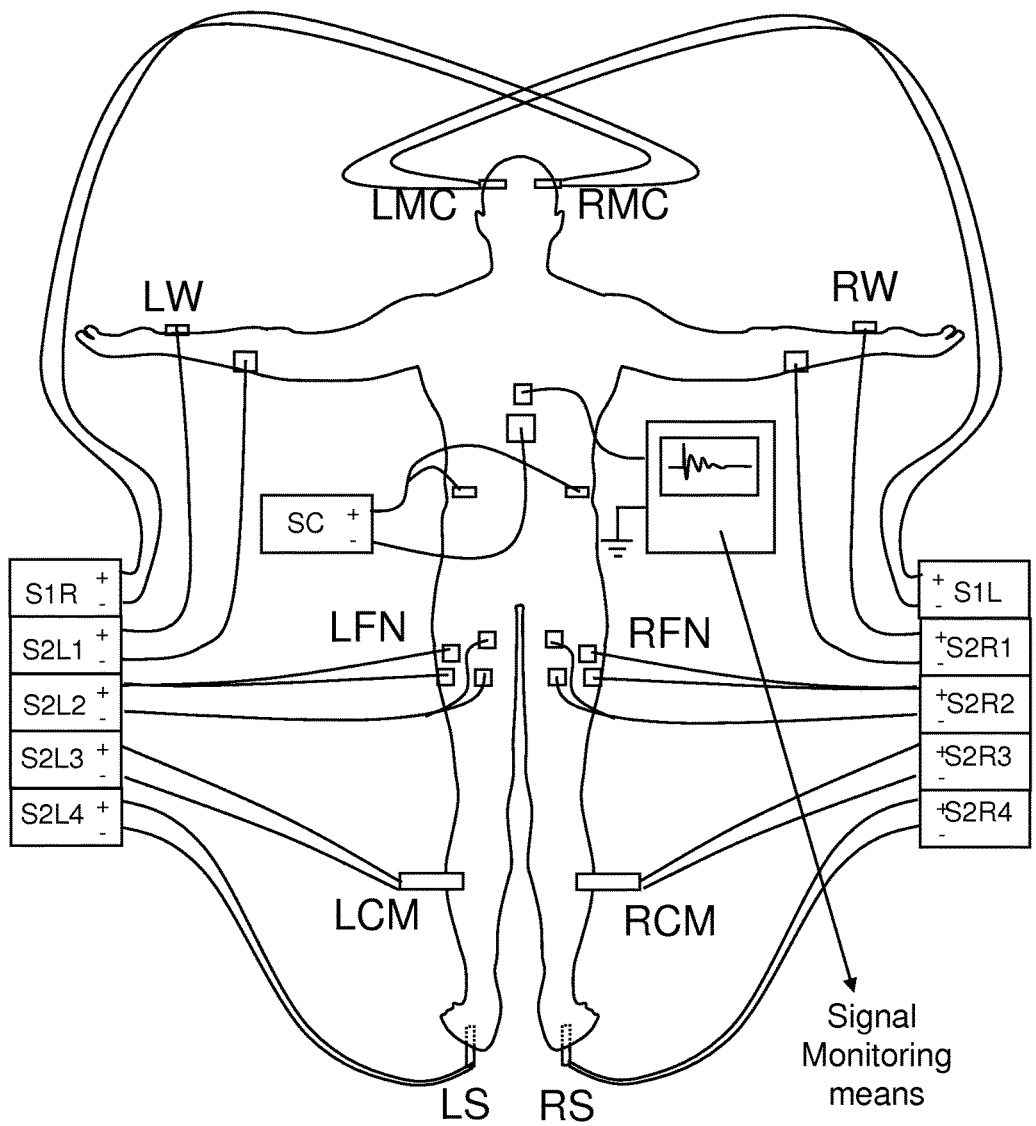
FIG. 25A is an illustration of a first exemplary electrode configuration for aCENS with stimulation signal generators and charging signal generators that are fixed in location.

Referring to FIG. 25A, an exemplary electrode configuration for augmented charge-enhanced neural stimulation (aCENS) is illustrated. The configuration of FIG. 25A may be derived from the configuration of FIG. 21A or any configuration derived therefrom, provided that at least one neural pathway exists. Thus, at least one neural pathway present in the configuration of FIG. 25A can include at least one neural pathway from a right motor cortex to any of the left wrist, the left fibular nerve, and the left sole and/or at least one neural pathway from a left motor cortex to any of the right wrist, the right fibular nerve, and the right sole. When the treated neural pathway crosses over from the left side of the spine to the right side of the spine, the mode of aCENS is referred to as trans-spinal direct current (tsDC) method.

In this configuration, a first stimulation signal is provided to a motor cortex in the form of a first electrical voltage signal across a first active electrode located at the first point and a first reference electrode located in the vicinity of the first point. The first point is located in proximity to a first neural element such as a mortor cortex. A second stimulation signal is provided to a second point in the form of a second electrical voltage signal across a second active electrode located at the second point and a second reference electrode located in the vicinity of the second point. The second point is located in proximity to a second neural element such as a motoneuron functionally related to a muscle. A charging signal is provided to a neural pathway trigger site located at a neural pathway between the first neural component and the second neural component. The charging signal is a constant voltage signal, and is preferably, a negative voltage signal. The treated neural pathway is thus located between a first active electrode to which the first electrical voltage signal is applied and a second active electrode to which the second electrical voltage signal is applied. The first and second electrical voltage signals can have the same waveform and polarity, and may be identical to each other.

In the case of a patient with a single disability in a limb, at least three electrode sets are employed. The three electrode sets include:
  a. a first electrode set including at least one first active electrode and at least one reference electrode, wherein the at least one first active electrode is placed on a motor cortex;
  b. a second electrode set including at least one second active electrode and at least one second reference electrode, wherein the at least one second active electrode is placed on a nerve ending on a opposite side of the motor cortex relative to the spine; and
  c. a third electrode set including a third active electrode and at least one counterelectrode. In this case, the first electrical voltage signal (e.g., Signal 1 of FIG. 24) is applied across the at least one first active electrode and at least one first reference electrode, the second electrical voltage signal (e.g., Signal 2 of FIG. 24) is applied across the at least one second active electrode and at least one second reference electrode, and the charging signal (e.g., Signal 3 of FIG. 24), which is a constant voltage bias and is preferably a constant negative voltage bias, is applied across the third active electrode and the at least one counterelectrode.

In some case of a patient with a single disability in a limb, more than three electrode sets can be employed. The more than three electrode sets include:
  a. a first electrode set including at least one first active electrode and at least one reference electrode, wherein the at least one first active electrode is placed on a motor cortex;
  b. two or more second electrode sets, wherein each set of the two or more second electrode sets includes at least one second active electrode and at least one second reference electrode, wherein each of the at least one second active electrode is placed on a nerve ending or a muscle on a opposite side of the motor cortex relative to the spine; and c. a third electrode set including a third active electrode and at least one counterelectrode.

In this case, the first electrical voltage signal (e.g., Signal 1 of FIG. 24) is applied across the at least one first active electrode and at least one first reference electrode, the second electrical voltage signal (e.g., Signal 2 of FIG. 24) is applied across each pair of the at least one second active electrode and at least one second reference electrode in each of the two or more second electrode sets, and the charging signal (e.g., Signal 3 of FIG. 24), which is a constant voltage bias and is preferably a constant negative voltage bias, is applied across the third active electrode and the at least one counterelectrode.

If a patient includes a first disability located in a right side limb and a second disability located in a left side limb, at least five electrode sets can be employed to treat the two disabilities in the same treatment session. The five electrode sets include:

a. a right side first electrode set including at least one first active electrode and at least one reference electrode, wherein the at least one first active electrode in the right side first electrode set is placed on the right side motor cortex;

b. a left side first electrode set including at least one first active electrode and at least one reference electrode, wherein the at least one first active electrode in the left side first electrode set is placed on the left side motor cortex;

c. a right side second electrode set including at least one second active electrode and at least one second reference electrode, wherein the at least one second active electrode in the right side second electrode set is placed on a nerve ending on the right side of the spine;

d. a left side second electrode set including at least one second active electrode and at least one second reference electrode, wherein the at least one second active electrode in the left side second electrode set is placed on a nerve ending on the left side of the spine; and e. a third electrode set including a third active electrode and at least one counterelectrode.

In this case, the first electrical voltage signal (e.g., Signal 1 of FIG. 24) is applied across at least one first active electrode and at least one first reference electrode within each first electrode set, the second electrical voltage signal (e.g., Signal 2 of FIG. 24) is applied across each pair of the at least one second active electrode and at least one second reference electrode within each second electrode set, and the charging signal (e.g., Signal 3 of FIG. 24), which is a constant voltage bias and is preferably a constant negative voltage bias, is applied across the third active electrode and the at least one counterelectrode.

Each stimulation circuit includes a electrical signal generator unit or a subunit thereof that has a positive output electrode and a negative output electrode, a first lead wire from one of the one of the positive and negative output electrodes to a first electrode, a second lead wire from the other of the positive and negative output electrodes to a second electrode, an active electrode, a reference electrode located in the vicinity of the active electrode, and the region of the vertebrate being between the active electrode and the reference electrode.

Each active electrode contacts first point or a second point. The first point is located in proximity to a first neural component such as a neuron of a motor cortex. The second point is located in proximity to a second neural component or a muscle functionally related to the second neural component.

Each reference electrode is located in the vicinity of a corresponding active electrode, but the distance between the reference electrode and the corresponding electrode is typically greater than, and in some cases at least three times greater than, the distance between the corresponding active electrode and the corresponding neural component or muscle, i.e., the first neural component, the second neural component, or a muscle.

FIG. 25A shows a configuration in which the positive output electrode (labeled "+") of each electrical signal generator unit or a subunit of a signal generator (S1R, S2R1, S2R3, S2R4, S1L, S2L1, S2L2, S2L3, S2L4) is connected to an active electrode, and the negative output electrode (labeled "−") of each electrical signal generator unit or a subunit of a signal generator (S1R, S2R1, S2R3, S2R4, S1L, S2L1, S2L2, S2L3, S2L4) connected to second electrodes, the opposite configuration is also possible.

For example, a first active electrode can be placed in proximity to neurons in the right side motor cortex or in proximity to neurons in the left side motor cortex. The corresponding first reference electrode(s) can be placed around the first active electrode on the same side, i.e., the right side or the left side, of the body. For first electrodes placed on a cortex or any other part of the head, a first electrode may be structurally integrally formed with a corresponding first reference electrode.to form a concentric composite electrodes having the form of a cylinder. A concentric composite electrode includes an electrode extending from the center of an end portion and a reference electrode extending from a peripheral region of that end portion. Electrodes contacting a motor cortex, a calf muscle, and a sole in FIG. 25A are portrayed as concentric composite electrodes, although a pair of a first electrode and a first reference electrode may be employed as a separate non-integrated structure instead.

In some embodiment, an active electrode or a reference electrode can be split into multiple parts that contact different surfaces of the vertebrate being. In the illustrated example of FIG. 25A, which representing an electrode placement configuration for a quadriplegic patient, two first electrode sets and eight second electrode sets are employed. External electrical signals to the two first electrode sets are supplied by the electrical signal generator unit (or a subunit of a signal generator) labeled S1R and S2R. Specifically, S1R provides the external electrical signal to a right side first electrode set labeled RMC (representing right side motor cortex), and S1L provides the external electrical signal to a left side first electrode set labeled LMC (representing left side motor cortex). Each of the external electrical signals to the eight electrode sets is provided by the electrical signal generator unit (or a subunit of a signal generator) labeled S2R1, S2R3, S2R4, S2L1, S2L2, S2L3, and S2L4, respectively.

One of the first active electrodes is placed on the right side motor cortex of the patient. Preferably, this active electrode is placed at a right side junction between Bregma area and the coronal suture. This active electrode is hereafter referred to as a right motor cortex (RMC) active electrode. The RMC active electrode is placed such that an electrical voltage signal is applied to the neurons of the right side motor cortex and induces a first neural handshake signal therefrom. Another of the first active electrodes is placed on the left side motor cortex of the patient. Preferably, this active electrode is placed at a left side junction between Bregma area and the coronal suture. This active electrode is hereafter referred to as a left motor cortex (LMC) active electrode. The LMC active electrode is placed such that an electrical voltage signal is applied to the neurons of the left side motor cortex and induces a first neural handshake signal therefrom.

The eight second active electrodes can be placed, respectively, at the right side inner wrist, at the lest side inner wrist, at the right side fibular nerve ending, at the left side fibular nerve ending, at the belly of the right side calf muscle, at the belly of the left side calf muscle, at the side sole, and at the left sole respectively. The eight active electrodes are herein referred to as a right wrist (RW) active electrode, a left wrist (LW) active electrode, a right fibular nerve (RFN) active electrode, a left fibular nerve (LFN) active electrode, a right calf muscle (RCM) active electrode, a left calf muscle (LCM) active electrode, a right sole (RS) active electrode, and a left sole (LS) active electrode, respectively. Each of the eight active electrodes is placed such that an electrical voltage signal is applied to the neurons of the underlying area and induces a second neural handshake signal therefrom.

A second reference electrode is placed in the vicinity of each second electrode. Second reference electrodes are placed such that an electrical signal is applied across a pair of a second electrode and a corresponding second reference electrode. Each second reference electrode serves as a current return path for the electrical current supplied by the corresponding second active electrode, i.e., the applied electrical current flowing from or into a second electrode completes a circuit through the corresponding second reference electrode. In some embodiments, a second electrode may be structurally integrally formed with a second reference electrode.to form a concentric composite electrodes having the form of a cylinder. For example, at the right side calf muscle, the left side calf muscle, the right sole, and the left sole in the configuration of FIG. 25A, each second electrode is structurally intergrated with a second reference electrode.to form a composite electrode.

Six neural pathways are present in this configuration. A first neural pathway extends from the right side motor cortex to the left side wrist between the RMC electrode set and the LW electrode set. Each electrical voltage signal applied to the active electrodes induce a neural handshake signal. For example, a first electrical voltage signal applied to the RMC active electrode induces a first neural handshake signal, and a second electrical voltage signal applied to any of the LW active electrode, the LFN active electrode, and the LS active electrode induces a first neural handshake signal. Likewise, a first electrical voltage signal applied to the LMC active electrode induces a first neural handshake signal, and a second electrical voltage signal applied to any of the RW active electrode, the RFN active electrode, and the RS active electrode induces a first neural handshake signal. The first electrical voltage and the second electrical voltage are synchronized so that electrical pulses are applied simultaneously, induce two neural handshake signals that propagate along the neural pathway between the right side motor cortex and the left side wrist and converge at a neural communication impairment point located within the impaired neural pathway. The handshake at the neural communication impairment point provides biological stimulation to the cells at the neural communication impairment point. In general, the location of the neural communication impairment point depends on the nature of trauma or genetic defect.

A third electrical voltage signal is applied to a third point in the middle of the treated neural pathway. The third electrical voltage signal is also referred to as a "charging signal" because the effect of application of the third electrical voltage is to electrically charge the third point with another induced electrical signal. Such a charging signal in a sense amplifies the effect of at least one neural handshake signal within the neural pathway, and makes the handshake more likely to succeed. Thus, the synchronized application of charging signal enhances the coupling of the two induced neural handshake signals, and invigorates communication between the stimulated first and second neural components.

The charging signal is a signal having the function of electrically charging the neural pathway. Preferably, the charging signal is a direct current signal that remains constant throughout the application of the first and second external electrical signals applied across at least one active electrode and at least one reference electrode in each electrode set. The charging signal can be applied proximate to the neural communication impairment point at the same time as the synchronized applied electrical stimulation signals are applied to the first and second neural components. Preferably the stimulation and charging is done simultaneously.

As discussed above, the third point may coincide with the neural communication impairment point, it if is known. For example, the third point can be the vertebra at which a known spinal injury is present, i.e., the site of dysfunction (i.e., impairment) at a certain vertebra as in the case of a particular trauma to the spine. Alternately, if the neural communication impairment point is not known, the third point may be selected as a location known to be associated with the type of neural communication impairment under treatment. In this case, third point may be a site of a neural branch in the case of dysfunction (impairment) elsewhere in that communication pathway. Further more, health individuals may be treated with this method. In this case, the dysfunction will be understood to be a need to improve or strengthen a neural communication in a relatively healthy being.

If the neural pathway runs through the spine of a vertebrate being, the neural communication impairment point may be a site of dysfunction (i.e., impairment) at or adjacent a certain vertebra as in the case of a particular trauma to the spine, or may be a site of a neural branch in the case of dysfunction (impairment) anywhere or elsewhere in that communication pathway. For example, in the case of humans, such branch site would be where spinal cord neurons branch out to innervate the upper extremities (located between the C5 and T1 vertebrae) or branch out to innervate the lower extremities (located between the T9 and T12 vertebrae), depending upon location of any extremity of interest.

The charging signal is applied across a third active electrode and at least one counterelectrode. The third electrode is placed on the third point. The at least one third counter electrode is placed in the vicinity of the third electrode, i.e, around the third point, but is placed sufficiently far away so that the third point is electrically biased at the voltage applied to the third active electrode. Each of the at least one third counterelectrode serves as a return path for the applied electrical current flowing from or into the third active electrode. For example, if the third electrode is placed on a vertebra in the spine, two third counterelectrodes can be placed at the right front side of the pelvis and at the left side of the pelvis (at left side and right side anterior superior iliac spine). The current density for the constant DC current flowing through the third point is preferably in the range from 25 $A/m^2$ to 38 $A/m^2$. Typical electrical current through the third active electrode that can provide such current density is from 5 mA to 30 mA, and typically from 10 mA to 20 mA, but the current depends on the human size, fat, and on the electrode size.

In each of the above embodiments, a set of synchronized applied electrical stimulation signals is applied to a first point in proximity to a first neural component at one end of a neural pathway of interest and to a second point in proximity to a second neural component at the other end of the neural pathway of interest. Two induced neural signals are generated and arrive at a neural communication impairment point in the neural pathway, thereby triggering and stimulating a neural rehabilitation process by which the neural connection between the first and second neural components is improved. Thus, the present invention may employ electrical stimulation at a neural communication impairment point at which the condition of neural communication impairment is physiologically embodied. A first neural element is the end portion of a first functional part of the neural pathway on one side of the neural communication impairment point. A second neural element is the end portion of a second functional part of the neural pathway on the other side of the neural communication impairment point. The first neural element is functionally connected to the first neural component, and the second neural element is functionally connected to the second neural component. The neural communication impairment point is located between the first element and the second element, and represents the region in which the neural communication is ineffective prior to treatment.

In both the iCENS mode and the aCENS mode, the first neural component responds to the applied electrical stimulation by generating a first neural signal, which is referred to as a first neural handshake signal. The first neural handshake signal which travels from the first neural component along a neural signal path toward the neural communication impairment point. Likewise, the second neural component responds to the applied electrical stimulation by generating a second neural signal, which is herein referred to as a second neural handshake signal. The second neural handshake signal travels from the second neural component along another neural signal path toward the neural communication impairment point. It is not necessary that each of the first and second neural components is functional provided that it is possible to generate a neural signal propagating from each of the first and second neural components to the neural communication impairment point.

Referring back to FIG. 25A, a signal monitoring means can be employed in any aCENS configuration. The signal monitoring means is configured to detect a handshake of the first periodic neural signals and the second periodic neural signals at a point in the neural pathway. For example, an oscilloscope or any other signal capturing electronic device can be wired to enable detection of a voltage signal or a current signal at the point in the neural pathway, which can be a neural pathway trigger site.

In general, a first means for inducing a first neural handshake signal and a second means for inducing a second neural handshake signal are provided in the aCENS mode. The first means is configured to supply a first applied stimulation signal to a first neural component of a neural pathway of interest. The first applied stimulation signal includes a first set of signal pulses having a magnitude that induces the first neural component to issue the first neural handshake signal on the neural pathway. The second means configured to supply a second applied stimulation signal to a second neural component of the neural pathway of interest. The second applied stimulation signal includes a second set of signal pulses having a magnitude that induces the second neural component to issue the second neural handshake signal on the neural pathway contemporaneously with the first neural handshake signal. The neural pathway has a base charge potential prior to application of the first and second applied stimulation signals.

Further, a charging signal source is provided. The charging signal source is configured to apply a charging signal to a neural pathway trigger site while the first and second neural handshake signals are present in the neural pathway. The first and second neural handshake signals interact and increase neural responsiveness of the neural pathway. The increase in neural responsiveness is measurable as an improvement in a level of capability of the vertebrate being in regard to achieving an outcome that depends on a functional level of the neural pathway.

Figure 25B:
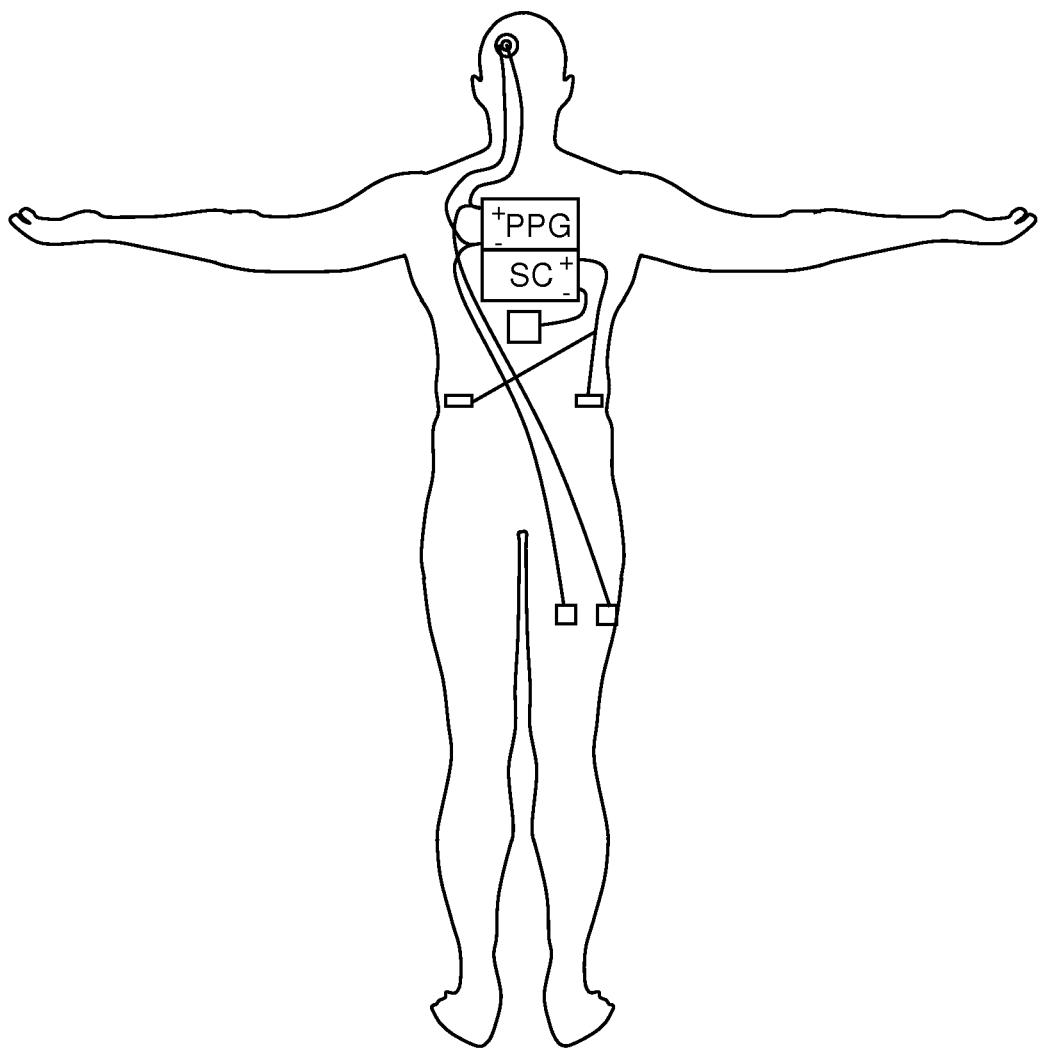
FIG. 25B is an illustration of a second exemplary electrode configuration for aCENS employing implantable or portable stimulation signal generators and charging signal generators.

In one embodiment, at least one of the first means and the second means is an implanted device that is temporarily or permanently implanted in the vertebrate being or a portable device carried by the vertebrate being. FIG. 25B illustrates a second exemplary electrode configuration for aCENS for the purpose of cortico-motor stimulation, in which the first means and the second means are integrated as a single implanted or portable device that is implanted, for example, on the backside skin, or carried on the clothing of the vertebrate being, if the vertebrate being is a human being. The single implanted or portable device can be a periodic pulse generator ("PPG") that generates synchronized electrical pulses to be applied across a pair of an active electrode and a reference electrode implanted on the body of a vertebrate being. The synchronized electrical pulses can have the type of waveforms as illustrated as "Signal 1" and "Signal 2" in FIG. 24. Further, the charging signal source can be embodied as an implanted or portable device including a series of batteries applying a constant positive output voltage and a constant negative output voltage. The periodic pulse generator and the charging signal source can be integrated as a single portable device, which can be mounted, for example, on the back of a person. Thus, a patient can be treated at a convenient time of her own choosing once the implanted or portable device is mounded on her, either temporarily or semi-permanently, i.e., permanently until removal.

The first neural signal is generated by the first neural component in response to the applied electrical stimulation applied to the first point, and is not a resistive electromechanical response of the body to the applied electrical stimulation. Thus, the first neural signal is an induced neural response, i.e., an induced neural signal, of the first neural component to the applied electrical stimulation, and as such, is delayed in time, and has a different waveform, from the applied electrical stimulation. Likewise, the second neural signal is generated by the second neural component in response to the applied electrical stimulation applied to the second point, and is not a resistive electromechanical response of the body to the applied electrical stimulation. Thus, the second neural signal is an induced neural response, i.e., an induced neural signal, of the second neural component to the applied electrical stimulation, and as such, is delayed in time, and has a different waveform, from the applied electrical stimulation.

The delay in time between the applied electrical stimulation and the first or second neural signal is typically from 10 milliseconds to 50 milliseconds, and depends on the type of the cell or cells which constitute the first neural component or the second neural component. Typically, a delay between 10 milliseconds and 30 milliseconds between the applied electrical stimulation and an induced neural signal has been observed for human cortex neurons, and a delay between 20 milliseconds and 50 milliseconds between the applied electrical stimulation and an induced neural signal has been observed for human lower motoneurons. The delay time between the applied electrical stimulation and an induced neural signal is herein referred to as "induced signal generation delay time."

The first signal and the second signal arrive at the neural communication impairment point within tens of milliseconds after simultaneous application of applied electrical stimulation to the first point and the second point. Because the induced signal generation delay time depends on the type of cell or cells that constitute the first or second neural component, the two induced neural signals may not arrive at the neural communication impairment point simultaneously, but the induced signals arrive with an overlap in time, i.e., contemporaneously. For example, if one of the first and second neural components is a cortex neuron and the other of the first and second neural components is a lower motoneuron, the leading edge of the induced neural signal from the cortex neuron typically arrives at the neural communication impairment point earlier than the leading edge of the other induced neural signal from the lower motoneuron. If both the first and second neural components are cortex neurons, the leading edge of the induced neural signal from a cortex neuron may arrive at the neural communication impairment point simultaneously with, or with a difference in arrival time relative to, the leading edge of the other induced neural signal from the other cortex neuron depending on the types of cortex neuron involved therein. If one of the first and second neural components is a cortex neuron and the other of the first and second neural components is a sensory neuron, there may be a difference between arrival times of two leading edges of the induced neural signals from the cortex neuron and the sensory neuron.

In all cases, the earlier arriving signal lasts long enough to overlap with the leading edge of the later arriving signal, i.e., the first induced neural signal from the first neural component and the second induced neural signal from the second neural component arriving at the neural communication impairment point overlap in time because the duration of each induced neural signal typically lasts at least 15 milliseconds. Two induced neural signals that arrive at the neural communication impairment point are thus contemporaneous, i.e., there is a non-zero overlapping time period between the two neural signals. The phenomenon of the convergence of, and the spatial and temporal overlap of, the two neural handshake signals at the neural communication impairment point provides a "handshake," which has the effect of rehabilitating the neural communication impairment point.

Figure 26:
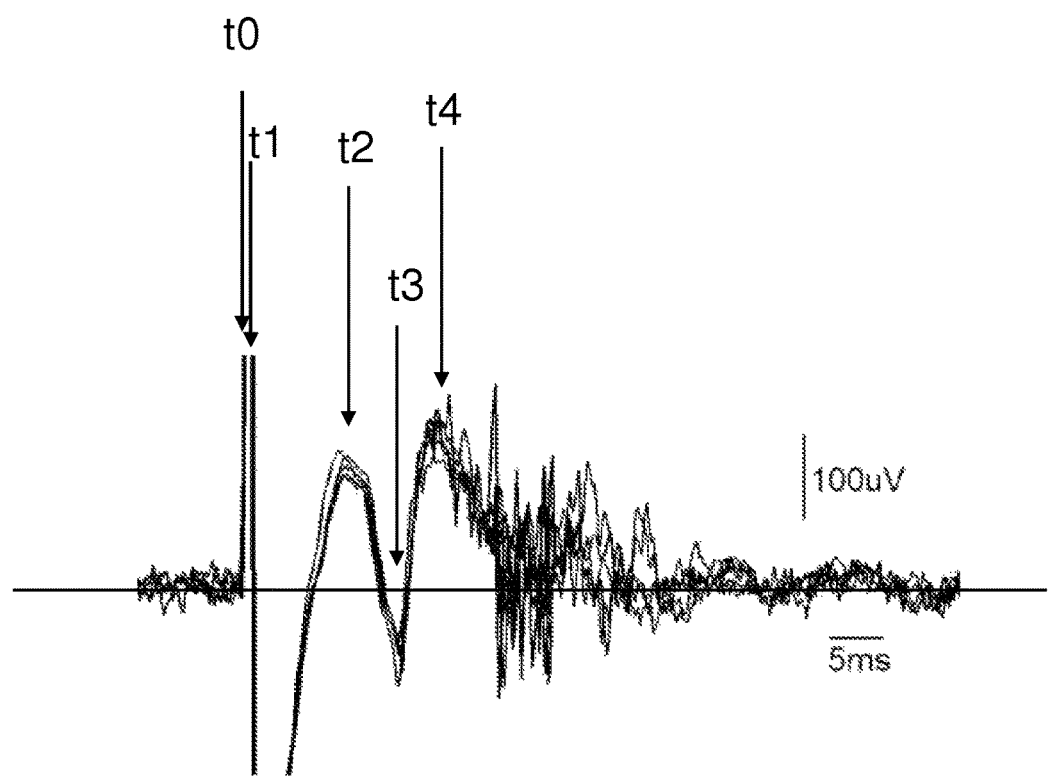
FIG. 26 is a graph illustrating an electrical response at a neural communication impairment point.

Referring to FIG. 26, the phenomenon of a handshake is graphically illustrated in a graph illustrating an electrical response at a neural communication impairment point. The horizontal axis represents time, and the vertical axis represents the electrical voltage at the neural communication impairment point of a mouse with a spinal injury. The configuration employed is illustrated in FIG. 1A and explained below in the section below titled FIRST EXPERIMENT (EMPLOYING iCENS). The neural communication impairment point in this case is the vertebra at which the spinal cord injury is present. While the negative voltage output (ranging from −1.8 to −2.6V) was delivered to the muscle (two-wire electrode, 500 µm), the positive output (ranging from +2.4 to +3.2V) was delivered to the primary motor cortex (M1) (electrode tip, 100 µm). In this setup, the first neural component is the neurons in the primary motor cortex of the mouse, and the second neural component is the lower motoneurons in the muscle of the mouse. Responses to six pulses of 400 microsecond duration at a frequency of 1 Hz were captured using an oscilloscope configured to capture the voltage at the injured spinal cord employing the pulses as the capture-triggering signal.

The rising edges of the pulses have been aligned to t0, which is herein referred to as the pulse initiation time. A first neural handshake signal is generated from the neurons at the primary motor cortex, and a second neural handshake signal is generated from the lower motoneurons in the muscle. In this case, the delay between the simultaneous application of the electrical pulses (i.e., the synchronous rising edges of the electrical pulses) and the generation of the first neural handshake signal is less than the delay between application of the electrical pulses and the generation of the second neural handshake signal. Thus, the first neural handshake signal arrived at the injured spinal cord earlier in time than the second neural handshake signal in each of the six captured voltage profile.

The falling edges of the pulses occur at t1, which is 400 microseconds after t0 for each pulse. The switching on and off of the electrical pulses perturbs the voltage at the injured spinal cord, for example, by electrical current that passes through various parts of the body, thereby introducing transient spurious signals that does not accurately represent the voltage at the injured spinal cord. As the transient spurious signals dissipate after a pulse is turned off at the time corresponding to t1, the measured data represents the voltage at the injured spinal cord accurately. Thus, while it is difficult the precise timing of the arrival of the leading edge of the first neural handshake signal at the injured spinal cord, the leading edge of the first neural handshake signal occurs at a time earlier than t2, which represents the time at which the first neural handshake signal has a peak intensity. The peak of the first neural handshake signal occurs at about 12.5 milliseconds after t0.

The first neural handshake signal has a waveform that includes attenuating oscillations in voltage as a function of time. In this case, before the first handshake signal makes a full negative swing following the first positive swing (with the peak that occurs at t2), a leading edge of the second neural handshake signal from the lower motoneuron arrives at the injured spinal cord at a time t3. Since the measured voltage at the spinal cord is a superposition of the two voltages representing the first neural handshake signal and the second neural handshake signal, the slope of the voltage changes abruptly at t3 when the leading edge of the second neural handshake signal arrives as illustrated in FIG. 26. The peak of the second neural handshake signal occurs at or in proximity to t4.

The second neural handshake signal arrives at the neural communication impairment point, i.e., the injured spinal cord, before all of the attenuating oscillations of the first neural handshake signal die out in time. Thus, the first neural handshake signal and the second neural handshake signal propagate toward, and converge and meet at, the neural communication impairment point. The first neural handshake signal and the second neural handshake signal arrive at the neural communication impairment point from two opposite sides, and overlap temporally and spatially at the neural communication impairment point, thereby performing a handshake of the two induced neural signals. This phenomenon is also referred to as "signal coincident" or "coincidence." The temporally overlapping aspect of the two signals, i.e., the fact that there exists a finite time period in which the duration of the first neural handshake signal and the duration of the first neural handshake signal, is characterized as being contemporaneous Because induced neural signals do not last forever, simultaneous application of applied signals is a significant contributing factor for providing a handshake. In general, it is necessary to provide a handshake at the neural communication impairment point. As illustrated in FIG. 26, the typical duration of induced neural signals is on the order of tens of milliseconds. In practical terms, induced neural signals are most effective for the first 30 milliseconds or so after generation. Even after factoring in a time delay of about 20 milliseconds between application of external stimulus applied to the first and second neural components and generation of the induced neural signals, typical handshakes are initiated in a range from about 20 milliseconds to 40 milliseconds, and last for a duration less than 100 milliseconds, and typically for less than 50 milliseconds before the signal intensity falls within the noise level.

Thus, while it is in principle possible to provide a handshake with insignificant offset in time between a first applied stimulation applied to the first neural component and a second applied stimulation applied to the second neural component, experimental data has shown that simultaneous application of the first and second applied stimulations provides good handshakes and the most effective result so far. If a charging signal, i.e, a third applied stimulation signal, is employed as in the aCENS embodiment, it is preferred that the charging signal is applied simultaneously with the first and second applied stimulation signals. Simultaneous application of the first, second, and optionally the third applied stimulation signal can be effected by synchronizing these signals, for example, by providing these signals from a common power supply source or by electronically synchronized multiple power supply sources.

The handshake induces a biological repair process at the neural communication impairment point. During the biological repair process, structures of cells are modified to establish a functional neural connection between the first neural element and the second neural element. The modification of the cells may proceed in the form of structural change in preexisting cells, or may involve generation and/or growth of new cells. Thus, the biological repair process induces a permanent change in the structure of the neural communication impairment point such that sufficient functional neural connection between the first neural component and the second neural component. This permanent change in the structure of the neural communication impairment point and the accompanying improvement in the functional neural connection can be so substantial that the condition of the neural communication impairment is substantially or completely eliminated.

In general, the methods of embodiments of the present invention can be employed to induce the biological repair process that transforms a neural communication impairment point into a neural communication rehabilitation point by partially or fully removing the condition of the neural communication impairment by simultaneous application of external electrical signals that generate induced neural signals, which then propagate along neural paths to meet at the neural communication impairment point and to stimulate the cell structure around the neural communication impairment point to initiate a rehabilitation process.

In one embodiment, the neural communication impairment can be trauma-induced neural communication impairment or genetic post-birth neural communication impairment, and the rehabilitation process can be a repair process that restores the physical property and configuration of the neural communication impairment point to a functional state that existed prior to generation of the neural communication impairment, for example, by external physical trauma or a neurological disease. An example of external physical trauma is spinal injury. Examples of a neurological disease include Lyme disease and leprosy. Alternately, if the rehabilitation process can be a process of augmentation/reinforcement of a non-functional or minimally functional neural path. In this case, the physical property and configuration of the neural communication impairment point is altered to augment or reinforce a weak or non-functional neural signal path through or around damaged neural connection.

In another embodiment, the neural communication impairment can any of ab initio neural communication impairment, be trauma-induced neural communication impairment, and genetic post-birth neural communication impairment, and the rehabilitation process can be a process of generation of an alternative neural path. In this case, the physical property and configuration of the neural communication impairment point is altered to form a substitute neural signal path through or around damaged neural connection where none existed before.

In general, existing cells are modified and/or new cells are formed at the neural communication impairment point upon stimulation by two contemporaneous neural signals through the applied electrical stimulation such that the neural communication between the first neural component and the second neural component is formed with sufficient strength, durability, and functionality. Thus, two weakly linked or non-linked neural elements become neurally connected and form a new functional neural communication path segment through which neural signals can flow. The combination of the existing functional neural communication path and the new functional neural communication path segment provides a functional neural signal path between the first neural component and the second functional component, thereby removing or alleviating the disability cause by the neural communication impairment, and transforming the neural communication impairment into a neural communication rehabilitation point.

Upon transformation of the neural communication impairment point into the neural communication rehabilitation point, the neural signal from a first neural component can effectively pass a neural signal through the neural communication rehabilitation point to the second neural component. A weak signal path segment in the neural communication impairment point can be revitalized or reinvigorated during the transformation to provide a functional neural connection between the first neural element and the second neural element in the neural communication rehabilitation point. Alternately, a signal path segment that did not exist in the neural communication impairment point can be formed in the neural communication rehabilitation point to provide a functional neural connection between the first neural element and the second neural element.

The result of the transformation of the neural communication impairment point into the neural communication rehabilitation point is a permanent enhancement in the effectiveness of transmission of a neural signal from the first neural component to the second neural component. Thus, the second neural component becomes more sensitive to a neural signal that the first neural component. In other words, the effectiveness of a neural signal from the first neural component on the second neural component is permanently amplified by the transformation of cell structures in the neural communication rehabilitation point.

In another perspective, during the treatment of the neural communication impairment point, the first neural component and the second neural component are externally stimulated to simultaneously generate action potential, i.e., the axons attached to the first neural component and the second neural components are artificially and externally induced to "fire" neural signals. The first neural signal from the first neural component and the second neural signal from the second neural component travel through functional portions of the neural communication pathway to contemporaneously meet at the neural communication impairment point, which can be a dysfunctional spinal cord or a dysfunctional portion of the neural path in the torso or limbs or even in a portion of the cortex. The contemporaneous arrival of the induced neural signals triggers the process of rehabilitation.

Various types of rehabilitation can occur depending on embodiments. In the first embodiment, the rehabilitation method of the present disclosure can enable a vertebrate being to use a limb, or strengthen the use of a minimally operational limb, by repair or reinforcement of a disrupted portion of the cortico-neuromuscular pathway. Thus, a lower motoneuron designed to actuate a muscle can perform the original function the lower motoneuron is designed to perform under the control of a cortex neuron that is designed to control that lower motoneuron.

It is noted that in many cases two neural pathways are present for actuation of a muscle in a vertebrate being. The first neural pathway is a cortico-neuromuscular pathway that transports a neural signal from a motor cortex to a lower motoneuron. The second neural pathway is a sensory-cortico pathway that transports a neural signal from a sensory neuron to a sensory cortex. The neural communication impairment point is present in the first neural pathway, but not in the second pathway in the first embodiment. Thus, the operation of the second neural pathway indirectly helps establish positive feedback loop in conjunction with the stimulation of the neural communication impairment point located within the first neural pathway, but the transmission and of the induced neural signals in the first neural pathway, which is a cortico-neuromuscular pathway.

In a normally functioning cortico-neuromuscular pathway, the neural signals travel only one way, viz., from the motor cortex to the lower motoneuron. During the treatment, the neural signal that originates from the second neural component travels in the opposite direction of normal signal transmission in a functioning cortico-neuromuscular pathway. The applied electrical stimulation applied to the second neural component triggers this flow of neural signal in the reverse direction up to the neural communication impairment point.

In the second embodiment, the rehabilitation method of the present disclosure can rehabilitate intra-brain neural connections, i.e., enable neural communication between a first neuron located in a first portion of a cortex and the second neural component is a second neuron located in a second portion of the same cortex or in a portion of a different cortex. The neural communication between two cortex neurons can be enhanced in the second embodiment to alleviate or remove the neural communication impairment between the two cortex neurons or between functionally related sets of neurons scattered among at least two different cortex regions or among multiple cortexes. For example, in the case of treatment of autistic disorder, the signal applied to the frontal lobe and the parietal lobe may generate or rehabilitate associated neural pathways.

In the third embodiment, a sensory-cortico neural connection may be restored to enable sensing of visual, auditory, or thermal sensing or other types of sensing relating to pressure, taste, smell, movement or actuation of a body muscle. For example, the condition of cortical blindness can be rehabilitated to restore vision, or the condition of tinnitis can be restored to restore hearing. Other sensory impairment may be rehabilitated to remove the associated disability by the transformation of a neural communication impairment point to a neural communication rehabilitation point employing the methods disclosed herein.

The mechanism by which the contemporaneous arrival of neural signals at a neural communications impairment point initiates and/or stimulates the physiological change in the cell structure at the neural communications impairment point is currently not clearly understood. It is conjectured, however, that the repeated stimulation of the cell structure by the contemporaneously arriving neural signals from two functionally related neural components initiates, stimulates, and/or fosters the regeneration or regrowth of neural structures that subsequently mature into a functioning neural signal segment that is functionally coupled to existing neural signal paths. It is conceivable that the regeneration or regrowth of neural structures may proceed from only one of the first neural element and the second neural element, or from both of the first neural element and the second neural element, or from a cell structure that is not part of the first or second neural element. Further, it is conjectured that repetition of the contemporaneous arrival of neural signals at the neural communications impairment point has the effect of facilitating the regeneration or regrowth of neural structures by reinforcing the validity of the neural connection, allowing a neuron in a cortex to learn and validate the newly acquired neural connection with another lower motoneuron, another neuron in a different cortex, or a sensory neuron. It is also conjectured that the contemporaneous arrival of neural signals facilitates may release of a neurotransmitter at the neural communications impairment point and/or stimulates or otherwise activates a dormant chemical receptors. Thus, by enhancing the functionality of neuron in releasing neurotransmitters and/or receiving neurotransmitters, the weakened, dormant, or non-existent neural connection may be repaired and/or enhanced to a functional level.

Typically, repeated or habitual use of a neural system helps each component in the neural system to stay functional. For example, routine neural communication between a neuron in a motor cortex and a functionally related motoneuron that is controlled by the neuron reinforces the validity of this neural pathway by a positive feedback signal generated by a sensory neuron that reports the movement of muscle actuated by the functionally related motoneuron to another neuron in the motor cortex. Similarly, routine neural communication between a first neuron in a first portion of a cortex and a second neuron in a second portion of the same or different cortex reinforces the validity of this neural pathway by a positive feedback signal generated by the second neuron or any other neuron that is functionally related to, or is activated by, the second neuron and received by the first neuron or another neuron in the first cortex. Likewise, routine neural communication between a sensory neuron and a neuron in a cortex, which can be, for example, visual input or aural input or sensory input, reinforces the validity of this neural pathway by a positive feedback signal generated by the same neuron or any other neuron within the same cortex, for example, by a brain activity that interprets the image, the sound, or other sensory perception.

Trauma can cause injury to a neural communication pathway, for example, in the form of a spinal injury, disturbance or weakening of communications between different cortexes by injury or genetic causes, or an injury or degradation of any cells or structures employed to convey a neural signal from a sensory neuron to a neuron in a cortex. Such a trauma thus generates a neural communication impairment point, and puts all or the majority of components employed for neural communication into the state of inactivity. Prolonged inactivity in the components of the neural communication pathway, which include the first neural component and the second neural component and any other neural component that was once used to convey neural signals therebetween, weakens the components of the neural communication system. As time goes on, lack of use of the components of the neural communication system causes further deterioration of the neural connection in the neural communication pathway. This vicious cycle of lack of use and component degradation can keep additional components in the neural communication pathway dysfunctional, thereby increasing the degree of dysfunction in the neural communication system.

The methods in the embodiments of the present invention reverse this cycle by initiating a positive and constructive cycle of use and positive feedback in the neural communication pathway. To initiate this positive cycle, applied electrical stimulation is employed to induce neural signals, which travel along functional portions of the neural pathway and contemporaneous arrive at a neural communications impairment point. The activity at the first neural element and the second neural element is positively correlated as the brain recognizes, and positively correlates, the neural signal activities occurring at the first and second neural components and the electrical pathway therebetween and other contemporaneous sensory perceptions such as movement of a muscle or any other sensory activity that may occur concurrently, e.g., in the form of a visual signal, an aural signal, or any other activity in the body that may be induced to enhance the association between the neural activity and motor activity, cognitive activity, or sensory activity.

Thus, the components of a neural pathway is "reactivated," "energized," "excited," or "revived" by the induced neural signals, which are generated by the applied electrical stimulation, from the state of inactivity. Such reactivation, energizing, excitation, or revival of the unused components of the neural pathway has the effect of initiating "retraining" of the dysfunctional part of the neural pathway. Once the neural communication impairment point is transformed into a neural communication rehabilitation point, the entire neural pathway from the first neural component to the second neural component is repaired. Often, any functionally related neural pathway, which provides the feedback to the brain based on the activity in the first and second neural components, is also restored to fully operational state.

As illustrated above, multiple neural pathways can be stimulated simultaneously or alternately in typical treatment sessions. For example, a quadriplegic patient may be stimulated at a first neural pathway between a right side motor cortex and neurons at a muscle on the left side of the body, and may be simultaneously and/or alternately stimulated at a second neural pathway between a left side motor cortex and neurons at a muscle on the right side of the body.

Further, additional neural pathways may be added and stimulated simultaneously or alternately with stimulation of such multiple neural pathways. For example, a quadriplegic patient may be stimulated, either simultaneously or in rotation, at a first neural pathway between a right side motor cortex and neurons at a muscle on the left arm, a second neural pathway between the right side motor cortex and neurons at a muscle on the left leg, a third neural pathway between a left side motor cortex and neurons at a muscle on the right arm, a fourth neural pathway between the right side motor cortex and neurons at a muscle on the right leg.

If aCENS is employed, a charging signal can be applied to one or more parts of the body of the vertebrate being at the same frequency as the first and second applied stimulation signals. In the example of the treatment of a quadriplegic patient, the charging signal may be applied to a spinal vertebra or multiple spinal vertebrae associated with movement of limbs.

In the case of treatment of sensory-cortico neural path for sensory impairments, the multiple stimulation signals can be simultaneously or alternately applied. As discussed above, such applied stimulation signals may be electrical signals, sonic stimulation signals, ultrasonic stimulation signals, magnetic stimulation signals (in which a steady state or dynamic magnetic field is applied), light stimulation signals, thermal stimulation signals (in which heat is applied), cryogenic stimulation signals (in which one or more neural element is subjected to exposure to a cold surface or a cold object), vibrational stimulation signals, pressure stimulation signals, vacuum suction stimulation signals, any other sensory signal, or a combination thereof.

Figure 27:
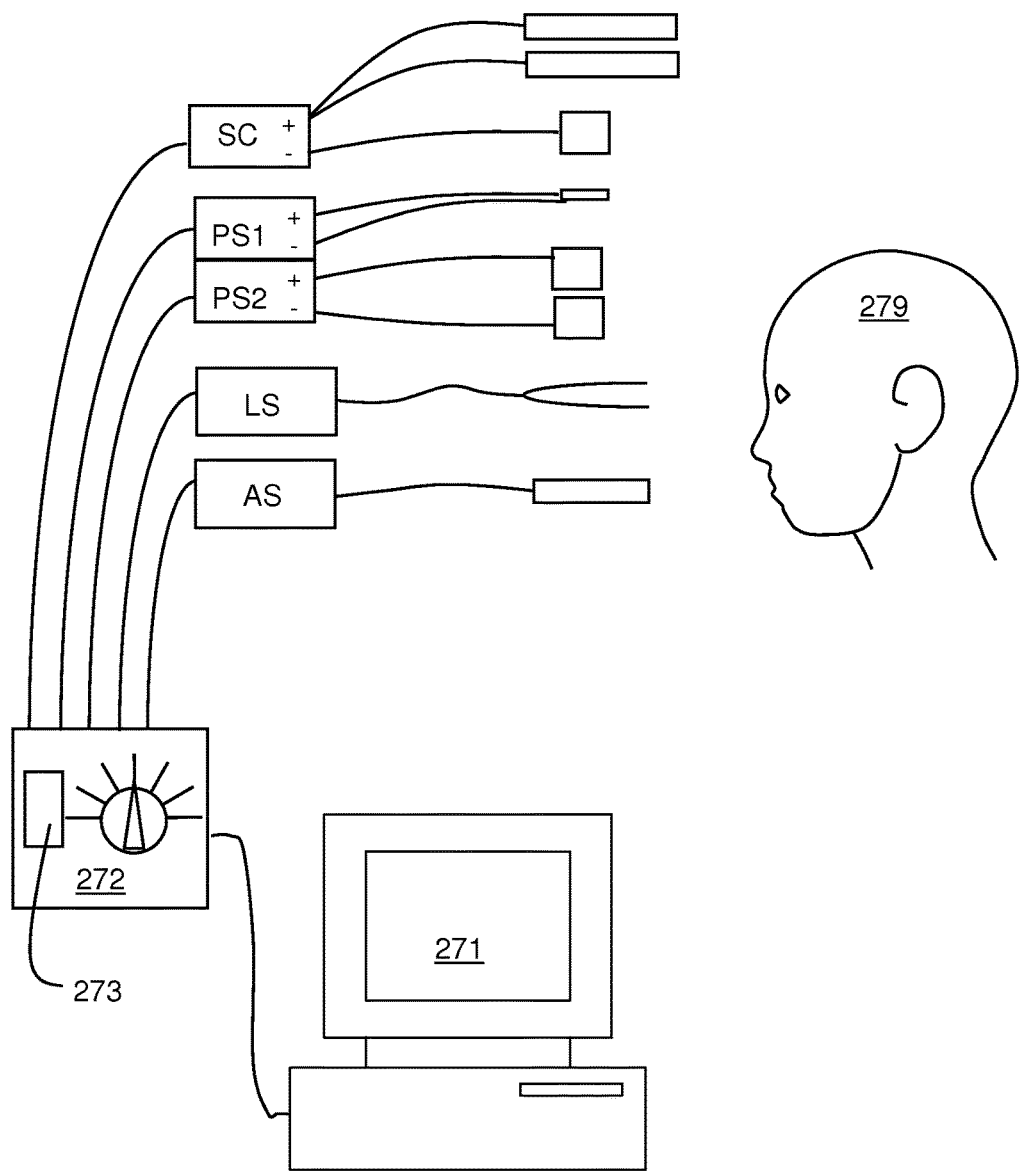
FIG. 27 is an illustration of an exemplary system for treating a neural pathway employing a computer and/or a signal characteristics selector.

Referring to FIG. 27, an exemplary system for treating a neural pathway is illustrated. The exemplary system employing a computer 271 and/or a signal characteristics selector 272. While the signal characteristic selector 272 is shown as a separate unit in FIG. 27, embodiments are also contemplated herein in which the signal characteristics selector 272 in incorporated into the computer 271 as signal interface cards specifically adapted to interface with various pulsed signal generating devices. Alternately, the exemplary system may be employed only with the computer 271 and without the signal characteristics selector 272, or only with the signal characteristics selector 272 without the computer 271. If the computer is present, the computer 271 can be configured to track the patient's information and automatically select the appropriate signal generating device(s) and/or display the parameters to be employed on any signal generating device to be used. The computer 271 can include a program that is configured to select treatment parameters, i.e., the parameters to be employed during each treatment session. For example, such treatment parameters may be determined based on the patient's height, weight, age, sex, sickness, disability level, overall health, athletic capacities, past medical history, and/or the level of desired treatment such as aggressive level high risk treatment or conservative low risk treatment. Further, the computer 271 may include programs that allow user-selectable setting of treatment parameters. Likewise, the signal characteristics selector 272 may have an analog or digital interface device such as a display screen 273.

Multiple stimulation signal generators are provided and interfaced with the signal characteristics selector 272 and/or the computer 271. The multiple stimulation signal generators can include, for example, a first electric pulse generator PS1, a second electric pulse generator PS2, a charging signal generator SC, a light pulse generator LS, an acoustic pulse generator AS, and/or any other type of pulses signal generator. The first electrical pulse generator PS1 can provide an electrical voltage signal, for example, across a first electrode and a second electrode in FIGS. 21A and 22A or across a first active electrode and a first reference electrode in FIG. 25A. The second electric pulse generator PS2 can provide an electrical voltage signal, for example, across another first electrode and another second electrode in FIGS. 21A, 22A, 23A, and 23C or across a second active electrode and a second reference electrode in FIG. 25A. The charging signal generator SC can provide a charging signal across a third active electrode and at least one counter electrode, for example, as in FIG. 25A. Further, the light pulse generator LC can provide pulsed illumination designed to reach an optical nerve, for example, in the configuration of FIG. 23A in addition to, or in lieu of, the electrical stimulation provided to the optical nerves. The acoustic pulse generator can provide pulse acoustic wave signals designed to reach an auditory nerve, for example, in the configuration of FIG. 23C in addition to, or in lieu of, the electrical stimulation provided to the auditory nerves. Thus, the characteristics of pulsed signals to the applied to a vertebrate being 279 can be selected depending on the type of treatment to be performed.

The signal characteristics selector 272 can be used to select characteristics of the first and second applied stimulation signals and/or the charging signal in the various embodiments described above. The signal type selector includes an input device for identifying at least one of a type of the neural pathway of interest and a type of the outcome. For example, the type of neural pathway may include a cortico-neuromuscular pathway, an inter-cortex (intra-brain) pathway, or a sensory-cortico pathway. The three types of neural pathways may be further classified into further subtypes of neural pathways, each with associated signal type to be employed. The type of outcome may be selected based on the type of disability under treatment, the length of the session, and the degree of treatment, e.g., an aggressive treatment or a conservative treatment. Further, the input device can be configured to adjust the first and second applied stimulation signals and/or the charging signal according to an input to the input device and selected from predetermined menu of signal characteristics. The input device may be rotary selector knob, a touchscreen with predetermined menus, a keyboard, and/or a mouse.

The computer 271 can be configured to synchronize application of the first and second stimulation signals. The computer can include a program for determining an optimal signal magnitude by gradually increasing a magnitude of at least one test signal applied to the first and second points. The optimal signal magnitude is set at a signal magnitude at which a muscle associated with the first or second neural element begins to react to the at least one test signal, for example, by twitching.

In one embodiment, the computer can be configured track the progress of treatment sessions. Thus, the first and second applied stimulation signals can be provide, for example, as signal pulses repeated at least 20 times and at most 100,000 times.

The first and second stimulation signal can be selected from any signal available from the attached stimulation signal generators, which can generater an electrical voltage signal, a sonic stimulation signal, an ultrasonic stimulation signal, a magnetic stimulation signal in which a steady state or dynamic magnetic field is applied, a light stimulation signal, a thermal stimulation signal, a cryogenic stimulation signal, a vibrational stimulation signal, a pressure stimulation signal, a vacuum suction stimulation signal, and any other sensory signal capable of sensed by a vertebrate being. If one of the first and second stimulation signal is an electrical voltage signal, and the other of the first and second stimulation signal can be selected from a sonic stimulation signal, an ultrasonic stimulation signal, a magnetic stimulation signal in which a steady state or dynamic magnetic field is applied, a light stimulation signal, a thermal stimulation signal, a cryogenic stimulation signal, a vibrational stimulation signal, a pressure stimulation signal, a vacuum suction stimulation signal, and any other sensory signal capable of sensed by a vertebrate being.

The duration of each pulse and the frequency of the pulsed signals can be selected based on the patient information and the type of treatment. Typically, the first and second stimulation signals have a frequency that does not exceed 100 Hz, and the periodic pulses have a duration from 40 microseconds to 10 milliseconds.

An Example of Inherent Charge-Enhanced Neural Stimulation (iCENS) Mode

In one embodiment of the present invention, inherent charge-enhanced neural stimulation mode (iCENS) can be employed to rehabilitate a neural pathway between a first neural component and a second neural component. As discussed above, the first neural component and the second neural component can be in any of the following three combinations:
  a. a cortex neuron for the first neural component and a lower motoneuron for the second neural component;
  b. a first cortex neuron for the first neural component and a second cortex neuron for the second neural component; and
  c. a sensory neuron for the first neural component and a cortex neuron for the second neural component.

The method of dipolar neural stimulation as applied to a neural communication path between a cortex and a lower motoneuron is referred to as dipole cortico-muscular stimulation (dCMS).

The application of dCMS results in a remarkable enhancement of the excitability of the motor pathway. This enhancement was observed in both animals and humans. In control animals and in SCI animals, which had severe locomotor impairment associated with signs of spastic syndrome, the effect was observed both in the ipsilateral and contralateral pathways. Maximal threshold of the ipsilateral cortex was reduced. Improvement in muscle strength was accompanied by an increase in spontaneous activity and potentiation of evoked responses of the spinal motoneurons. Spinal motoneuronal responses and muscle twitches evoked by stimulation of the contralateral, non-treated M1 (motor cortex) were significantly enhanced as well. The dCMS-induced effect persisted beyond the phase of stimulation and extended through the entire period of the experiment as explained in detail further below.

The electrodes may be attached topically on the surface, or underneath the skin, or surgically implanted. In one embodiment, an active electrode is situated on the motor cortex (first point) and a reference electrode is situated on the desired muscle (second point), allowing the current to travel across the spinal cord. In another embodiment, an active electrode is situated on the desired muscle (first point) and a reference electrode is situated on the motor cortex (second point), again allowing the current to travel across the spinal cord. In yet another embodiment, neither the active electrode nor the reference electrode is placed on the motor cortex. Instead, both the active electrode and reference electrode are placed on desired first and second point muscles, which are on opposite sides of the body, allowing the current to travel across the spinal cord.

Figure 10:
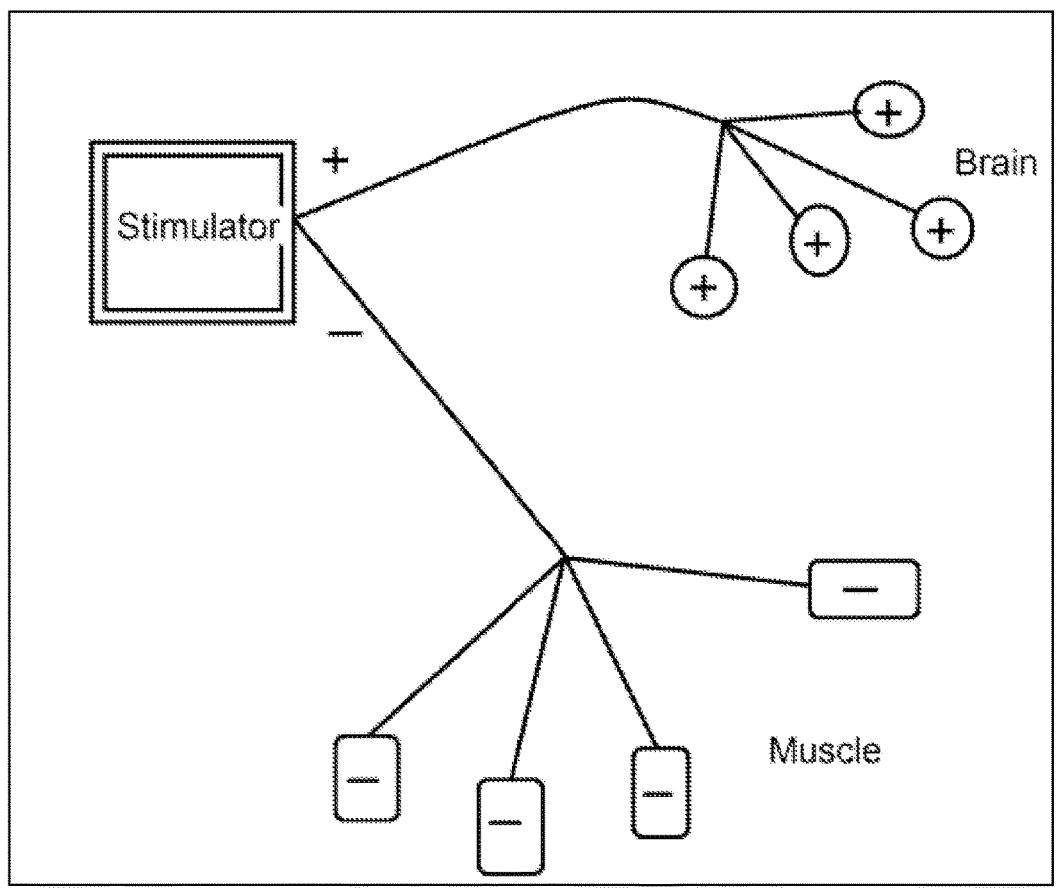
FIG. 10 is a first configuration of a simulator and a plurality of active electrodes (labeled "+") and a plurality of reference electrodes (labeled "−").

In one embodiment of the present disclosure, a dipolar cortico-muscular stimulator can be employed to provide electrical pulses for the purposes of the present disclosure. FIG. 10 illustrates an exemplary connection scheme employing a dipolar cortico-muscular stimulator. A dipolar cortico-muscular stimulator can include a stimulator box with a LCD Display or computer connections to a software control system. In a non-limiting illustrative example, a dipolar cortico-muscular stimulator having the following configuration can be employed:
- Pulse Type: Constant current
- Wave form: Rectangular
- Pulse duration 0.5 to 5 ms
- Pulse amplitude 1 to 50 mA (Voltages at 1 to 35V)
- Frequency range 0.05 to 100 Hz
- Inherent Safety/shutdown features to prevent over stimulation The outputs are connected in a way that makes the stimulus intensity to be the difference between the voltages at the positive and negative outputs. The regulations of both outputs are synchronized to make the absolute value of the difference between these two outputs always the same. Thus, when the positive output increases the negative output should decrease the same amount. For example, when the positive output is increased from +4 V to +5 V, the negative output decreases from −1 V to 0 V.

Digital-to-analog converter (DAC) can be used to provide analog output, i.e., stimulation, through analog outputs of the stimulator box. The DACs can produce constant DC voltage levels or waveforms under software control. The output of the DACs may be fed through a programmable attenuation network to produce different output ranges. The signal may be then split into a positive and negative output through buffer amplifiers.

Optionally, each of the electrode wires can be split and connected to multiple locations. For example, active electrode can be split into multiple wires each with its own electrode. This is important in human application in case more areas needed to be stimulated. For example, at the cortex, an operator can use only one active electrode for focal stimulation or two active electrodes for more broad but less painful stimulation. Also, at the muscle, the operator can include more parts of the limb in the same session. Individual electrode size should be about 5 cm$^2$.

This system can be employed to improve a neuromuscular condition of the vertebrate being. The at least one active electrode is placed at, or in proximity to, a first point. The at least one reference electrode is placed at, or in proximity to, a second point. As discussed above, each of the first point is located on one side of a spinal column of a vertebrate being, and each of the second point is located on the opposite side of the spinal column. Each location of the first point and the second point can be independently selected from the motor cortex and a muscle of the vertebrate being. Each muscle includes at least one nerve. Electrical current is passed between the at least one active electrode and the second electrode. At least one path of the electrical current runs across the spinal column and between the first point and the second point.

In one embodiment, one of the at least one active electrode and the at least one reference electrode can be sized and configured to be placed at, or in proximity to, the motor cortex. Such an electrode can be sized and configured to be placed at, or in proximity to, the motor cortex of a mammal having limbs or the motor cortex of a human. The at least one active electrode and the at least one reference electrode can be placed on the vertebrate being such that the at least one path of the electrical current includes a motor pathway between the motor cortex and a muscle. The first point can be a point at the motor cortex and one of the second point can be a point at a muscle. Alternatively, the second point can be a point at the motor cortex and the first point can be a point at a muscle.

In another embodiment, all of the at least one active electrode and the at least one reference electrode can be sized and configured to be placed at, or in proximity to, a muscle of the vertebrate being. Thus, all of the at least one active electrode and the at least one reference electrode can be sized and configured to be placed at, or in proximity to, a muscle in a limb of a mammal having limbs or a human limb. The at least one active electrode and the at least one reference electrode can be placed on the vertebrate being such that the first point is a point at a first muscle, and the second point is a point at a second muscle. The at least one path of the electrical current can include at least one first lower motoneuron connected to the first point and at least one second lower motoneuron connected to the second point.

Figure 11:
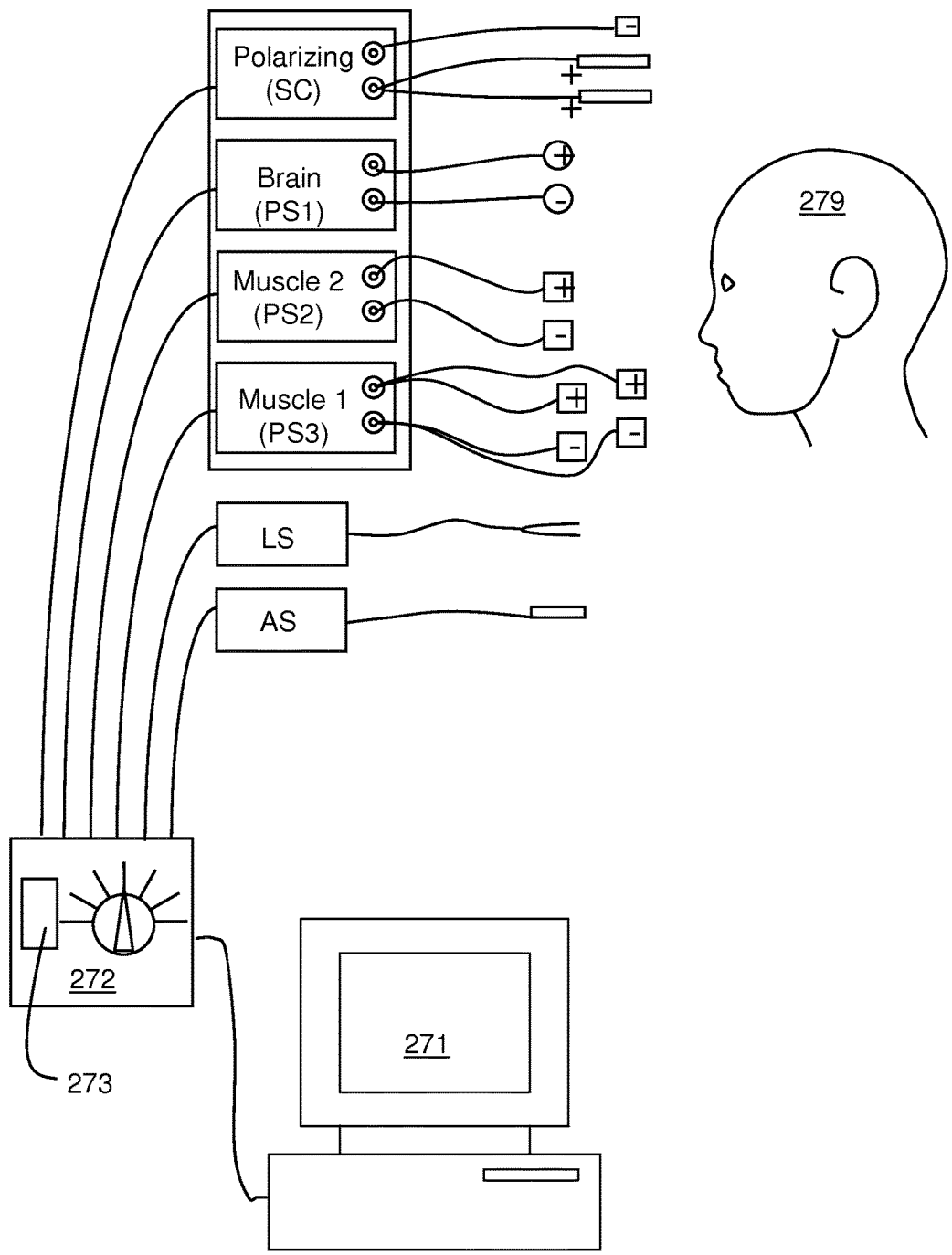
FIG. 11 is a second configuration of a simulator including multiple simulator units and electrodes attached thereto.

The at least one active electrode can be a single active electrode, and the at least one reference electrode can be a single reference electrode as illustrated in FIG. 1A. Alternatively, the at least one active electrode can be a plurality of active electrodes and/or the at least one reference electrode can be a plurality of reference electrodes as illustrated in FIGS. 10 and 11.

If multiple electrodes are employed for either the at least one active electrode or the at least one reference electrode, the multiple electrodes can be placed at, or in proximity with, the same muscle. For example, a plurality of first electrodes can be placed at, or in proximity with, the motor cortex, and a plurality of second electrodes can be placed at, or in proximity with, a muscle. Further, a plurality of first electrodes can be placed at, or in proximity with, a first muscle, and a plurality of second electrodes can be placed at, or in proximity with, a second muscle that is different from the first muscle. In each of the examples above, the at least one active electrode can be the plurality of first electrodes and the at least one reference electrode can be the plurality of second electrodes, or vice versa.

Each of the at least one active electrode and the at least one reference electrode can be configured for attachment to the motor cortex or a muscle of the vertebrate being by any method, and particularly, topically, underneath a skin, and/or by surgical implantation. In this case, the method of the present disclosure can include attaching each of the at least one active electrode and the at least one reference electrode to the motor cortex or a muscle of the vertebrate being topically, underneath a skin, and/or by surgical implantation.

In still yet another embodiment, the system can include at least one probe for identifying a lower motoneuron that affects movement of a muscle of the vertebrate being and located in the spinal column by applying electrical voltage thereto. An example of such at least one probe is the pair of pure iridium microelectrodes illustrated in FIG. 1A and labeled as "Rec." If provided, the at least one probe can be employed to identifying a lower motoneuron that affects movement of a muscle of the vertebrate being in the spinal column. The muscle is subsequently attached to an active electrode or a reference electrode. The at least one probe can be employed to determine a maximal stimulus strength for the lower motoneuron at which no further increase in muscle contraction of the muscle is observed with an increase in strength of electrical stimulation to the lower motoneuron. Then, a voltage differential between at least one active electrode and the at least one electrode during the passing of the current can be set in proportion to the determined maximal stimulus strength. For example, the voltage differential can be set at a same voltage as the maximal stimulus strength, or can be a predefined percentage of the maximal stimulus strength (e.g., 25% to 200%).

In one embodiment, the stimulator, i.e., the signal generator, can be linked to EMG (electro-myograph, muscle activity monitor) monitor to adjust the level (e.g. 50%) of muscle contraction at which the treatment session will be delivered. Similar monitor for vital signs (heart rate; blood pressure, breathing rate) can be added. Electrode gel can be used to prevent burns due to electrolysis.

An Example of Augmented Charge-Enhanced Neural Stimulation Mode (aCENS)

In another embodiment of the present invention, augmented charge-enhanced neural stimulation mode (aCENS) can be employed to rehabilitate a neural pathway between a first neural component and a second neural component. As discussed above, the first neural component and the second neural component can be in any of the following three combinations:

a. a cortex neuron for the first neural component and a lower motoneuron for the second neural component;
b. a first cortex neuron for the first neural component and a second cortex neuron for the second neural component; and
c. a sensory neuron for the first neural component and a cortex neuron for the second neural component.

In general, direct current (DC) stimulation is a non-invasive technique used to modulate the excitability of the central nervous system. When DC stimulation is delivered trans-cranially, a positively- or negatively-charged stimulating electrode (anode or cathode, respectively) is positioned at the cortical area to be stimulated, while a reference electrode is usually situated at a distance. Trans-cranial DC stimulation (tcDC) is used to modulate the excitability of the motor cortex, ameliorate the perception of pain, modulate cognitive functions, and/or treat depression. The effect of DC stimulation depends on the topography of neurons relative to the applied field, interactions between functional neuronal circuits, and the polarity of the electrode. For example, while cathodal stimulation depresses neuronal activity, anodal stimulation activates neurons.

The spinal cord contains various populations of excitatory and inhibitory interneurons that mediate cortical and subcortical inputs. By acting on these interneurons, as well as lower motoneurons and ascending and descending processes, DC stimulation at the spinal level could exert modulatory effects on cortical and sub-cortical inputs to the spinal cord. Although DC stimulation has been found to improve functional recovery after spinal cord injury, only a few studies have investigated the effects of trans-spinal direct current (tsDC) on the excitability of spinal neurons, and its effects on corticomotoneuronal transmission have never been investigated.

Research leading to the present disclosure show differential modulatory effects of tsDC polarity on spontaneous activity, which are shown below. Cortically-elicited triceps surae (TS) twitches were increased during cathodal trans-spinal direct current (c-tsDC), then depressed after termination, and were decreased during anodal trans-spinal direct current (a-tsDC), then potentiated after termination. While a-tsDC and rCES produced similar effects as a-tsDC alone, c-tsDC and rCES showed the greatest improvement in cortically-elicited TS twitches.

In one embodiment, DC stimulation can be employed to improve spinal responses to cortical stimulation. In many neurological disorders, connectivity between the cortex and spinal cord is compromised (e.g., spinal cord injury or stroke). Stimulation protocols can be employed to strengthen spinal responses. As illustrated in the studies described below, neuronal activity is important in shaping c-tsDC after-effects. Specifically, c-tsDC can optimize cortico-spinal activity during stimulation, and depress it at other times. The ability of c-tsDC to interact with cortical activity to cause different outcomes is an interesting phenomenon that can support many clinical uses of c-tsDC. Translating this to rehabilitative strategies, either artificial cortical stimulation (when voluntarily muscle activation is impossible) or voluntary training during the application of c-tsDC can be employed to strengthen signal responses. Moreover, the depressive effect of c-tsDC can be used to manage spasticity resulting from many neurologic disorders.

C-tsDC can cause motoneurons to be more responsive to synaptic activation, but less inclined to generate spontaneous activity. This may explain why cortically-elicited TS twitches were potentiated during c-tsDC application. Moreover, pre-synaptic hyperpolarization has been shown to increase excitatory post-synaptic potentials (EPSPs). See Eccles J., Kostyuk, P. G., Schmidt, R. F., The effect of electric polarization of the spinal cord on central afferent fibres and on their excitatory synaptic action, J. Physiol. 162: 138-150 (1962); Hubbard J. I. and Willis W. D., Hyperpolarization of mammalian motor nerve terminals, J. Physiol. 163: 115-137 (1962); Hubbard J. I., and Willis W. D., Mobilization of transmitter by hyperpolarization, Nature 193: 174-175 (1962). Such hyperpolarization is expected to occur in cortico-spinal tract terminals and in spinal interneurons between the cortico-spinal tract and spinal motoneurons. Thus, nerve terminal hyperpolarization and dendrite depolarization induced by c-tsDC would cause potentiation of cortically-elicited TS twitches.

In a study leading to the present disclosure presented below, cortically-elicited TS twitches were depressed following c-tsDC and potentiated following a-tsDC. DC stimulation of the brain has similar results, as anodal stimulation increases while cathodal stimulation decreases the excitability of the motor cortex in humans and in mice. Anodal-induced excitability appears to depend on membrane depolarization, while cathodal-induced depression depends on membrane hyperpolarization. In addition, after-effects of both anodal and cathodal stimulation involve the N-methyl-D-aspartate (NMDA) glutamate receptor.

Figure 19:
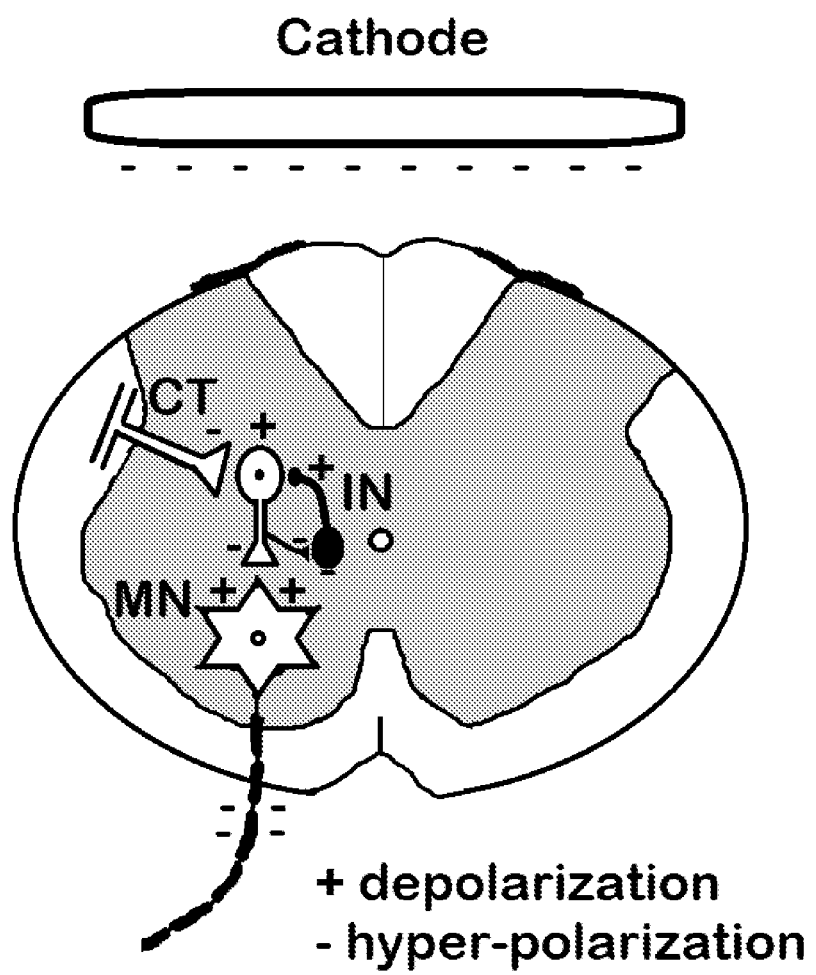
FIG. 19 is a hypothetical diagram illustrating possible changes in membrane potential when the spinal electrode negative delivers a polarizing current (not to scale).

Pairing rCES with c-tsDC can not only prevent depression of cortically-elicited TS twitches after c-tsDC termination, but remarkably improve twitches. C-tsDC seems to induce a polarizing pattern as shown in FIG. 19, including pre-synaptic hyperpolarization and post-synaptic depolarization within the corticomotoneural pathway.

In theory, neuronal compartments in close proximity to the negative electrode should depolarize, and distant compartments should hyperpolarize. Therefore, excitability of neurons with dendrites oriented dorsally and axons oriented ventrally should increase, and excitability of neurons oriented in the opposite direction (ventral to dorsal) should decrease. Reversing the direction of the polarizing current should result in opposite changes of membrane potential. The negative (−) and positive (+) signs indicate the status of the trans-membrane potential. CT, corticospinal tract; IN, interneuron; MN, motoneuron.

This pattern, combined with rCES, would evoke long-term potentiation. Specifically, pre-synaptic hyperpolarization has been shown to increase the size of EPSPs, which would subsequently increase neurotransmitter release and thereby cortical input. Although a low frequency stimulation was applied to the motor cortex in the study described below, the actual frequency of cortical input was probably much higher. In addition, post-synaptic depolarization would activate the NMDA receptor. The association between pre-synaptic increase of neurotransmitter release and steady post-synaptic depolarization would trigger the induction of long-term potentiation. This could serve as the main mechanism for c-tsDC-induced enhancement of cortically-elicited TS twitches. Furthermore, reduction of inhibitory inputs to spinal circuits could also mediate the after-effects of paired rCES and c-tsDC.

A method of employing a tsDC stimulator is illustrated in FIG. 11. The stimulation system includes multiple independent stimulator units that are integrated in a single system, either in one box or in a plurality of boxes with electrical connections therebetween. A first stimulator unit, labeled "polarizing," delivers a polarizing current between a point on a spinal column and a point located outside of the central nervous system. Optionally, a second stimulator unit, labeled "brain," can deliver current to the motor cortex either synchronously with the polarization current or asynchronously with the polarization current to reinforce the stimulation provided by the first stimulator. Optionally, a third stimulator unit, labeled "muscle 1," can deliver current to a muscle area either synchronously with the polarization current or asynchronously with the polarization current to reinforce the stimulation provided by the first stimulator. The third stimulator unit can be used with the second stimulator unit, or without the second stimulator unit. Additional stimulator units, represented by a fourth stimulator unit labeled "muscle 2," can be used with the third stimulator unit to deliver unipolar negative current to another muscle area.

Figure 12:
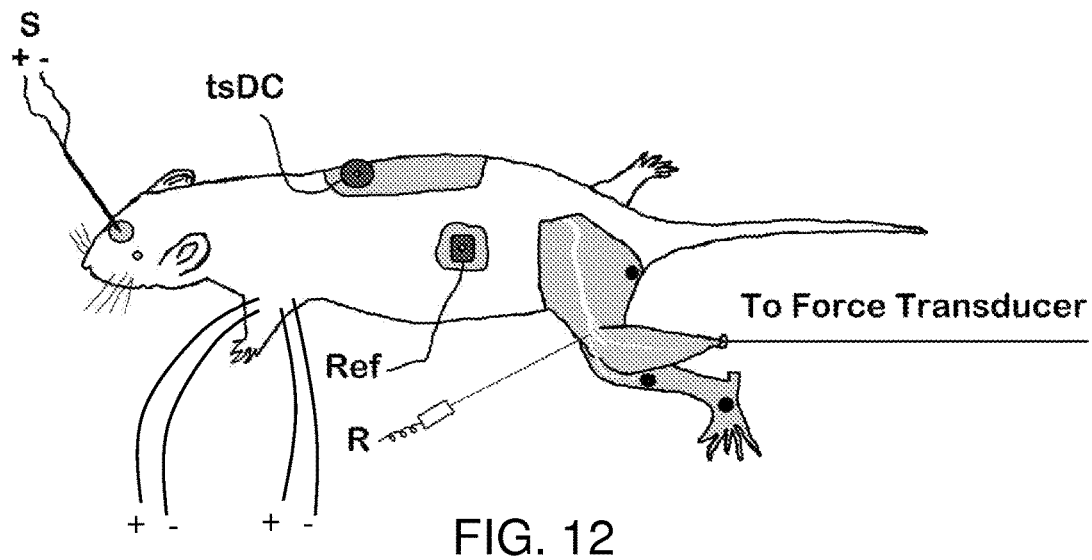
FIG. 12 is an exemplary setup employing the second configuration. This setup was also employed for an experimental setup for the study described below.

The points at which the polarizing current is applied to a vertebrate being are schematically illustrated in FIG. 12. While a mouse is schematically shown in FIG. 2, this configuration can be employed for any vertebrate being including a human. Specifically, an active electrode, labeled "tsDC," is placed on a first point located at the spinal column, which can be at any level within the spinal column between, and including, the first spinal cord level and the last spinal cord level. A reference electrode, labeled "Ref," can be placed on a second point located at any area other than the area of the central nervous system, i.e., outside of the brain and the spinal column. Because simulation of an area of the spinal column contacted by the active electrode is preferred than stimulation of the area contacted by the reference electrode, the reference electrode is preferably placed at some distance away from the spinal column. While the reference electrode is shown as a single electrode in FIG. 12, the reference electrode can be replaced with a plurality of reference electrodes as illustrated in FIG. 11. Using a plurality of reference electrodes instead of a single reference electrode enhances the effect of the electrical stimulation provided by the active stimulus because the current density at the plurality of reference electrodes can be maintained low, while the current density at the active electrode can be maintained high.

Typically, the voltage at the reference electrode(s) is held constant, and the voltage at the active electrode has the form of electrical pulses with a pulse duration 0.5 to 5 ms and a frequency from 0.5 Hz to 5 Hz, although lesser and greater pulse durations and lesser and greater frequencies can also be employed. The polarity of the electrical pulse applied to the active electrode can be either positive or negative depending on applications.

In case the vertebrate being is a human, a pair of reference electrodes placed on an anterior pelvis can provide effective stimulation to an area of the spinal column. One of the most effective configurations for placement of a pair of reference electrodes employs a point at the anterior superior iliac spine on the right side and a point at the anterior superior iliac spine on the left side. In this case, a second point for placing a reference electrode in an embodiment employing a single reference electrode is replaced by a second point and an additional point on which two reference electrodes are placed. In other words, a reference electrode for spinal polarizing current can be implemented as a pair of reference electrodes that are split and placed over the right and left anterior superior iliac spines. The pair of reference electrodes is held at the same electrostatic potential.

The location of the first point, i.e., the point at which the active electrode is placed, depends on the nature of the neuromuscular condition for which the treatment is performed. The location of the first point can be selected to maximize the effect of the treatment. For example, if the treatment is intended to improve the neuromuscular condition of a vertebrate being for injuries suffered at a location in the spinal column, the first point can be located in a spinal cord level immediately above, i.e., immediately more proximal to the brain than, the site of the spinal injury. In other words, for treatment of a spinal cord injury, the active electrode of polarizing current can be placed so that the primary current passes through the injury site. An active electrode is placed at the spinal cord level immediately above the injury site, and reference electrodes can be placed as described above. In one embodiment, repetitive stimulations at the brain (pulsed DC current that are applied synchronously with, or asynchronously from, the primary electrical current through the active electrode and the reference electrode(s)) can be paired with the polarizing spinal current.

If the treatment is intended to improve the neuromuscular condition of a vertebrate being for conditions caused by a trauma or a dysfunction in the brain, the first point can be located at the spinal cord level one, i.e., the part of the spinal column closest to the brain. Conditions caused by a trauma or a dysfunction in the brain include such disabilities as cerebral palsy, amyotrophic lateral sclerosis (ALS, otherwise known as Lou Gehrig's disease), traumatic brain injury, stroke, etc. In other words, for treatment of conditions where the injury is located in the brain, the polarizing electrode can be located on the spinal area innervating the target limb. For treatment of conditions affecting lower extremities, the active polarizing electrode should be situated at vertebral level T10 to L1 above the lumbar enlargement. For treatment of conditions affecting upper extremities, the active polarizing electrode can be placed at the level of T2 and below. In one embodiment, repetitive stimulations at the brain (pulsed DC current that are applied synchronously with, or asynchronously from, the primary electrical current through the active electrode and the reference electrode(s)) can be paired with the polarizing spinal current.

For treating a condition such as ALS, stimulation intervention can also be applied to target muscles (in the form of localized pulsed DC current) affected by the condition, simultaneously with application of the polarizing current to a spinal cord region innervating the target muscles and application of local stimulation to the motor cortex (in the form of localized pulsed DC current). These treatments should be repeated at different areas according to the condition.

If the treatment is intended to improve the neuromuscular condition of a vertebrate being for injuries to, or disabilities caused by a malfunction at, a peripheral nerve, the first point can be located in a spinal cord level at which a corresponding lower extremity circuit is located, and preferably at a spinal cord level that is most proximal to the location of the injury or the disability. Conditions caused by an injury or a disability located at a nerve include, for example, peripheral palsy, Erb's palsy, and/or other peripheral nerve injuries due to nerve compression, tension, or torsion (e.g., sciatica). For treating a condition such as Erb's palsy, stimulation intervention can also be applied to target muscles (in the form of localized pulsed DC current) affected by the condition, simultaneously with application of the polarizing current to a spinal cord region innervating the target muscles and application of local stimulation to the motor cortex (in the form of localized pulsed DC current). These treatments should be repeated at different areas according to the condition.

The electrical simulation to the spinal column can be provided alone or in combination with additional electrical stimulations to the brain and/or to at least one muscle. The effectiveness of synchronous or asynchronous application of additional electrical simulation to the brain and/or the at least one muscle depends on the nature of the injury or disability.

An electrical stimulation to the brain is schematically illustrated in FIG. 12 by two electrodes placed at the motor cortex of a vertebrate being. The electrical stimulation provided to the brain is a local stimulation in which an area of the motor cortex of the electrical being is stimulated synchronously with, or asynchronously from, the electrical stimulation of the spinal column by the first stimulator unit. The local electrical stimulation to the motor cortex can be applied employing a concentric electrode pair as illustrated in FIG. 12, or can be employed by a set of electrodes, e.g., a third electrode and a fourth electrode that are placed at two different points at the motor cortex. The third electrode and the fourth electrode are schematically shown in FIG. 11 as two electrodes connected to the second stimulator unit labeled "Brain."

Additional electrical stimulation can be provided to at least one muscle, i.e., a single muscle or a plurality of muscles, synchronously with, or asynchronously from, the electrical stimulation of the spinal column by the first stimulator unit. If a local electrical stimulation to the brain is employed, the additional electrical stimulation the at least one muscle can be applied synchronously with, or asynchronously from, the local electrical stimulation to the brain by the second stimulator unit. The additional electrical stimulation can be provided by a third stimulator unit and/or additional stimulator unit(s), such as the stimulator units labeled "Muscle 1" and "Muscle 2" in FIG. 11. A single pair of electrodes or multiple pairs of electrodes can be connected to a stimulator unit that stimulates a muscle. FIG. 12 schematically illustrates an exemplary placement scheme for the additional electrodes in which the additional electrodes are placed on a forelimb of a mouse. In general, at least one pair of additional electrodes can be placed at one or multiple pairs of points on any part of the body excluding the central nervous system, and particularly at any limb.

Electrodes connected to each of the stimulator units in FIG. 11 can be a single pair of electrodes or multiple pairs of electrodes. Each pair of electrodes includes an active electrode and a reference electrode. Further, each reference electrode can be replaced with a plurality of reference electrodes to prevent concentration of current to a single reference electrode and to enable increase in the current density at the point at which the corresponding active electrode is present.

The second stimulator unit can deliver unipolar positive current to the motor cortex either synchronously with the polarization current or asynchronously with the polarization current to reinforce the stimulation provided by the first stimulator. Further, the third stimulator unit, labeled "muscle 1," can deliver unipolar negative current to a muscle area either synchronously with the polarization current or asynchronously with the polarization current to reinforce the stimulation provided by the first stimulator. Selecting the polarity of the electrical stimulations so that the voltages applied to the motor cortex is in general positive and the voltages applied to the at least one muscle is in general negative can enhance the effectiveness of the treatment, especially when the electrical stimulations are applied synchronously.

As discussed above, the first and second unipolar stimulator units of FIG. 11 can be synchronized to deliver pulses simultaneously. Each unit can have its independent control panel. The third, polarizing stimulator unit can have the options to be either synchronized with the first and second stimulators, or can function independently, i.e., asynchronously from the first and second stimulators. In addition, the number of electrodes per connection (splitting into more than one electrode, e.g. 4) can be as in the previous design as described above. For some applications, a dipolar corticomuscular stimulator in this configuration is more preferable for human intervention because the stimulator gives more flexibility in designing stimulation patterns, and can be safer and less painful.

In general terms, the invention described herein can be practiced employing a system for improving a neuromuscular condition of a vertebrate being. The system includes at least one active electrode, at least one reference electrode, a stimulator, and at least one first lead wire and at least one second lead wire, which are employed to form an electrical circuit that includes a vertebrate being.

Each of the at least one active electrode can be sized and configured to be placed at, or in proximity to, a first point. The first point is selected from the motor cortex and a muscle, and is located on one side of a spinal column of the vertebrate being. The at least one active electrode can be a single active electrode as illustrated in FIG. 1A (See the section on experimental data for description of components in FIG. 1A), or can be a plurality of active electrodes as illustrated in FIG. 10, or include a active electrode attached to a stimulator unit (labeled "brain") and at least another active electrode attached to another stimulator unit (labeled "polarizing") as illustrated in FIG. 11.

Each of the at least one reference electrode can be sized and configured to be placed at, or in proximity to, a second point. The second point is selected from the motor cortex and a muscle, and is located on the opposite side of the spinal column. The at least one reference electrode can be a single reference electrode as illustrated in FIG. 1A, or can be a plurality of reference electrodes as illustrated in FIG. 10, or include a reference electrode attached to a stimulator unit (labeled "muscle") and at least another reference electrode attached to another stimulator unit (labeled "polarizing") as illustrated in FIG. 11.

The stimulator can be configured to generate electrical stimulation waveforms. Each of the at least one first lead wire couples the stimulator to an active electrode among the at least one active electrode. Each of the at least one second lead wire couples the stimulator to one of the at least one reference electrode. In one embodiment, the system can be configured to form a current path through a motor pathway across the spinal column between the first point and the second point. In another embodiment, the system can be configured to form a current path between a first point in the spinal column and a second point outside the central nervous system.

The stimulator can configured to pass the electrical current as a plurality of pulses having a duration from 0.5 ms to 5 ms, although lesser and greater durations can also be employed. Further, the stimulator can configured to pass the electrical current as a plurality of pulses having a frequency from 0.5 Hz to 5 Hz.

The system can further include prompt means for providing a prompt to move a limb to the vertebrate being during, or immediately before, the passing of the electrical current. The prompt can be provided in any of the embodiments described above. The prompt can be an aural prompt, a visual prompt, or a tactile prompt. The prompt means can be an automated control unit configured to generate the prompt in synchronization with the passing of the electrical current. The prompt means can be used for any vertebrate being capable of understanding the prompt, or trained to recognize the prompt (for example, by conditional reflexes). In this case, a prompt to move a limb can be provided to the vertebrate being during, or immediately before, the passing of the electrical current. The prompt can be provided by an automated control unit configured to generate the prompt in synchronization with the passing of the electrical current.

Alternatively or in addition, the vertebrate being can be a human, and the prompt can be provided by another human to the human or to a non-human vertebrate being capable of understanding the prompt, or trained to recognize the prompt. The other human can be a therapist. In addition, the prompt means can provide the prompt indirectly to the vertebrate being by first providing a direct prompt to the therapist or a trainer as the case may be, and then allowing the therapist or the trainer to provide a prompt to the vertebrate being.

The vertebrate being can be a mammal, and the muscle can be a muscle in a limb of the mammal. The vertebrate being can a human, and the muscle can be a muscle in a human limb.

The stimulator can be configured to apply a first voltage to the at least one active electrode and a second voltage to the at least one reference electrode simultaneously. Further, the stimulator can be configured to pass the electrical current flows through a plurality of paths as illustrated in FIGS. 10 and 11. The plurality of paths can include a first path between the motor cortex and one of the plurality of muscles (for example, as provided by the first stimulator unit and the second stimulator unit in FIG. 11) and a second path between two of the plurality of muscles (for example, as provided by the third stimulator unit). Each of the plurality of paths can run across the spinal column. In this case, at least one of the plurality of paths run across the spinal column.

In the system of the present disclosure, the stimulator can be configured to apply a first voltage to the at least one active electrode and a second voltage to the at least one reference electrode simultaneously. Further, the stimulator can include at least one stimulator unit configured to provide the electrical current by applying a first voltage to the at least one active electrode and a second voltage to the at least one reference electrode. In this case, the electrical current can be provided by the stimulator including at least one stimulator unit that applies the first voltage to the at least one active electrode and the second voltage to the at least one reference electrode to improve the neuromuscular condition of the vertebrate being.

The at least one stimulator unit can be configured to apply the first voltage and the second voltage simultaneously. In this case, the at least one stimulator unit can apply the first voltage and the second voltage simultaneously to improve the neuromuscular condition of the vertebrate being.

The at least one stimulator unit can include a plurality of stimulator units. A first stimulator unit can be configured to apply the first voltage and a second stimulator unit can be configured to apply the second voltage simultaneously with application of the first voltage by the first stimulator unit. Thus, the first voltage can be applied by a first stimulator unit and the second voltage can be applied by a second stimulator unit simultaneously.

The plurality of stimulator units can further include a third stimulator unit configured to deliver polarizing current between the brain of the vertebrate being and a muscle of the vertebrate. Polarizing current can be delivered between the brain of the vertebrate being and a muscle of the vertebrate being employing the third stimulator unit to improve the neuromuscular condition of the vertebrate being. The third stimulator unit can be synchronized with the first and second stimulator units so that the polarizing current is delivered simultaneously with the first voltage and the second voltages. Alternatively, the third stimulator unit can be configured to operate independently from the first and second stimulator units so that the polarizing current is delivered asynchronously from the first voltage and the second voltages. In this case, the third stimulator unit can be operated independently from the first and second stimulator units so that the polarizing current is delivered asynchronously from the first voltage and the second voltages.

The at least one stimulator unit can be a plurality of stimulator units including a stimulator unit configured to apply the first voltage and the second voltage simultaneously. The first voltage and the second voltage can be applied by a stimulator unit simultaneously. Another stimulator unit, such as the third stimulator unit, can be configured to deliver polarizing current between the brain of the vertebrate being and a muscle of the vertebrate being. In this case, polarizing current can be delivered between the brain of the vertebrate being and a muscle of the vertebrate being employing another stimulator unit. The other stimulator unit, e.g., the third stimulator unit, can be synchronized with the stimulator unit that delivers the first voltage and/or the second voltage so that the polarizing current is delivered simultaneously with the first voltage and the second voltages. Alternatively, the other stimulator unit can be configured to be operated independently from the stimulator unit so that the polarizing current is delivered asynchronously from the first voltage and the second voltages. In this case, the other stimulator unit is operated independently from the stimulator unit so that the polarizing current is delivered asynchronously from the first voltage and the second voltages to improve the neuromuscular condition of the vertebrate being.

First Experiment (Employing iCENS)

In the first experiment, dipolar cortico-muscular stimulation (dCMS), which is a subspecies of iCENS, was applied to mice. A new configuration of electrical stimulation is provided herein as it was tested in anesthetized control and spinal cord injury (SCI) mice. Constant voltage output was delivered through two electrodes. While the negative voltage output (ranging from −1.8 to −2.6V) was delivered to the muscle (two-wire electrode, 500 μm), the positive output (ranging from +2.4 to +3.2V) was delivered to the primary motor cortex (M1) (electrode tip, 100 μm). The configuration was named dipolar cortico-muscular stimulation (dCMS) and consisted of 100 pulses (1 ms pulse duration, 1 Hz frequency).

In experimental testing, constant voltage output was delivered through two electrodes. While the negative voltage output (ranging from −1.8 to −2.6V) was delivered to the muscle, the positive output (ranging from +2.4 to 3.2V) was delivered to the primary motor cortex (M1). The configuration consisted of 100 pulses (1 ms pulse duration, 1 Hz frequency). In SCI animals, after dCMS, muscle contraction improved remarkably at the contralateral (456%) as well as ipsilateral (457%) gastrocnemius muscle. The improvement persisted for the duration of the experiment (60 min.). The enhancement of the muscle force was accompanied by the reduction of M1 maximal threshold and the potentiation of spinal motoneuronal evoked responses at the contralateral (313%) and ipsilateral (292%) sides of the spinal cord. Moreover, spontaneous activity recorded from single spinal motoneurons was substantially increased contralaterally (121%) and ipsilaterally (54%). Interestingly, spinal motoneuronal responses and muscle twitches evoked by stimulation of non-treated M1 (received no dCMS) were significantly enhanced as well. Similar results obtained from control animals albeit the changes were relatively smaller. These findings demonstrated that dCMS could improve functionality of motor pathway and dramatically attenuates the effects of spinal cord injury.

In SCI animals, after dCMS, muscle contraction improved markedly at the contralateral (456%) and ipsilateral (457%) gastrocnemius muscles. The improvement persisted for the duration of the experiment (60 min). The enhancement of the muscle force was accompanied by the reduction of M1 maximal threshold and the potentiation of spinal motoneuronal evoked responses at the contralateral (313%) and ipsilateral (292%) sides of the spinal cord. Moreover, spontaneous activity recorded from single spinal motoneurons was substantially increased contralaterally (121%) and ipsilaterally (54%). Interestingly, spinal motoneuronal responses and muscle twitches evoked by the test stimulation of non-treated M1 (received no dCMS) were significantly enhanced as well. Similar results obtained from control animals albeit the changes were relatively smaller. Conclusion. These findings demonstrated that dCMS could improve functionality of motor pathway and thus it may have therapeutic potential.

Methods

Animals

Specifically, experiments were carried out on CD-1, male and female adult mice in accordance with National Institute of Health ("NIH") guidelines. All protocols were approved by the College of Staten Island IACUC. Animals were housed under a 12 h light-dark cycle with free access to food and water.

Spinal Cord Contusion Injury

Mice were deeply anaesthetized with ketamine/xylazine (90/10 mg/kg i.p.). A spinal contusion lesion was produced (n=15 mice) at spinal segment T13 using the MASCIS/NYU impactor. 1 mm-diameter impact head rod (5.6 g) was released from a distance of 6.25 mm onto T13 spinal cord level exposed by a T10 laminectomy. After injury, the overlying muscle and skin was sutured, and the animals were allowed to recover under a 30° C. heating lamp. To prevent infection after the wound was sutured, a layer of ointment contained gentamicin sulfate was applied. Following surgery, animals were maintained under pre-operative conditions for 120 days before testing. The time of recovery was selected to ensure that animals developed a stable chronic spinal cord injury.

Behavioral Testing

Behavioral testing (n=15 animals with SCI) was performed 120 days post-injury to confirm that animals developed behavioral signs of locomotor abnormalities, spasticity syndrome, and sensorimotor incoordination at the hindlimbs. We have only used animals that demonstrated higher (proximately symmetrical in both hindlimbs) behavioral abnormalities. After acclimation to the test environment, three different testing procedures were used to quantify these behavioral problems.

Basso mouse scale (BMS): Motor ability of the hindlimbs was assessed by the motor rating of Basso mouse scale (BMS). The following rating scale was used: 0, no ankle movement; 1-2, slight or extensive ankle movement; 3, planter placing or dorsal stepping; 4, occasional planter stepping; 5, frequent or consistent planter stepping; no animal scored more than 5. Each mouse was observed for 4 min in an open space, before a score was given.

Abnormal pattern scale (APS): After SCI, animals usually developed muscle tone abnormalities that were exaggerated during locomotion and lifting the animal off the ground (by the tail). APS was developed to quantify the number of muscle tone abnormalities demonstrated by animals after SCI in two situations: on ground and off ground. The following rating scale was used: 0, no abnormalities; 1, for each of the following abnormalities: limb crossing of midline, abduction, and extension or flexion of the hip joint, paws curling or fanning, knee flexion or extension, ankle dorsi or planter flexion. The total score was the sum of abnormalities from both hindlimbs. The maximal score in APS was 12. Abnormal patterns were usually accompanied by spasmodic movements of the hindlimbs.

Horizontal ladder scale (HLS): For accurate placing for the hindlimb, animals had to have normal coordination between sensory and motor systems. For testing sensorimotor coordination, a grid with equal spacing (2.5 cm) was used. Animals were placed on the grid and were allowed to take 20 consecutive steps. Foot slips were counted as errors.

Electrophysiological Procedures.

Intact (n=10) and SCI (n=21) animals underwent a terminal electrophysiological experiment. Animals were anesthetized using ketamine/xylazine (90/10 mg/kg i.p.), which was found to reserve corticospinal evoked potential. Electrophysiological procedures started ~45 min after the first injection of anesthesia to perform the experiments at intermediate to light levels of anesthesia, as recommended by Zandieh and colleagues. See Zandieh S., Hopf R., Redl H., Schlag M. G., The effect of ketamine/xylazine anesthesia on sensory and motor evoked potentials in the rat. Spinal Cord, 41:16-22 (2003). This was determined by the presence of front or hind limb withdrawal reflex. As needed, anesthesia was kept at this level using supplemental dosages (~5% of the original dose).

The entire dorsal side of each animal was shaved. The skin covering the two hindlimbs, lumbar spine, and the skull was removed. The two gastrocnemii muscles (right and left) were carefully separated from the surrounded tissue preserving blood supply and nerves. The tendon of each of the muscles was threaded with a hook shaped 0-3 surgical silk, which was connected to the force transducers. Next, a laminectomy was performed in the 2nd, 3rd, and 4th lumbar vertebrae (below the lesion in animals with SCI); the 13th rib was used as a bone land mark to identify the level of spinal column. Since spinal cord levels are ~3 levels displaced upward relative to vertebral levels, the recording was assumed to be performed at spinal cord levels: 5th and 6th lumbar and 1st sacral. A craniotomy was made to expose the primary motor cortex (M1) (usually the right M1) of the hindlimb muscles located between 0 to −1 mm from the Bregma and 0 to 1 mm from midline. The dura was left intact. The exposed motor cortical area was explored with a stimulating electrode to locate the motor point from which the strongest contraction of the contralateral gastrocnemius muscle was obtained using the weakest stimuli. In experiments aimed to test the effect of dCMS on nonstimulated motor pathway, two craniotomies were made over the right and left hind limb areas of M1.

Both hind and fore limbs and the proximal end of the tail were rigidly fixed to the base. Both knees were also fixed into the base to prevent transmitting any movement from stimulated muscles to the body and vice versa. Muscles were attached to force displacement transducers and the muscle length was adjusted to obtain the strongest twitch force (optimal length). The head was fixed in a custom made clamping system. The whole setup was placed on an antivibration table. Animals were kept warm during the experiment with radiant heat.

A stainless steel stimulating electrode (500 μm shaft diameter; 100 μm tip) was set on the exposed motor cortex. Paired stainless steel stimulating electrode (~15 mm spacing; 550 μm diameter) was placed on the belly of the gastrocnemius muscle. The same electrode was alternated between left and right muscles according to experimental procedure. Electrodes were then connected to stimulator outputs. Extracellular recordings were made with pure iridium microelectrodes (0.180 shaft diameter; 1-2 μm tip; 5.0 MΩ). Two microelectrodes were inserted through two small openings that were carefully made into the spinal dura matter on each half (right and left) of the spinal cord. The insertion was made at approximately the same segmental level of the spinal cord. Reference electrodes were placed in the tissue slightly rostral to the recording sites. The ground electrodes were connected to the flap of skin near the abdomen. Motorized micromanipulators were used to advance the microelectrodes into the ventral horns. Extracellular activity was passed through a standard head stage, amplified, filtered (bandpass, 100 Hz to 5 KHz), digitized at 4 KHz, and stored in the computer for further processing. A power lab data acquisition system and LabChart 7 software by ADInstruments, Inc, CO, USA were used to acquire and analyze the data.

Once a single motoneuron was isolated at the left and right side of the spinal cord, few antidromic pulses (range, −9 to −10 V) were applied to the homonymous gastrocnemius muscle. As described by Porter, the presence of antidromically-evoked response with a short latency (3.45 ms) indicated that the recording electrode was placed in the vicinity of the neuron innervating stimulated muscle. See Porter R., Early facilitation at corticomotoneuronal neuronal synapses, J. Physiol. 207:733-745 (19700. These recordings were also used to calculate the latency of ipsilateral and contralateral spinal responses to muscle stimulation. A cortical pre-test stimulation of 10 pulses (anodal monopolar) at maximal stimulus strength (usually +8 to +10V) was applied to the primary motor cortex (M1). Maximal stimulus strength was defined as the strength of stimulation when no further increase in muscle contraction was observed. This was also used to calculate the maximal threshold of M1 stimulation.

Next, dCMS was applied through two electrodes as shown in FIG. 1A. The positive and negative voltage outputs were connected to electrodes situated on the primary motor cortex (M1), and on the contralateral gastrocnemius muscle, respectively. Each of the two gastrocnemii muscles was attached to a force transducer (not shown). Recording from single motoneuron (Rec) was performed simultaneously on each side of the spinal cord below the lesion. In FIG. 1A, IGM represents the ipsilateral gastrocnemius muscle, and CGM represents the contralateral gastrocnemius muscle.

Specifically, the negative output was connected to an electrode situated on the gastrocnemius muscle and the positive electrode was at M1. The voltage strength and polarity were computer-controlled. The strength of dCMS stimulation was adjusted so that contraction of the ipsilateral muscle (to M1) was at maximal strength which was reached just before the appearance of tail contraction (visually observed). This level of response was achieved by simultaneously applying a negative output (range, −2.8 to −1.8 V) to the muscle and positive output (range, +2.2 to +3.2 V) to M1. At this maximal strength, dCMS was delivered (100 pulses, 1 ms pulse duration, 1 Hz frequency), 15 to 20 seconds after the stimulating paradigm was ended, a post-test (with identical parameters as pre-test) stimuli were delivered to M1.

Figure 1B:
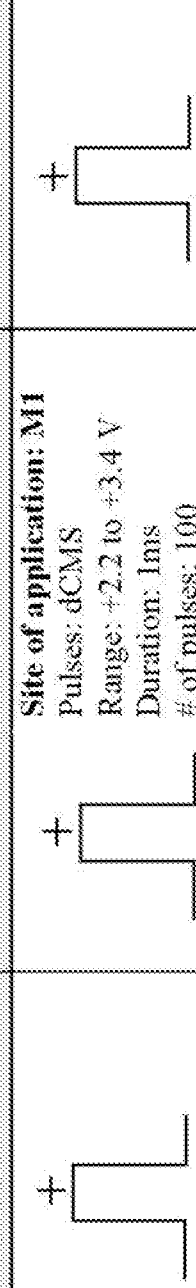
FIG. 1B is an illustration of three phases of pulses designed to evaluate dCMS.

FIG. 1B shows the experimental design for the pulsing, range, duration, number of pulses, and frequency. The experimental procedure included three phases designed to stimulate the preparation and to evaluate its reactions to dCMS. The force of muscle contraction and cortically-evoked spinal responses were evaluated before and after the application of dCMS in Pre-test and Post-test phases by application of ten monopolar pulses. The type of stimulation and location of the stimulation and recording electrodes was the same in these two phases. During dCMS phase the preparation was stimulated by application of the positive and negative pulses to the motor cortex (M1) and contralateral gastrocnemius muscle (CGM) respectively. While the number of pulses delivered during Pre- and Post-test phases was the same (10), the number of pulses delivered during dCMS was 100. The duration (1 ms) and the frequency of stimulation (1 Hz) were the same in all three phases of the experiment. The shape of the stimulating current at each phase is shown. There was a continuous recording of ipsilateral and contralateral muscle twitches and evoked and spontaneous spinal activity during the entire experiment.

Spontaneous activity was followed for 5 min, then the experiment was ended and animals were injected with a lethal overdose of anesthesia. In a subgroup of animals, the maximal threshold of M1 was re-tested. In addition, in this subgroup, in order to determine the long lasting effect of dCMS, the magnitude of cortically-evoked muscle twitches and spinal responses were retested every 20 min for 60 min after dCMS.

White Matter Staining

At the end of each experiment, animals were injected with a lethal dose of Ketamine. Two parts of the spinal column (including vertebrae and spinal cord) were dissected, one part (1.5 cm) included the lesion epicentre and another part (~0.5 cm) included the recording area (to confirm the electrodes location). Tissues were kept overnight (4° C.) in 4% paraformaldehyde in 0.1 m PBS and cryoprotected in 20% sucrose in PBS at 4° C. for 24 h. The spinal column was freeze mounted and cut into 30 μm sections and placed on poly-L-lysine-coated glass slides. The spinal column part including the lesion epicentre was sequentially sectioned from rostral. Slides were numbered to identify their locations relative to the lesion epicentre.

Four slides from each SCI animal (n=6) containing the lesion epicentre and two slides containing no signs of damaged spinal cord tissue from above and below the lesion were taken for luxol fast blue (Sigma) staining. The lesion epicentre was identified as the section containing the least amount of Luxol fast blue. Sections from control animals (n=3) at spinal cord T13 level were stained with luxol fast blue. Sections from the recording area were stained with cresyl violet.

The amount of spared white matter was measured using Adobe Photoshop CS4 by Adobe Systems, San Jose, Calif., USA. To assess the extent of the spinal cord damage, the spared white matter at the lesion epicentre was compared with the white matter at spinal cord level T13 in control animals.

Data Analysis

To evaluate the latencies, the time was recorded from the start of the stimulus artifact to the onset of the first deflection of spinal response. Measurements were made with a cursor and a time meter on LabChart software. The amplitude of spinal responses was measured as peak-to-peak. Analysis of muscle contractions were performed with peak analysis software by ADInstruments, Inc, CO, USA, as the height of twitch force measured relative to the baseline. Spike Histogram software was used to discriminate and analyze extracellular motoneuronal activity. All data were reported as group means±standard deviation (SD). Paired student's t-test was performed for before-after comparison or two sample student's t-test to compare two groups; statistical significance at the 95% confidence level ($p<0.05$). To compare responses from both sides of spinal cords recorded from control animals and from animals with SCI, one way ANOVA was performed followed with Solm-Sidak post hoc analysis. Statistical analyses were performed using SigmaPlot (SPSS, Chicago, Ill.), Excel (Microsoft, Redwood, Calif.), and LabChart software (ADInstruments, Inc, CO, USA).

Results

1. Behavioral Assessment

A contusion lesion of the spinal cord resulted in the appearance of signs of spasticity syndrome such as crossing of both limbs and fanning of the paws (compare 2A and 2C). These postural changes were quantified using the abnormal pattern scale (APS). APS showed substantial increase for both on ($APS_{on}$ 9.8±0.70) and off ($APS_{off}$ 9.8±0.70) ground conditions. These postural abnormalities were also accompanied by reduction in Basso Mouse Scale (BMS) scores from 9 in control mouse to 1.2±0.47 and 1.0±0.63 for right and left hindlimb in SCI mouse (n=15), respectively. In addition, the number of errors on a horizontal ladder test was close to maximum (20) for left (19.5±0.50) and right (18.83±1.16) hindlimb. Collectively, these results indicate that spinal cord injury procedure used in the current study was reliable in inducing behavioral signs of the injury. This strengthens the interpretation of our data.

2. Anatomical Assessment

Figure 2A:
FIG. 2A is a photograph of a control animal showing the normal posture of the hind limbs.
Figure 2B:
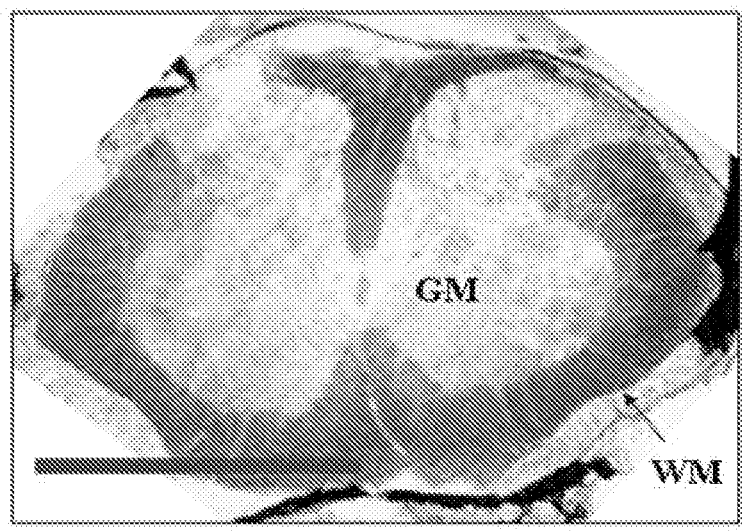
FIG. 2B is a photograph of spinal cord cross-sectional slice taken from the thoracic level of a control animal, wherein WM is white matter and GM is gray matter.
Figure 2C:
FIG. 2C is a photograph of an animal with SCI showing the abnormal pattern of the hind limbs.
Figure 2D:
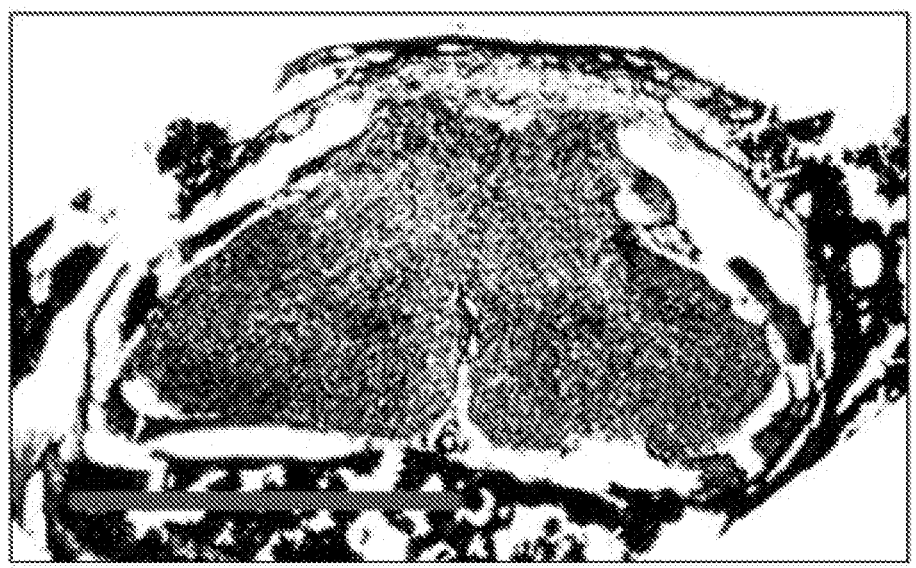
FIG. 2D is a photograph of a spinal cord cross-sectional slice taken from the thoracic level of an animal with SCI showing the lesion epicenter.
Figure 2E:
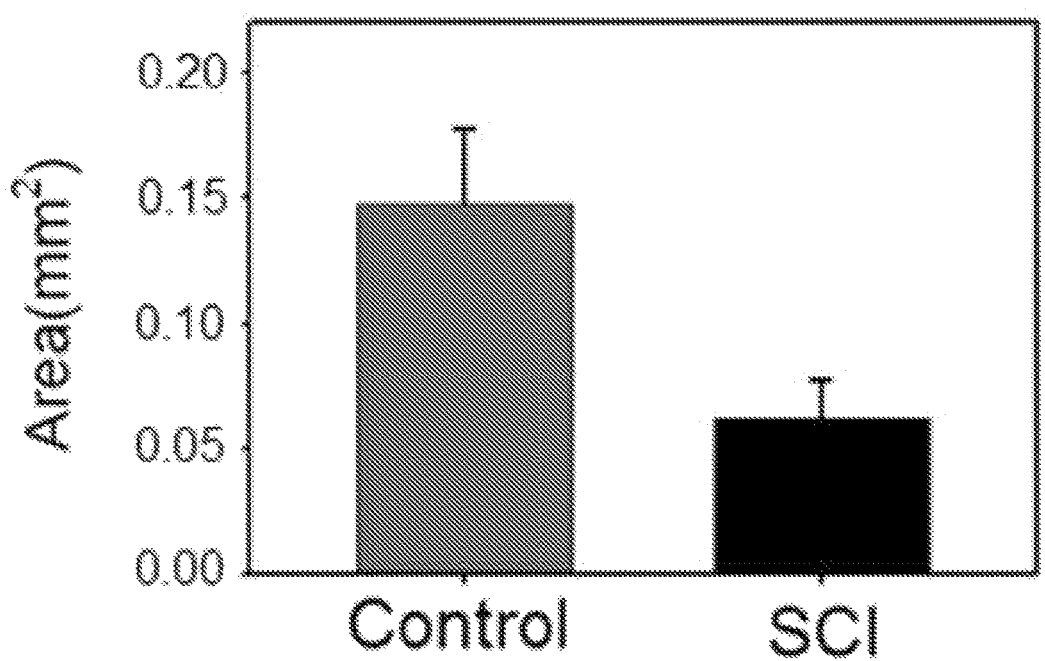
FIG. 2E is a graphical representation of a quantification of spared white matter at the lesion epicenter of animals with SCI and control animals.

FIG. 2A is a photograph of a control animal showing the normal posture of the hindlimbs. FIGS. 2B and 2D show photographs of cross-sectional slices from the thoracic spinal cord region and the lesion epicentre taken from normal and SCI animals, respectively. The lesion size was proximally equal in all injured animals tested histologically (n=6). A rim of white matter was spared on the lateral and ventral side of the spinal cord. The area of spared white matter at the lesion epicentre (0.06±0.03 mm2) was significantly reduced 16 weeks after SCI compared to the area of white matter at the same spinal level (0.15±0.06 mm2) in control animals (n=3) ($p=0.04$, t-test), FIG. 2E. On average, the total cross-sectional area (white and gray matters) of the lesion epicenter was 75±14% of the total cross-sectional area of the same spinal level in control animals.

3. Spinal Motor Neuron Identification

Figure 3A:
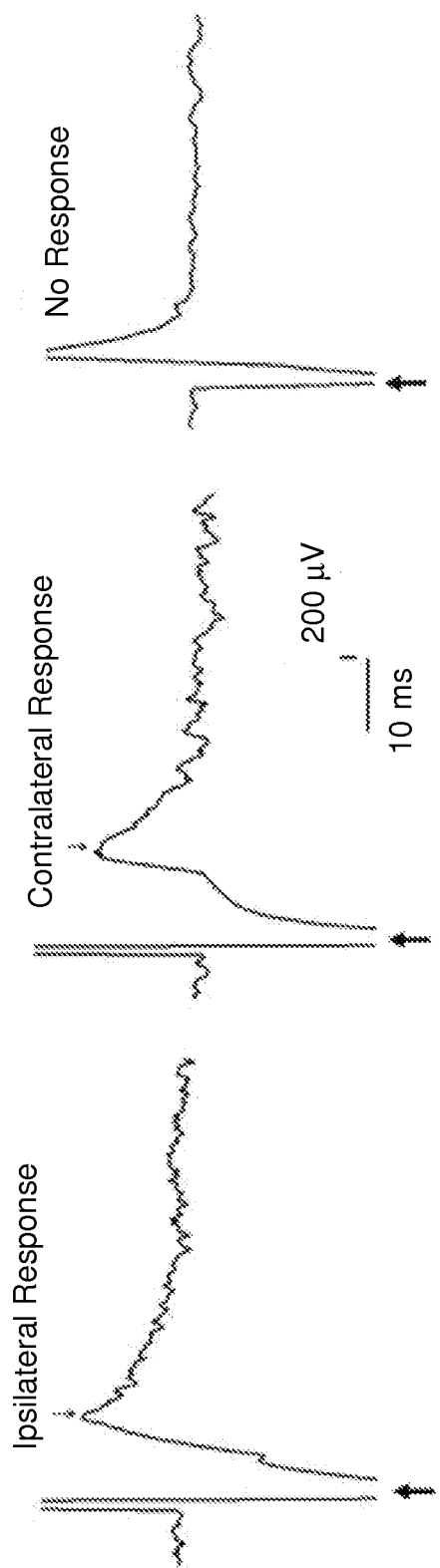
FIG. 3A illustrates the responses to the gastrocnemius muscle after stimulation.
Figure 3B:
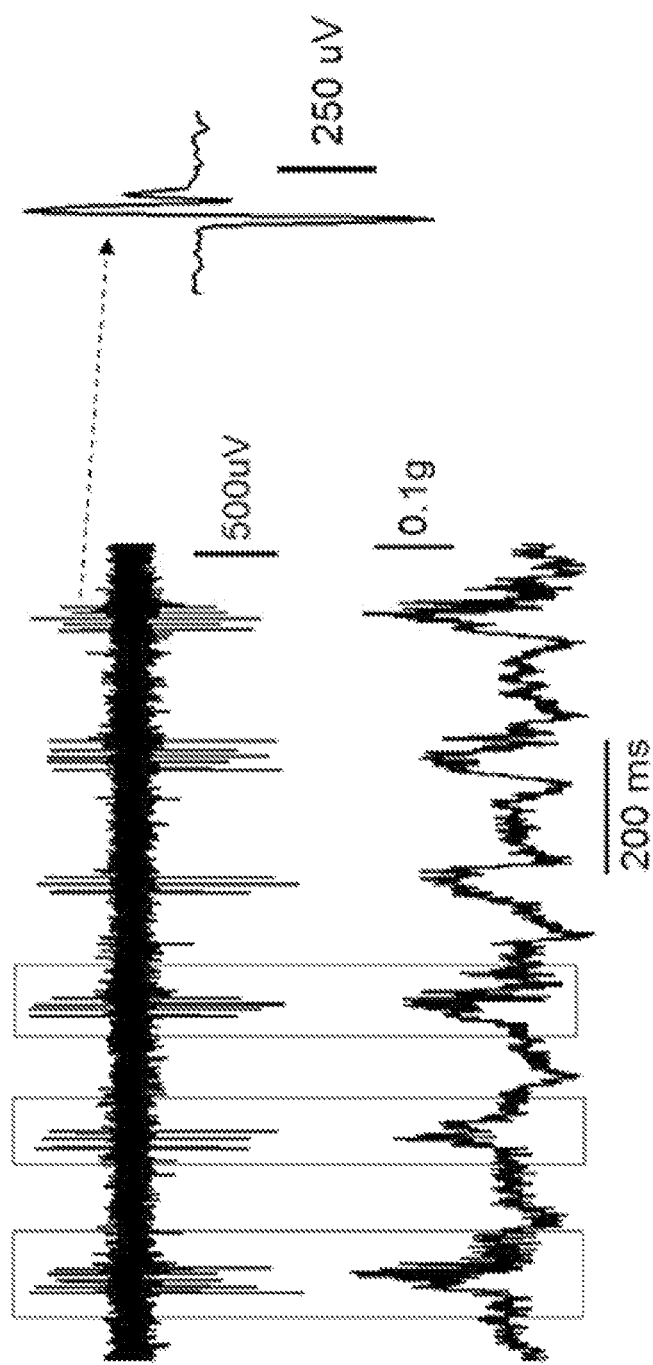
FIG. 3B is an illustration showing the identification of lower motoneurons when their spontaneous activity (upper panel) is time locked and spontaneous contractions at the ipsilateral muscle (lower panel).

Spinal motoneurons (or motor neurons) innervating the gastrocnemius muscle were at first identified by their large spontaneous spikes. The motoneuronal spike was also accompanied by a distinctive and crisp sound recorded with a loud speaker. Second criterion used to identify spinal motoneurons was their response to the stimulation of the gastrocnemius muscle. Stimulating the gastrocnemius muscle produced a short latency antidromically-generated response that was recorded from motor neurons in the ipsilateral spinal cord. Simultaneously, the microelectrode on the contralateral side of the spinal cord recorded a response that had relatively longer latency than the one picked up from the ipsilateral side. In FIG. 3A, three representative conditions were seen during the identification of motoneurons. The two panels, far left and middle, show simultaneous motoneuronal responses to stimulated gastrocnemius muscle. The far left panel shows the response of the motoneuron in the ipsilateral side. The middle panel shows the response of the motoneuron in the contralateral side. The far right panel shows a situation when the motoneuron was not responding to the antidromic stimulation of the homonymous gastrocnemius muscle. This confirmed that the unit was not innervating the stimulated gastrocnemius muscle. Third, as depicted in FIG. 3B the muscle twitches (lower panel) were correlated with motoneuron activity (upper panel). This association between spontaneous spikes and muscle twitches was used to confirm the connection. FIG. 3B shows typical spike generated by motoneuron. Finally, it was histologically confirmed that recording electrodes were localized in the ventral horn of the spinal cord.

4. Latencies

Figure 4A:
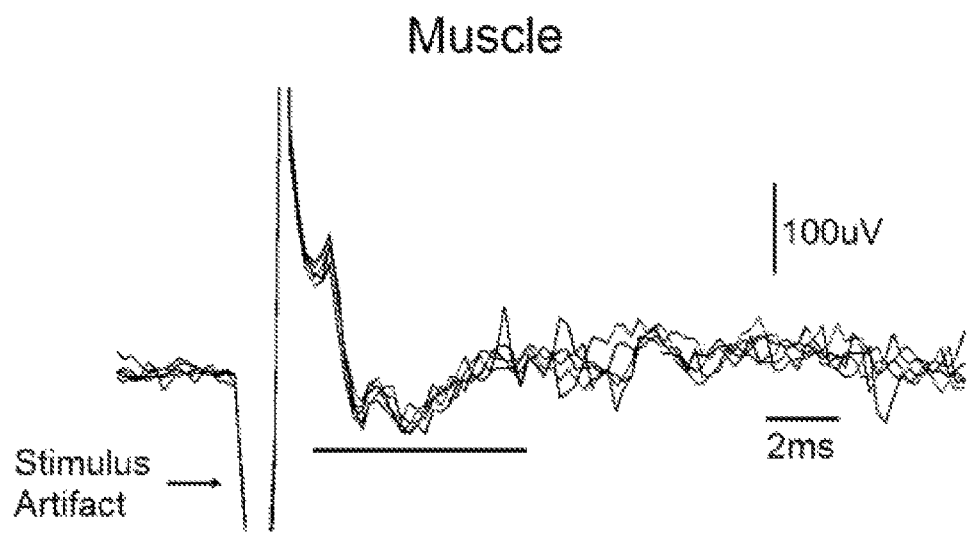
FIG. 4A is an illustration of six superimposed spinal responses after homonymous gastrocnemius muscle stimulation.

Stimulating the gastrocnemius muscle resulted in short and long latency spinal responses recorded by microelectrodes placed in the ipsilateral and contralateral ventral horns of the spinal cord, respectively. FIG. 4A shows superimposed traces of 6 antidromically-evoked responses, and the line marks the spinal responses. While the average latency of antidromically-evoked responses was 3.45±1.54 ms, the average latency of the contralateral responses (not shown) was longer (5.94±1.24 ms) indicating a transynaptic pathway. The difference between ipsilateral and contralateral spinal responses was statistically significant (n=15, $p<0.001$, t-test). Stimulating M1 resulted in ipsilateral and contralateral spinal motoneuronal responses.

Figure 4B:
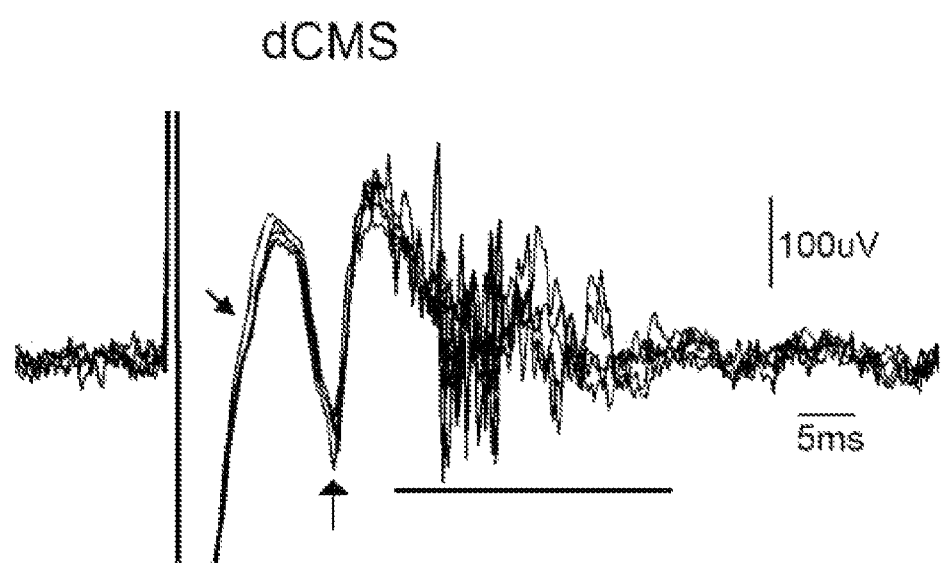
FIG. 4B is an illustration of six superimposed spinal responses after motor cortex (M1) stimulation.

FIG. 4B shows six superimposed contralateral responses after M1 stimulation. The ipsilateral response is not shown in FIG. 4A or 4B. The average latency of ipsilateral and contralateral responses was 16.09±1.02 ms and 22.98±1.96 ms, respectively. The difference in latency between ipsilateral and contralateral responses (6.9 ms) was statistically significant (n=15, $p<0.001$, t-test). The application of dCMS resulted in successive spinal motoneuronal responses picked up from the contralateral (to M1) electrode.

Figure 4C:
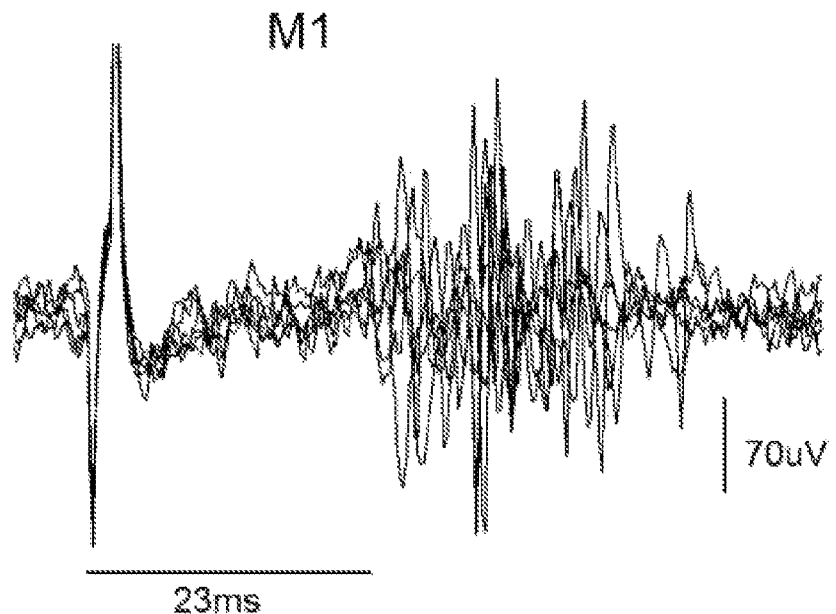
FIG. 4C is an illustration of six superimposed spinal responses after dCMS.

FIG. 4C shows six superimposed recorded traces. In FIG. 4C, three distinctive responses are seen, one with short latency (3.45±1.54 ms), the second with longer latency (6.02±1.72 ms), and a third with much longer latency (19.21±2.28 ms) (n=15). The latency of the ipsilateral (to M1) spinal motoneuronal responses (not shown) was 6.02±2.8 ms.

Figure 4D:
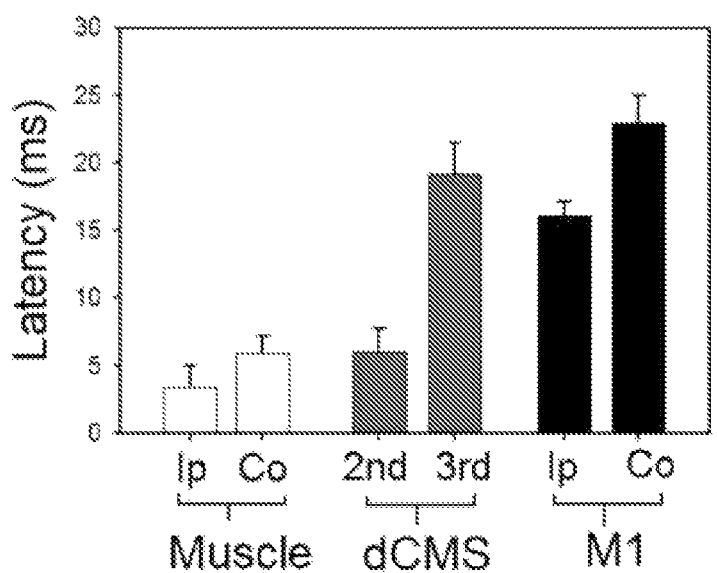
FIG. 4D is a graphical representation of the average latency of spinal responses after muscle stimulation, dCMS, and after M1 stimulation.

FIG. 4D summaries the average latencies collected during muscle, M1, and dCMS paradigms. Ipsilateral spinal response to M1 stimulation (Ip) was faster than the contralateral response (Co) ($p<0.05$). Muscle stimulation generated shorter response at ipsilateral motoneuron than the ones at the contralateral side ($p<0.05$).

5. Changes in Muscle Contraction and Spinal Responses During Dipolar Cortico-muscular Stimulation (dCMS)

The application of dCMS gradually increased the twitch peak force recorded from the gastrocnemii muscles and neuronal activity recorded from the spinal cord. Since the magnitude of these enhancements were similar in control and injured animals, only data obtained from SCI animals (n=9) are presented. The increase in the force of the contralateral muscle contraction is shown in FIGS. 5A and 5B.

Figure 5A:
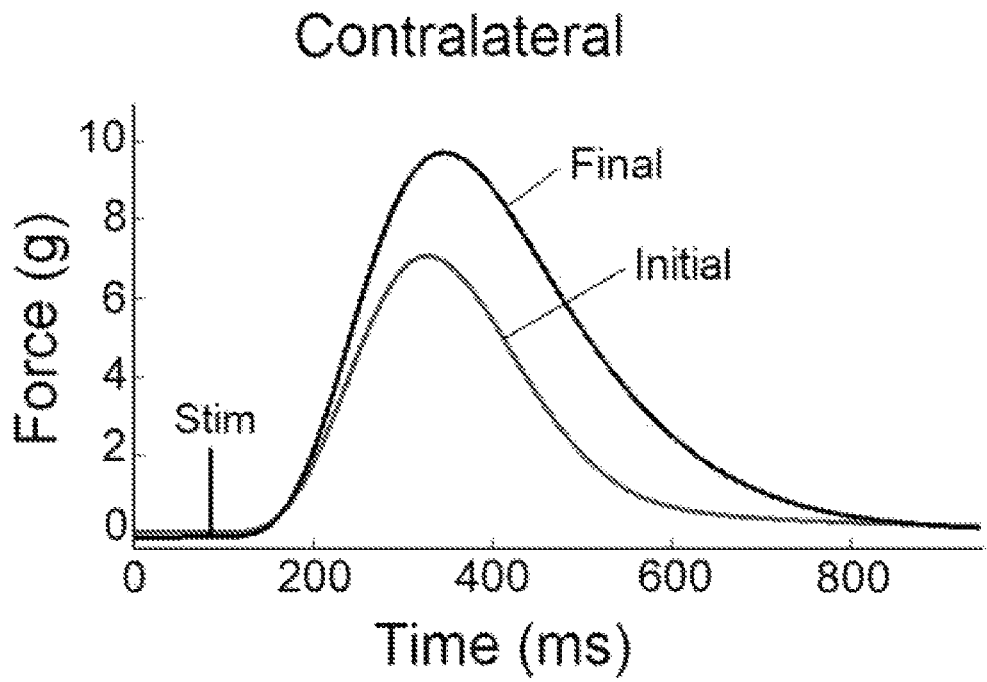
FIGS. 5A and 5B are graphical representations of contraction for the contralateral muscle during dCMS in animals with SCI.
Figure 5B:
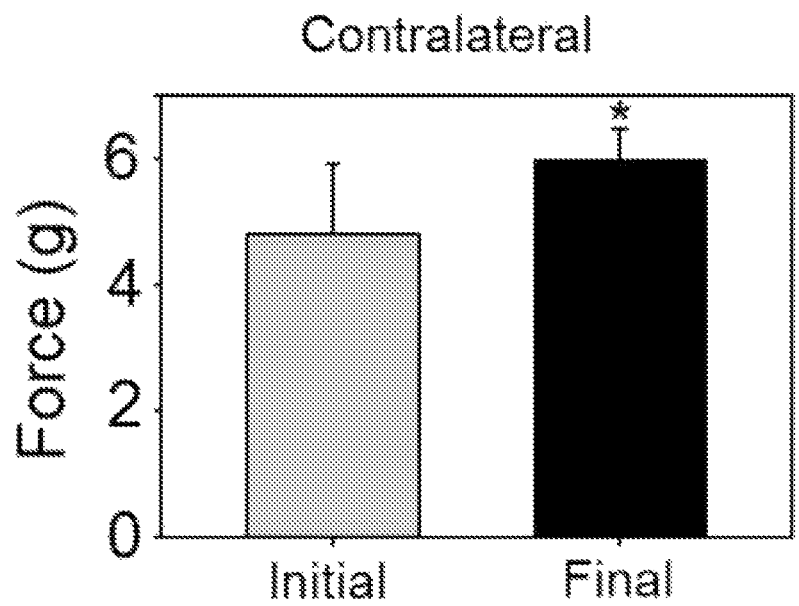

FIG. 5A shows that initial and final muscle twitches demonstrated greater twitch peak force at the end (final) than the beginning (initial) of dCMS on the contralateral muscle to stimulated M1. While FIG. 5A depicts representative recordings, the averaged results obtained from all 9 SCI animals are shown in FIG. 5B. The increase from an initial twitch peak force of 4.8±1.12 g to a final twitch peak force of 6.1±0.71 g was statistically significant (percent change=25.0±3.8%, p=0.001, paired t-test). The twitch peak force of ipsilateral muscle increased as well.

Figure 5C:
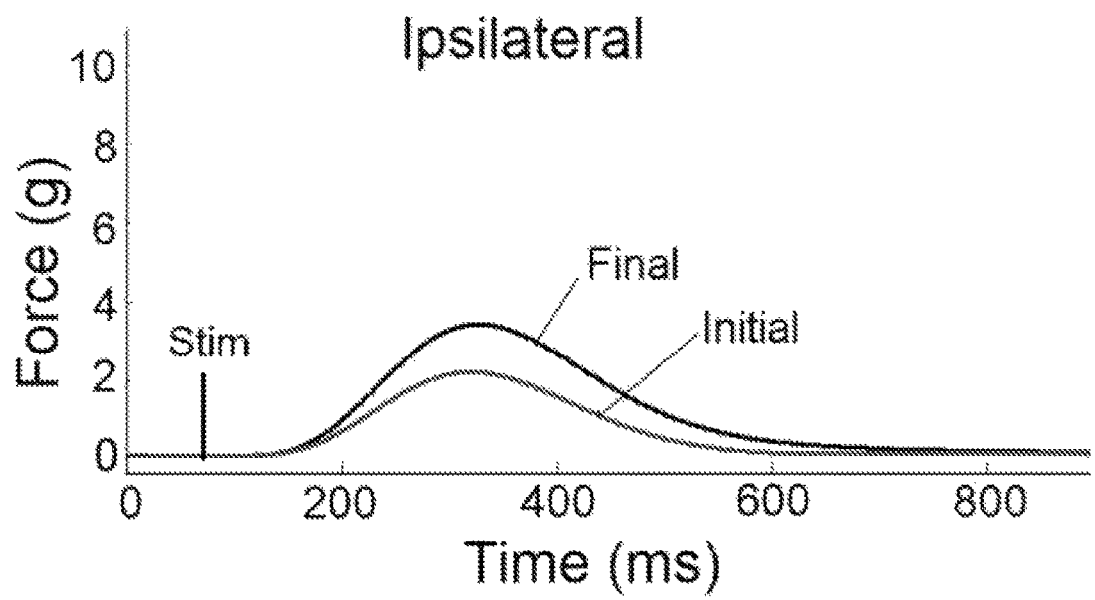
FIGS. 5C and 5D are graphical representations of contraction for the ipsilateral muscle during dCMS in animals with SCI.
Figure 5D:
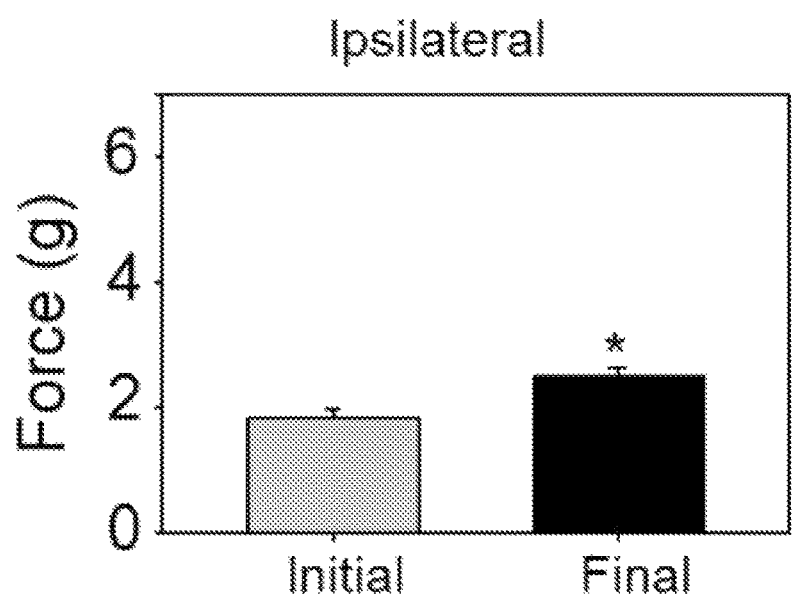

Representative recordings and averaged results are shown in FIGS. 5C and 5D. FIG. 5C shows initial and final muscle twitches of the ipsilateral muscle (to stimulated M1) during dCMS, which demonstrated an increase in twitch force in response to dCMS. FIG. 5D is a bar graph showing averages (n=9) of initial and final twitch peak force of the ipsilateral muscle. The final twitch force increased significantly from its initial value of 1.8±0.74 g (percent change=37.7±1.14%; p=0.001, paired t-test).

Similar results were obtained by comparing the first and the last spinal motoneuronal responses of the 100 pulses of dCMS protocol. On average, the contralateral (to stimulated M1) spinal motoneuronal responses showed significant increase (percent change=49.75±16.9%, p=0.013, one sample t-test), as did the ipsilateral (to stimulated M1) spinal motoneuronal responses (percent change=48.10±19.8%, p=0.04, one sample t-test). These findings suggest that physiological processes that mediate stronger connections of the corticomotoneural pathway were initiated during dCMS application.

Figure 6A:
FIGS. 6A and 6B show a plot of contralateral gastrocnemius muscle activity after dCMS (contaralateral) in animals with SCI.
Figure 6A:
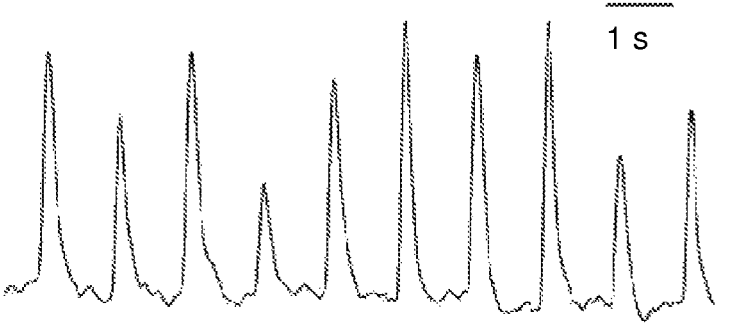
Figure 6B:
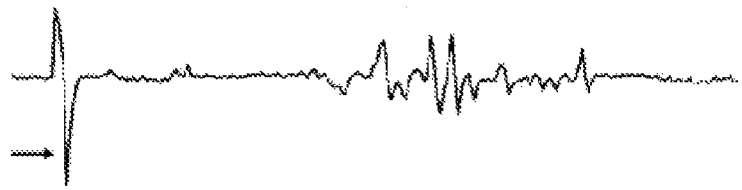
Figure 6B:
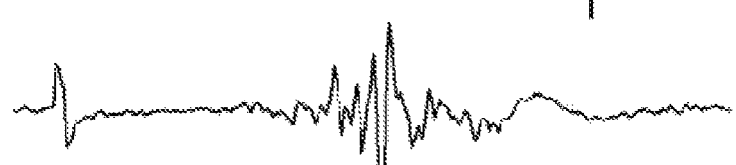
Figure 6C:
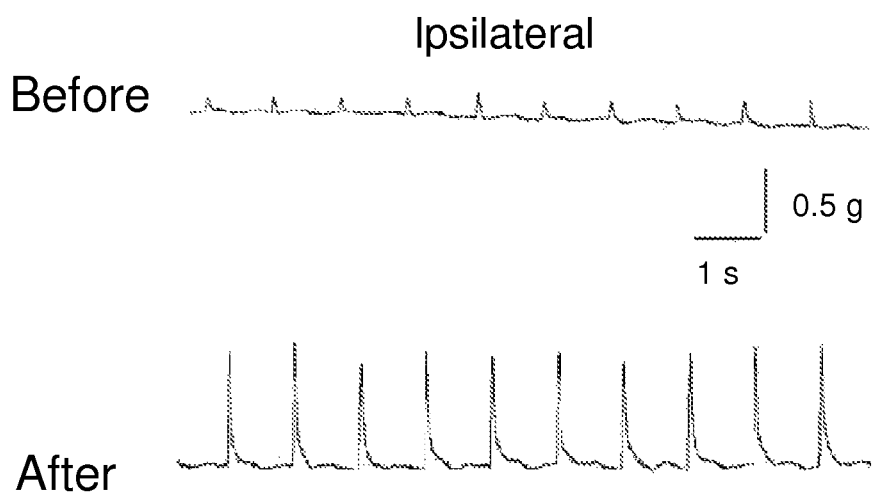
FIGS. 6C and 6D show a plot of contralateral gastrocnemius muscle activity after dCMS (contaralateral) in animals with SCI.
Figure 6D:
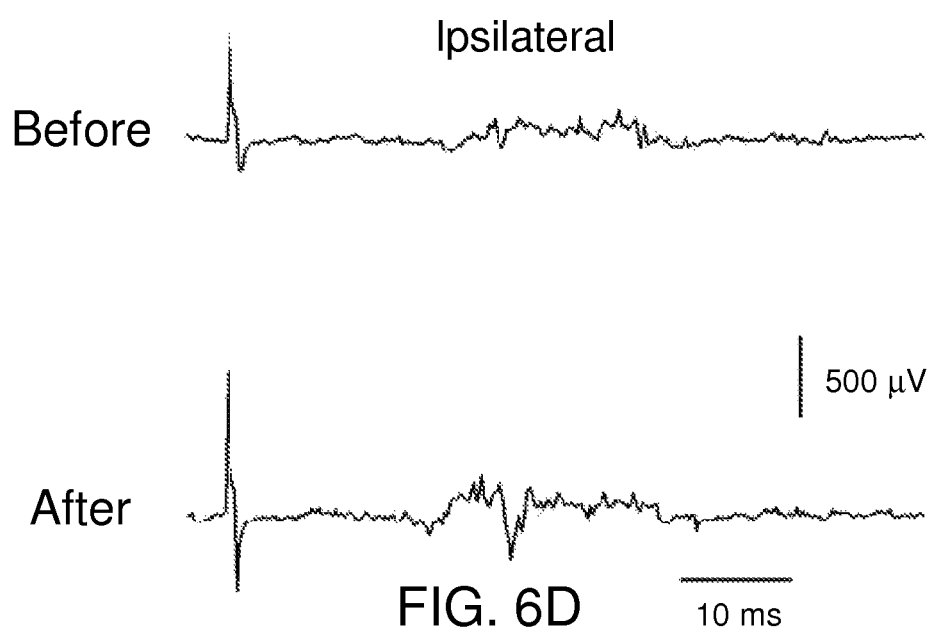

6. The Influence of dCMS Application on Muscle Twitches and Neuronal Activity in SCI Animals Cortically induced muscle twitches (measured as peak twitch force) were examined before and after dCMS in SCI animals. In all animals used in these experiments, twitch force was remarkably increased after dCMS. An example of twitches of the contralateral (to stimulated M1) (FIG. 6A) and ipsilateral (to stimulated M1) (FIG. 6C) gastrocnemius muscles before (upper panels) and after (lower panel) dCMS are shown in FIGS. 6A and 6C. The cortically induced spinal responses (measured as peak-to-peak) were also examined, which also substantially increased. Examples of contralateral (FIG. 6B) and ipsilateral (FIG. 6D) spinal responses are shown.

Figure 6E:
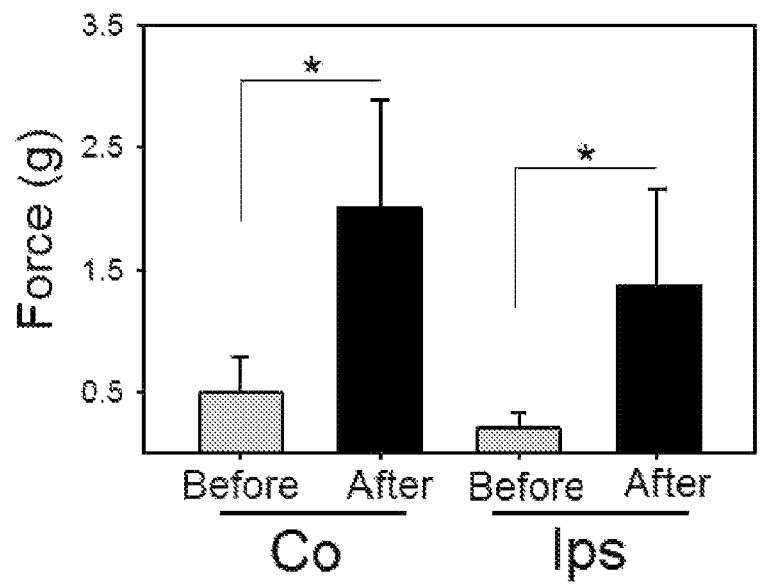
FIGS. 6E and 6F are graphical representations of muscle twitch force before and after dCMS in animals with SCI (contralateral and ipsilateral).
Figure 6F:
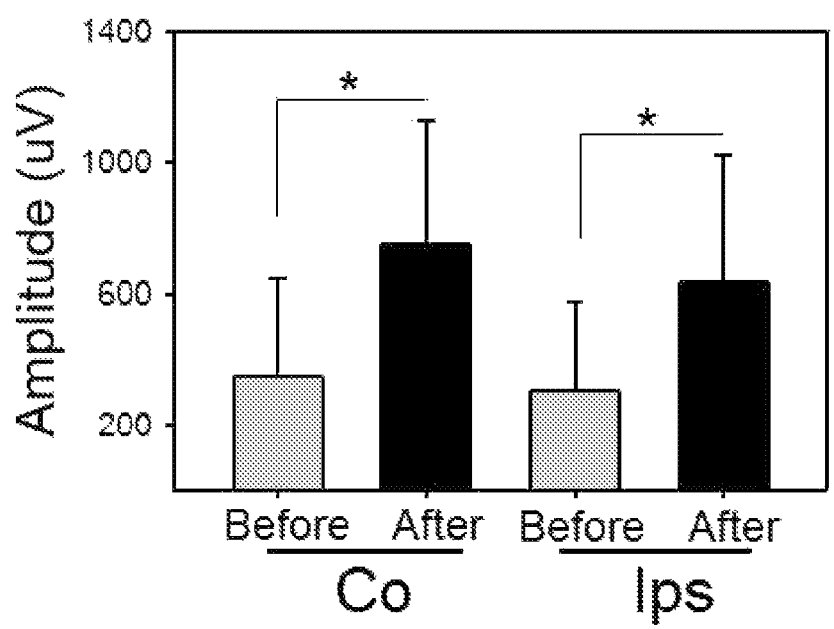

In FIG. 6E, the twitch peak force of the contralateral muscle showed significant increase (n=9; p<0.001) (average before=0.50±0.28 g vs. average after=2.01±0.80 g) after dCMS, as did the twitch peak force of the ipsilateral (to stimulated M1) muscle (average before=0.21±0.12 vs. average after=1.36±0.77, p<0.001, paired t-test). In FIG. 6F, spinal motoneuronal responses (n=9) contralateral (to stimulated M1) showed significant increase after dCMS (average before=347.67±294.68 μV vs. average after=748.90±360.59 μV, p=0.027, paired t-test) (increased by 313±197%), as did ipsilateral (to stimulated M1) spinal motoneuronal responses (average before=307.13±267.27 μV vs. average after=630.52-369.57 μV, p=0.001, paired t-test) (increased by 292±150%). Data are shown as means±SD. These results show that dCMS greatly potentiates the motor pathway in injured animals.

The maximal cortical threshold defined as the lowest electrical stimulus eliciting the strongest muscle twitch peak force was reduced from 9.4±0.89 V to =5.7±0.95 V after dCMS application (n=4, p<0.001, t-test). The muscle twitch force and the magnitude of spinal motoneuronal responses, evaluated 60 min after dCMS in 5 SCI animals, were still significantly elevated on both sides (repeated measure ANOVA followed with post hoc, p<0.001).

7. Effects of dCMS on the Nonstimulated Cortico-muscular Pathway in Animals with SCI The test stimulation of the other M1, contralateral to M1 where dCMS has been applied, revealed an increase of the contraction force recorded from contralateral and ipsilateral gastrocnemii muscles. The increase in contralateral (percent change=182.8±87.18%), and ipsilateral muscles (percent change=174.8±136.91%) was statistically significant (n=6, p<0.05, t-test).

Contralateral spinal motoneuronal response was increased significantly (p=0.006, t-test) (average percent change=373.8±304.99%), as did ipsilateral (average percent change=289.2±289.62%, p=0.025, t-test). These results indicate that even though dCMS was unilaterally applied, it affected the cortico-muscular pathway bilaterally.

Figure 7A:
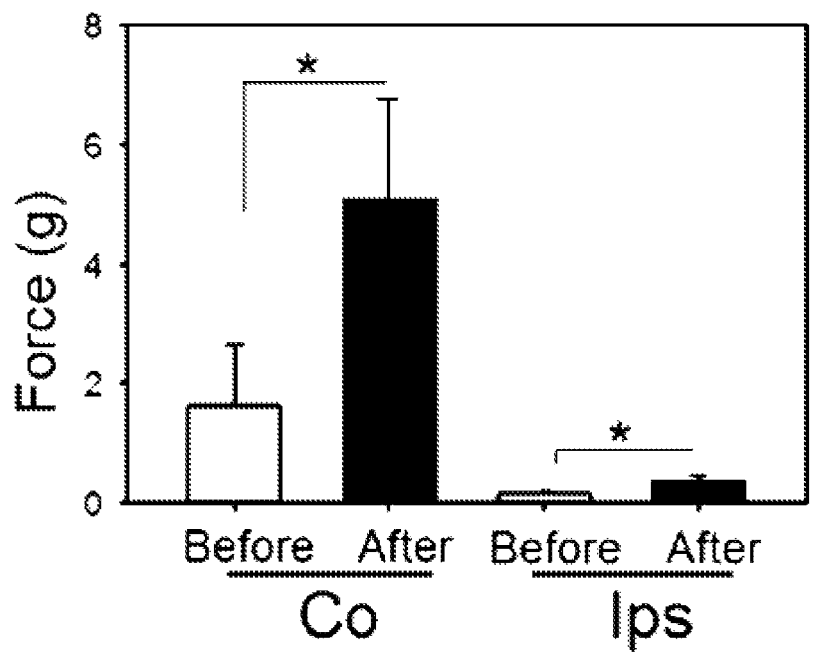
FIGS. 7A and 7B are graphical representations of muscle twitch force before and after dCMS in control animals.
Figure 7B:
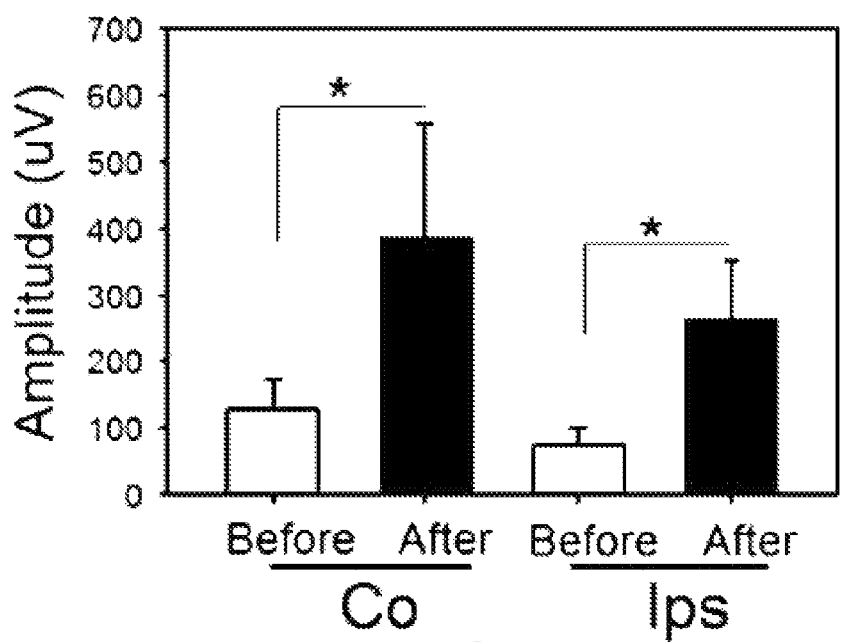

8 The Influence of dCMS Application on Muscle Twitches and Neuronal Activity in Control Animals The application of dCMS across the cortico-muscular pathway in control animals (n=6) resulted in an increase in the contraction force produced by both gastrocnemii muscles. FIGS. 7A and 7B show twitch force and cortically evoked spinal responses after dipolar cortico-muscular stimulation (dCMS) in normal mice. FIG. 7A is a quantification of results from 6 control animals, which revealed significant increase in contralateral (CO) and ipsilateral (Ips) (to stimulated M1) muscle twitch force after dCMS. FIG. 7B shows contralateral (to stimulated M1) cortically evoked spinal responses, which significantly increased after dCMS, as did ipsilateral responses. The twitch peak force of the contralateral muscle increased from 1.62±1.0 g before to 5.12±1.67 after dCMS application (percent change=250.75±129.35%, p=0.001, paired t-test, FIG. 7A). The twitch peak force of the muscle on the ipsilateral side increased as well, although the increase was less pronounced (from 0.16±0.05 g to 0.39±0.08 g, before and after dCMS, respectively (percent change=166.36±96.56%, p=0.001, paired t-test, FIG. 7A).

The amplitude of evoked responses recorded from spinal motoneurons was also enhanced by dCMS application. As depicted in FIG. 7B, the average amplitude of these spikes recorded at the contralateral side increased from 127.83±46.58 μV to 391.17±168.59 μV (percent change=168.83±152.00%, p=0.009, paired t-test). The increase at the ipsilateral side was even greater (percent change=369.00±474.00%, 77.50±24.73 μV before versus 267.00±86.12 μV after dCMS, p=0.007, paired t-test).

9. Comparison Between Control and SCI Animals

The cortically-induced twitches of the contralateral muscle, recorded from control animals were stronger than twitches observed in SCI animals regardless of whether they were recorded before (p=0.009, t-test), or after (p=0.001, t-test) the dCMS procedure. The response of ipsilateral muscles, however, was more complex. Before dCMS, SCI animals showed higher ipsilateral twitch peak force than control animals, although the difference was not statistically significant (p=0.39, t-test). This difference was significantly enhanced after dCMS intervention (p=0.01, t-test).

Similarly, before dCMS, the cortically-induced responses recorded from spinal motoneurons were higher in SCI animals at ipsilateral and contralateral sides, although the difference did not reach statistical significance (p=0.13, t-test). However, following dCMS, this difference was increased and became statistically significant (p=0.009, t-test).

Next a relative measure was obtained, which was characterized as a "fidelity index". Fidelity index (FI) is the normalized cortically induced spinal motoneuronal response to the corresponding muscle twitch peak force (spinal response/muscle twitch ratio). Lower fidelity index value indicates better association between spinal responses and their corresponding muscle twitches. In other words, it means better ability of a spinal response to induce muscle contraction. Therefore, changes in this index may indicate changes in relation between spinal and peripheral excitability.

Figure 8:
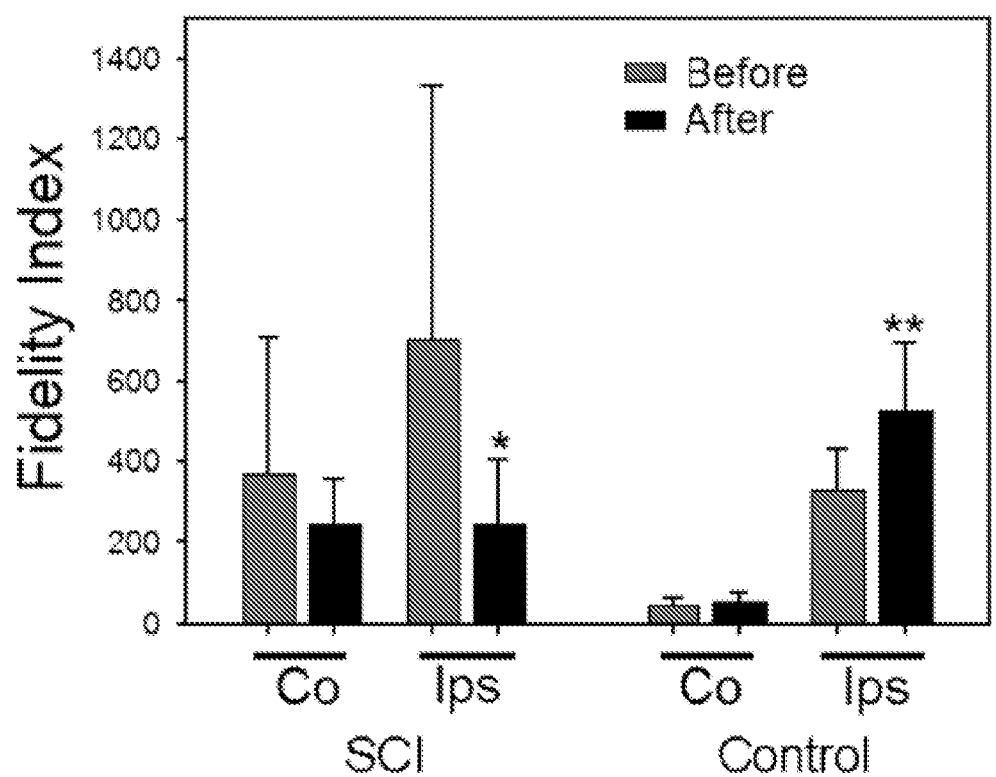
FIG. 8 is a graphical representation of a fidelity index analysis for animals with SCI and control animals.

After dCMS, SCI animals showed overall significant group reduction in FI (F=3.3, p<0.033, ANOVA) (FIG. 8). In FIG. 8, Solm-Sidak post hoc test showed reduction in FI in contralateral (average before=368.35±342.51 vs. average after=246.15±112.24), however, the difference was not statistically significant (p=0.46). The ipsilateral FI was significantly reduced after dCMS (average before=704.59±625.7 vs. average after=247.95±156.27) (p=0.011). The effect of dCMS treatment was the opposite in control animals which demonstrated overall group increase in FI after this procedure (F=31.51, p<0.001, ANOVA). FI was significantly increased after dCMS (Solm-Sidak post hoc, p<0.001) in the ipsilateral side (average before =328.53±104.83 vs. average after 526.83±169.36). There was also a trend reflecting an increase in the contralateral side (average before =48.59±17.71 vs. average after =56.15±24.19), but was not statistically significant (Solm-Sidak post hoc, p=0.89).

Comparing FI from control animals with FI from SCI animals showed a statistically significant lower index in the contralateral side of control animals (p<0.001, ANOVA, Solm-Sidak post hoc) both before and after dCMS. These results indicate that an inexcitability problem exists at the level of peripheral nerve and muscle.

10. Increase in Spinal Motoneurons Spontaneous Activity Due to dCMS

Figure 9A:
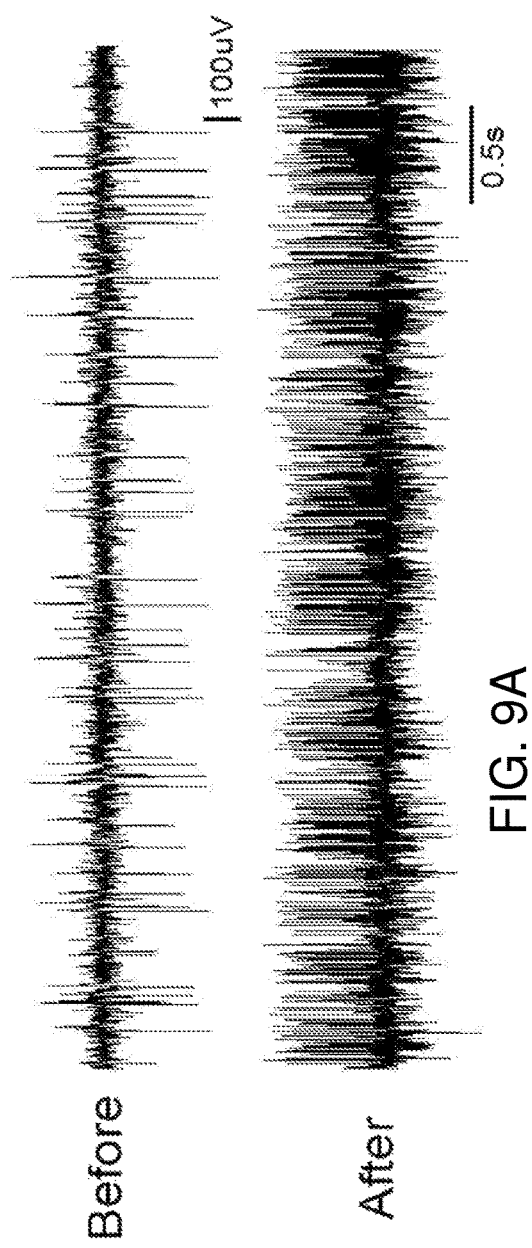
FIG. 9A shows a plot of spontaneous activity of spinal motoneurons before and after dCMS intervention.
Figure 9B:
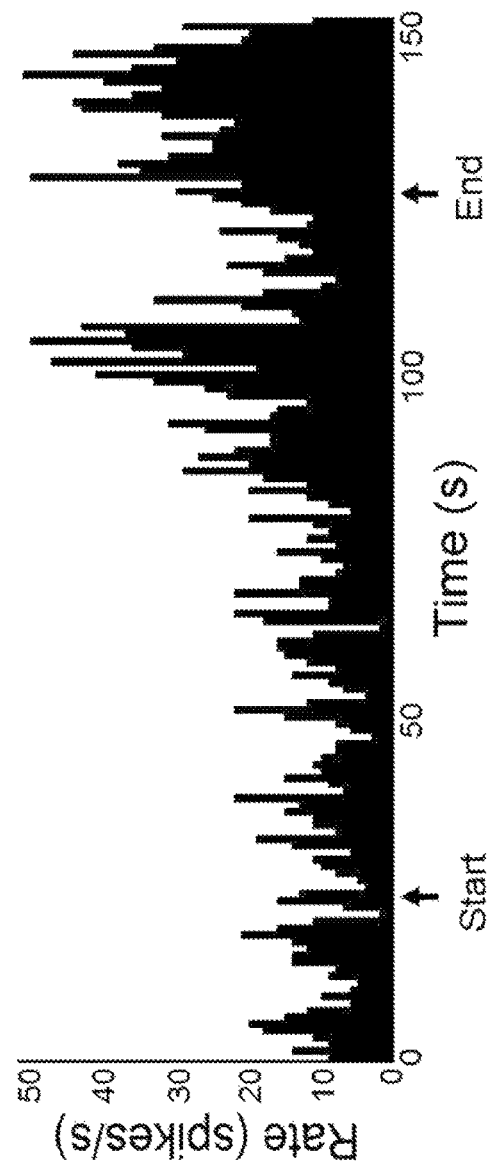
FIG. 9B is a graphical representation of firing rates during an entire experiment for an animal with SCI.
Figure 9C:
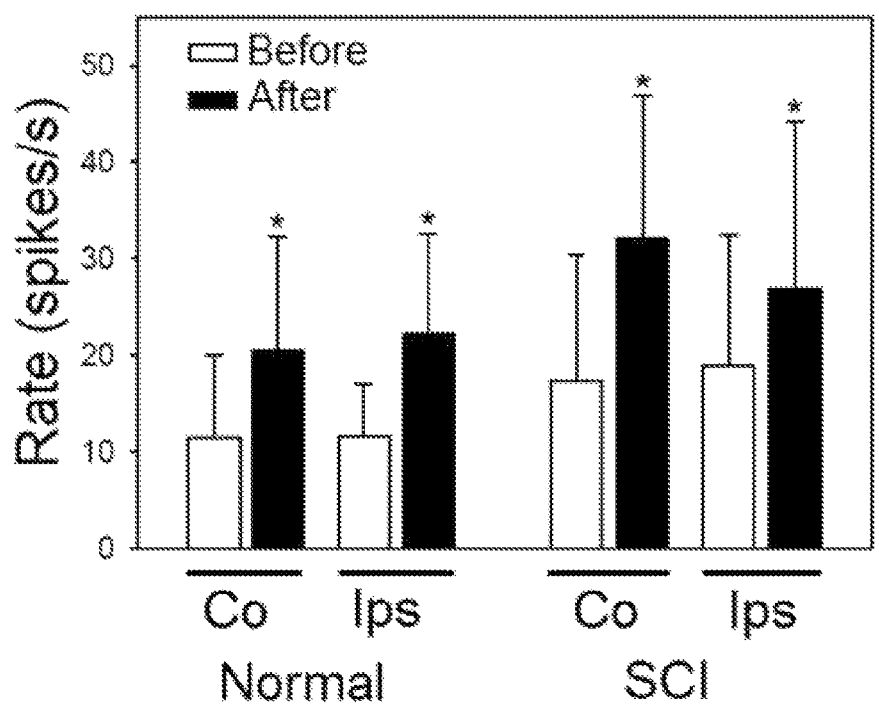
FIG. 9C is a graphical representation of firing rates before and after dCMS in control animals (contralateral and ipsilateral) and animals with SCI (contralateral and ipsilateral).

Comparing the firing rate of spontaneous activity before and after dCMS intervention demonstrated significant increase in both control and SCI animals. In FIGS. 9A and 9B, a representative spontaneous activity recording from an SCI animal is shown. In SCI animals, spontaneous activity was significantly increased in the contralateral side of the spinal cord (average before=17.31±13.10 spikes/s vs. average after=32.13±14.73 spikes/s; p=0.001) (121.71±147.35%), as it did in the ipsilateral side (average before=18.85±13.64 spikes/s vs. average after=26.93±17.25; p=0.008) (percent change=54.10±32.29%). In control animals, spontaneous activity was significantly increased in the contralateral (to stimulated M1) side of the spinal cord (average before=11.40±8.65 spikes/s vs. average after=20.53±11.82 spikes/s; p=0.006) (percent change=90.10±42.53%), as it did in the ipsilateral side (average before=11.63±5.34 spikes/s vs. average after=22.18±10.35 spikes/s; p=0.01) (percent change=99.10±1.10%). One way ANOVA showed no significant difference between control and SCI animals in firing rate, although, SCI animals demonstrated higher firing rate.

11. Effects of One Point (Monopolar) Stimulation of Muscle or Cortex

In order to determine that the effect was unique to dCMS, the influence of monopolar stimulation (maximal stimulation for 100 pulses, 1 Hz frequency) of either the muscle or the motor cortex on spinal motoneuronal response and muscle twitch peak force was examined.

As expected, muscle stimulation resulted in significant reduction in muscle twitch force (−20.28±7.02%, p<0.001, t-test) (n=5, 3 SCI and 2 control). It also resulted in a significant reduction in spinal motoneuronal responses evoked by the contralateral (to stimulated muscle) M1 test stimulation (average before=747.50±142.72 μV, vs. average after=503.14±74.78) (F=17.11, one way ANOVA, Solm-Sidak post hoc, p<0.001), however, no significant change was seen in responses recorded in the ipsilateral (to stimulated muscle) side of the spinal cord (average before 363.33±140.67 μV vs. average after=371.43±35.61, p=0.84).

In a separate group of animals (n=5, 3 SCI and 2 control), the effect of the monopolar stimulation paradigm applied only at the motor cortex on contralateral muscle twitch peak force and spinal motoneuronal response was tested. Both, the muscle twitch and motoneuron response were significantly reduced by over 50% (−53.69±4.3%, p=0.001, t-test) and almost 15% (−14.59±9.10%, p=0.003, t-test), respectively. These results indicate that one point muscle or cortical stimulation at maximal strength results in fatigue of muscle twitch force and reduction in spinal responses.

In general, the results show remarkable enhancement of the excitability of the motor pathway induced by unilateral application of dCMS. This enhancement was observed in control animals and in SCI animals that had severe locomotor impairment associated with signs of spastic syndrome. The effect was observed both in the ipsilateral and contralateral pathways. Maximal threshold of the ipsilateral cortex has been reduced. Improvement in muscle strength was accompanied by an increase in spontaneous activity and potentiation of evoked responses of the spinal motoneurons. Spinal motoneuronal responses and muscle twitches evoked by stimulation of the contralateral, non-treated M1 were significantly enhanced as well. The dCMS-induced effect persisted beyond the phase of stimulation and extended through the entire period of the experiment (60 min).

Figure 17A:
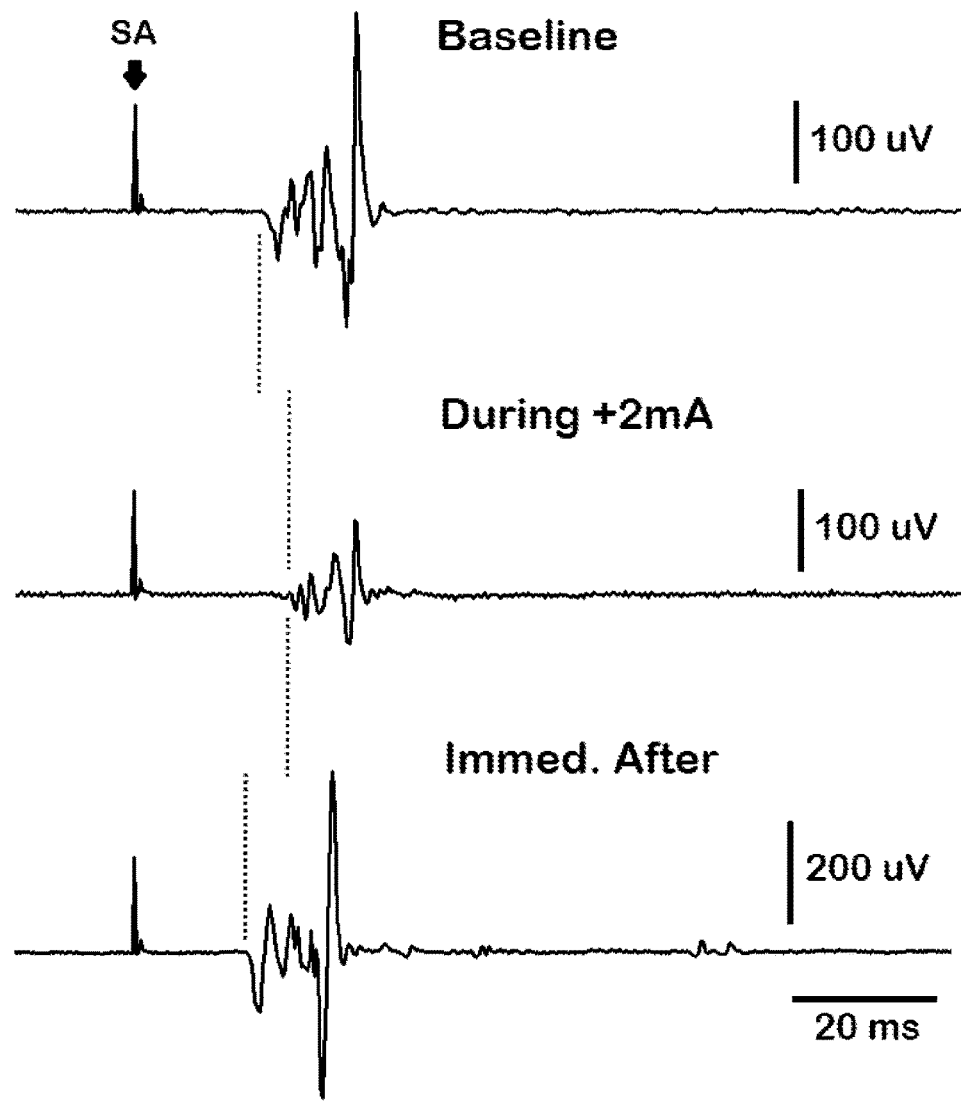
FIGS. 17A-17D demonstrate that tsDC induced changes in cortically-elicited tibial nerve potentials.
Figure 17B:
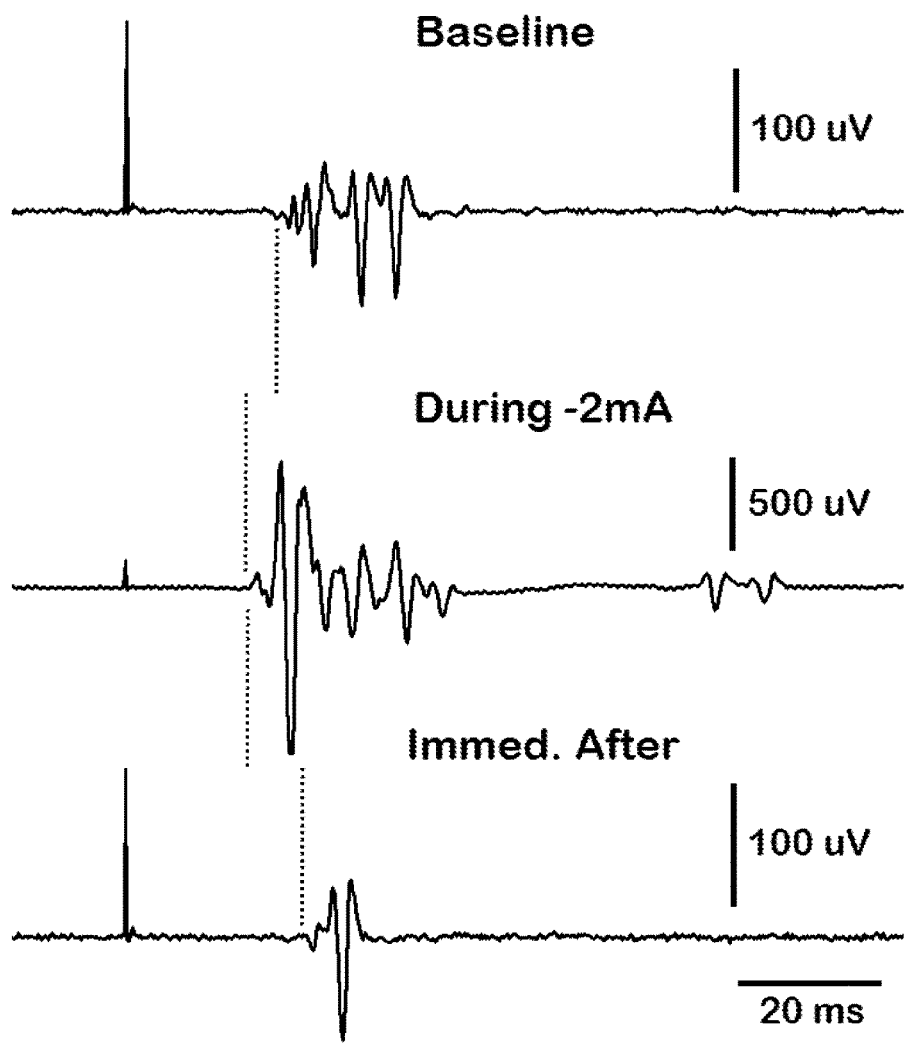
Figure 17C:
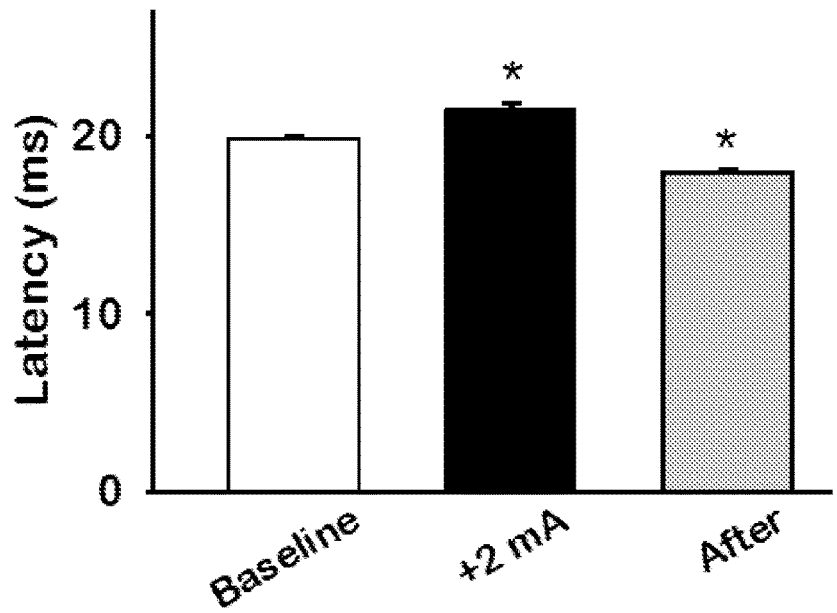
Figure 17D:
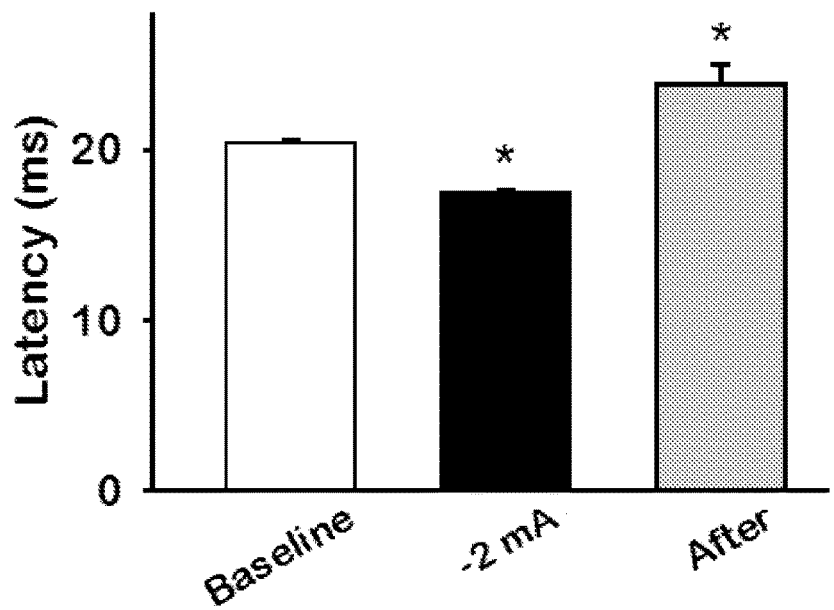

Bilateral responses to cortical stimulation have been routinely observed. They can be mediated by interhemispheric connections, ipsilateral cortico-spinal connections (5-6% of the contralateral projections), or commissural spinal neurons. As seen in FIGS. 17F and 18B, ipsilateral responses to unilateral stimulation of motor cortex evoked larger responses in SCI animals compared to controls. These results further support the idea that ipsilateral corticospinal projections are more efficient in evoking muscle contraction after SCI.

The mechanism of dCMS-induced increase in the efficiency of the motor pathway is not clear and one can only speculate what processes have been modulated. It is obvious that the potentiation in muscle force during dCMS is not like the potentiation seen after neuromuscular stimulation. See Luke R, Harris W, Bobet J, Sanelli L, Bennett D J, Tail Muscles Become Slow but Fatigable in Chronic Sacral Spinal Rats With Spasticity, J. Neurophysiol. 95:1124-1133 (2006). While neuromuscular stimulation leads to a brief potentiation of muscle force followed by a steep reduction in force, dCMS leads to a gradually proceeding increase in the amplitude of cortically-elicited muscle contraction. Since the enhancement occurred at contra- and ipsilateral sides, the locus of potentiation is most likely either spinal or supraspinal. The enhancement of cortically-elicited muscle contraction was accompanied by a reduction in maximal threshold to cortical stimulation, an increase in spinal motoneuronal responses, and an increase in cortically-elicited spinal motoneuronal responses. Therefore, one can assume that improvements occurred simultaneously at several functional levels of the corticomotoneural pathway.

In view of the fact that the current employed in the stimulation paradigm was always positive at one end and negative at the other, the stimulation can be considered in part polarizing. In the past, the paradigm of polarizing current was used to study excitability of different parts of the nervous system. See Landau W. M., Bishop G. H., Clare M. H., Analysis of the form and distribution of cortical potentials under the influence of polarizing currents, J. Neurophysiol. 27:788-813 (1964); Gorman A. L. F., Differential patterns of activation of the pyramidal system elicited by surface anodal and cathodal cortical stimulation, J. NeuroPhysiol. 29:547-64 (1965); Terzoulo C. A., Bullock T. H., Measurement of imposed voltage gradient adequate to modulate neuronal firing, Proc. Natl. Acad. Sci. USA, 42:687-694 (1956); Bindman L. J., Lippold O. C. J., Redfearn J. W. T., Long-lasting changes in the level of the electrical activity of the motor cortex produced by polarizing currents, Nature 196:584-585 (1962). In these studies, polarizing current produced potential membrane changes in which hyperpolarization occurs at cellular parts near the positive electrode and depolarization occurs near the negative electrode. Complying with this rule, for example, the situation of two polarizing electrodes on the spinal cord (one on the ventral side and the other on the dorsal side) produced changes in membrane and spike potentials of primary fibres from muscles. See Landau et al. supra.

The results of the above study suggest that the current is polarizing during the brief, steady moment of pulse duration (1 ms). Given the electrodes placement, in which negative at the muscle and positive at the cortex, the cell body of corticospinal neurons is expected to hyperpolarize and their nerve terminals depolarize. Moreover, spinal motoneurons expected to hyperpolarize at the cell body and dendrites, and depolarize at the neuromuscular junction.

According to cell topography relative to the applied electrical field, membrane potential changes are also expected to occur at intervening interneurons. These membrane changes that occur briefly during each pulse of dCMS, seem to prime corticomotoneural pathway for potentiation. In addition, the stimulating pulse has two more periods: rising (0.250 ms) and falling (0.250 ms). These changing periods caused a flow of current that exited from one end and entered at the other end of the corticomotoneural pathway. This idea is supported by the observation of stimulus artifact picked up by electrodes in the spinal cord. The current flowed throughout the entire pathway independent from the factors confounding active excitability (see introduction). This might cause activation of the corticomotoneural pathway at any possible excitable site/s. This will ensure eliciting spike-timing-dependent plasticity that might be one of the mechanisms that mediates the effect of the dCMS. See Dan Y, Poo M, Spiking Timing-dependent plasticity: From synapse to perception, Physiol. Rev., 86:1033-1048 (2006) for spike-timing-dependent plasticity.

In addition, the high frequency multiple spinal responses, evoked during dCMS, can, in principle, induce long-term potentiation. Because dCMS can engage a variety of neuronal mechanisms as well as non-neuronal activity, its effect might be a combination of many changes along the corticomotoneural pathway.

The dCMS-induced enhancement of muscle force has been observed both in control and injured animals. The mechanisms responsible for this amplification in these two groups of animals may overlap, but they do not have to be identical. Although, as discussed above the potentiating effect of dCMS could be mediated by strengthening synaptic responses, the nature and source of these changes may differ substantially in the motor pathway of control and injured animals. Axonal sprouting is probably the primary source of synaptic connections in the damaged spinal cord. See Murray et al. supra; Bareyre et al., supra; and Brus-Ramer et al. supra. However, axonal sprouting does not grant the formation of functional connections. Therefore, one of the probable mechanisms that may mediate the potentiating effect of dCMS is the refining and strengthening of the weak synaptic connections that have resulted from sprouting. Moreover, dormant connections that exist throughout the sensorimotor system may be activated and become functional after dCMS. See Brus-Ramer M., Carmel J. B., Martin J. H., Motor cortex bilateral motor representation depends on subcortical and interhemispheric interactions, J. Neurosci. 29:6196-206 (2009). Potentiating the spared normal connections could also happen after dCMS. While in control animals, potentiating of normal connections and facilitating dormant connections might be the only processes that mediate the effect of dCMS. The results show that dCMS stimulation was almost twice as effective in injured animals comparing with controls. This indicates that injured spinal cord is more prone for dCMS stimulation and posses extra mechanisms mediating the dCMS effect.

In SCI animals, even before the application of dCMS, the spinal motoneurons were responding more aggressively to cortical stimulation than controls. Nevertheless, very weak or no muscle contraction was seen (FIG. 6). This might be due to one of two mechanisms. One would be located in the spinal cord caudal to the lesion and/or the other being, the inexcitable peripheral nerves and/or the irresponsiveness of the muscle. Caudal to the lesion, the activity of the spinal motoneuron pool was probably desynchronized as a result of reorganization. Supporting this idea are the findings by Brus-Ramer and colleagues. See Brus-Ramer et al. supra. Bruce-Ramer et al. reported that chronic stimulation of corticospinal tracts resulted in preferential axonal outgrowth toward the ventral horn. This indicates that inter motoneuronal connections are dynamic processes, which may change by decentralization. Inexcitable peripheral axons were found in patients with SCI. See Lin C. S., Macefield V. G., Elam M., Wallin B. G., Engel S., Kiernan M. C., Axonal changes in spinal cord injured patients distal to the site of injury, Brain, 130:985-994 (2007). Assuming that the axons in SCI animals are in similar conditions, they could experience an action potential failure resulting in reduced muscle contraction. Muscle atrophy is always seen in animals with SCI and humans. See, for example, Ahmed Z., Wieraszko A., Combined effects of acrobatic exercise and magnetic stimulation on the functional recovery after spinal cord lesions, J. Neurotrauma, 25:1257-1269 (2008); Liu M., Bose P., Walter G. A., Thompson F. J., Vandenborne K., A longitudinal study of skeletal muscle following spinal cord injury and locomotor training, Spinal Cord, 46:488-93 (2008); Shah P. K., Stevens J. E., Gregory C. M., Pathare N.C., Jayaraman A., Bickel S.C., Bowden M., Behrman A. L., Walter G. A., Dudley G. A., Vandenbome K., Lowerextremity muscle cross-sectional area after incomplete spinal cord injury, Arch. Phys. Med. Rehabil. 87:772-778 (2006); Gordon T., Mao J., Muscle atrophy and procedures for training after spinal cord injury, Phys. Ther. 74:50-60 (1994). This might also be one of the reasons why spinal motoneurons responses were not translated adequately into muscle contraction.

The adequacy of motoneuronal responses was quantified by calculating the fidelity index, which is the ratio of spinal response to muscle twitch force. The dCMS-induced changes in fidelity index were opposite in control and injured animals. While this index has been reduced in injured animals, indicating improvement in the effectiveness of the motor pathway, it had increased in control animals suggesting lowering of the pathway effectiveness probably due to fatigue interference. Therefore, one can imply that injury to the spinal cord initiates processes which favor regeneration of the function. The dCMS procedure likely synchronizes and facilitates these processes, promoting recovery.

Before the dCMS application, the spontaneous activity of motoneurons in animals with SCI was higher than that of control animals. This and the exaggerated evoked spinal responses in animals with SCI, is consistent with the behavioral measurements that show spastic syndrome-like characteristics. The exaggerated spontaneous firing rate of spinal motoneurons is also consistent with data from motor unit firing in humans and animals after SCI and with results from intracellular recordings from sacrocaudal motoneurons that show sustained and exaggerated firing rate in animals with SCI. See, for example, Gorassini M., Bennett D. J., Kiehn O., Eken T., Hultborn H., Activation patterns of hindlimb motor units in the awake rate and their relation to motoneuron intrinsic properties, J. NeuroPhysiol. 82:709-717 (1999); Thomas C. K., Ross B. H., Distinct patterns of motor unit behavior during muscle spasms in spinal cord injured subjects, J. NeuroPhysiol. 77:2847-2850 (1997); Harvey J. P., Gorassini M., Bennett D. J., *The spastic rat with sacral spinal cord injury* in Animal model of movement disorders, edited by Mark LeDoux, El Sevier Academic Press, 691-697 (2005). Minutes after dCMS, motoneuronal spontaneous activity was still substantially increased. Some of these activities were coordinated, as shown in FIG. 3B, although most of the spontaneous activity was in un-modulated pattern of firing as shown in FIG. 9A. Voltage-dependent persistent inward currents (PICs) that strengthen synaptic inputs in normal behavior depend on descending brain-stem-released serotonin (5-HT) or noradrenaline. Here the increase in the spontaneous firing rate and the appearance of modulated activity in some animals after dCMS may indicate better connections with brain-stem centers.

Second Experiment (Employing iCENS)

In the second experiment, a 14 year old female with spastic quadriplegic cerebral palsy was treated with dipolar cortico-muscular stimulation (dCMS), which is a subspecies of iCENS, in the summer of 2009. She could not climb or descend stairs. She used a wheel chair for all indoor and outdoor locomotion. She needed maximal assistance just to stand for a few seconds. She had extremely tight, spastic, and weak distal muscles of the lower and upper extremities. She had disturbing clonuses (a rapid succession of flexions and extensions of a group of muscles, usually signifying an impairment of the brain or spinal cord).

She was treated with a total of six sessions over three weeks. Each session lasted for 30 minutes. Two first electrodes were connected to her left motor cortex and her right motor cortex. Multiple second electrodes were connected to her right inner wrist, her left inner wrist, her right fibular nerve ending, her left fibular nerve ending, the belly of her right calf muscle, the belly of her left calf muscle, her right sole, and her left sole. In a few sessions, some of the multiple second electrodes were not connected. A first electrical stimulation signal including unipolar positive electrical pulses with a duration of 400 microseconds was commonly applied to the two first electrodes connected to her motor cortexes at the frequency of 1 Hz. A synchronous second electrical stimulation signal having the opposite polarity, i.e., including unipolar negative electrical pulses, was commonly applied to each of the second electrodes. The second electrical stimulation signal was the mirror image signal of the first electrical stimulation signal as illustrated in FIG. 20. The amplitude of the first and second electrical stimulation signals was selected at a signal strength that initiated twitches in her limbs.

After 6 sessions of the dipolar stimulation spread into two weeks (30 minutes/session), the patient could climb 17 steps independently. As of January 2011, she can independently ascend and descend about 20 steps, and uses crutches for all her locomotive activities. She is getting faster and more independent. She is capable of maintaining a standing posture for indefinite time with stable posture. She improved her proactive and reactive balance reflexes. Compared to her status prior to the treatment, her distal muscles are much stronger, significantly less spastic, and almost of normal flexibility. In a blinded assessment, her neurologist reported significant reduction in her spasticity and clonuses.

The above results clearly show that dCMS is an effective method that enhances the excitability of the cortico-muscular connections in both animals and humans. Thus, the method of the present disclosure can be used in humans suffering after spinal cord injury, stroke, multiple sclerosis, and others. For example, the method of the present disclosure can be employed to strengthen or awaken any weak or dormant pathway in the nervous system as demonstrated in clinical trials.

Third Experiment (Employing iCENS)

In the third experiment, dCMS was applied a fourteen year old male with history of Erb's palsy (right upper limb) in the summer of 2009. The patient had very weak external rotator muscles of the shoulder. This was manifested as inability to externally rotate the right arm, inability to shrug the right shoulder, and the inability to lift the right arm beyond 100 degrees. The patient had no voluntary control over these muscles and could not rotate the shoulder outward. In addition, the shoulder external rotators were apparently moderately atrophied, which was determined by clinical observation. He also had weak grasping action of the right hand.

He was treated with a total of four sessions over four weeks. Each session lasted for 30 minutes. A first electrode was connected to his left motor cortex. A second electrode was connected to his right inner wrist. A first electrical stimulation signal including unipolar positive electrical pulses with a duration of 400 microseconds was commonly applied to the first electrode connected to his motor cortex at the frequency of 1 Hz. A synchronous second electrical stimulation signal having the opposite polarity was commonly applied to the second electrode. The second electrical stimulation signal was the mirror image signal of the first electrical stimulation signal as illustrated in FIG. 20. The amplitude of the first and second electrical stimulation signals and the electrical current through his body while the pulses were turned on were on par with the conditions in the second experiment described above.

After only 15 pulses the patient was able to rotate, with ease, the right shoulder externally, and the patient had sensation in the arm during movement. Subsequently, he passes pilot's physical examination. As of January 2011, all his impairment has been completely resolved, and he is not considered to be disabled.

Fourth Experiment (Employing iCENS)

In the fourth experiment, dCMS was applied a five-year-old boy with history of Erb's palsy (right upper limb) in the summer of 2009. The patient had severer disability in the right upper extremity than the fourteen year old male in the third experiment.

He was treated with a total of four sessions over four weeks. Each session lasted for 30 minutes. The same electrode configuration was used as in the third experiment.

After the treatment, the boy was able to lift his arm. He was able to move his right wrist, crawl with both hands, catch a ball with both hands. His impairment became substantially reduced.

Fifth Experiment (Employing iCENS)

In the fifth experiment, a nine-month-old baby girl with quadriplegic paralysis, which was caused due to chromosomal anomaly, was treated in the fall of 2010 with the same dCMS method as described in the second experiment. The child had been completely paralyzed without movement in the head, the neck, the trunk, and the upper and lower extremities.

Initially, she was treated with dCMS method as described in the second experiment. Her upper extremities twitched under pulsing electrical stimulation signals, but her lower extremities did not respond to the pulsing electrical stimulation signals. Over a course of three weeks, the child was treated in four dCMS treatment sessions that lasted about 15 minutes each. Due to the lack of response in the lower extremities to the dCMS stimulation signals, only the upper extremities were treated with the dCMS method. After the four sessions, the child was able to make movement in all directions in the upper extremities. She could also move her fingers in all directions and hold a toy. She could hold her head up and turn her head around.

Sixth Experiment (Employing iCENS)

In the sixth experiment, dCMS was applied a four-year-old boy with cerebral palsy in the summer of 2010. The cerebral palsy was manifested as tipping toes walking, frequent falls, inability to walk fasterm and slight form of crouch walking, i.e., his knees and hips bent while walking.

He was treated with a total of four sessions over four weeks. Each session lasted for 30 minutes. The same electrode configuration was used as in the third experiment.

After the treatment, all problems of this patient were completely resolved, and the boy was able to function completely normally.

Seventh Experiment (Employing aCENS)

In the seventh experiment, trans-spinal direct current (tsDC) stimulation, which is a subspecies of in-phase neural stimulation, was applied to mice. Using one disc electrode situated subcutaneously over the vertebral column from T10 to L1 and another at an extra-vertebral location (lateral abdominal aspect), the effects of anodal tsDC (a-tsDC) or cathodal tsDC (c-tsDC) were tested on spontaneous activity and amplitude of cortically-elicited triceps surae (TS) muscle twitches. In a different set of experiments, the effects of a-tsDC or c-tsDC combined with rCES were tested. The data below demonstrate a unique pattern of modulation of corticomotoneural pathway activity by tsDC.

This study aimed to test whether: 1) tsDC could modulate the spontaneous activity of spinal motoneurons in a polarity-dependent manner; 2) tsDC could modulate corticomotoneuronal transmission; and 3) repetitive cortical stimulation (rCES) could affect spinal cord responses to tsDC. Using one disc electrode situated subcutaneously over the vertebral column from T10 to L1 and another at an extra-vertebral location (lateral abdominal aspect), the effects of anodal tsDC (a-tsDC) or cathodal tsDC (c-tsDC) were tested on spontaneous activity and amplitude of cortically-elicited triceps surae (TS) muscle twitches.

Methods

Animals

Experiments were carried out in accordance with NIH guidelines for the care and use of laboratory animals. Protocols were approved by the College of Staten Island IACUC. Adult CD-1 mice (n=31) were used for this study. Animals were housed under a 12-h light-dark cycle with free access to food and water.

Surgical Procedure

Animals were anesthetized using ketamine/xylazine (90/10 mg/kg, i.p.), which has been reported to preserve corticospinal evoked potential. Anesthesia was kept at this level using supplemental dosages (~5% of the original dose) as needed, and animals were kept warm throughout the procedure by a lamp.

The skin covering the two hindlimbs, thoracic and lumbar spines, and the skull was removed. On one side, TS muscle was carefully separated from the surrounding tissue, taking care to preserve the blood supply and nerves. The tendon of each of TS muscle was threaded with a hook-shaped 0-3 surgical silk, which was then connected to force transducers. Tissue surrounding the distal part of the sciatic nerve was removed. Both the sciatic nerve and TS muscle were soaked in warm mineral oil.

A craniotomy was performed to unilaterally expose the primary motor cortex (M1; usually on the right side) of the hindlimb muscles, which is located between 0 to −1 mm from bregma and 0 to 1 mm from the midline. The dura was left intact. The exposed motor cortical area was explored with a stimulating electrode to locate the motor point from which the strongest contraction of the contralateral TS muscle was obtained with the weakest stimulus.

Electrodes

An active tsDC electrode (0.8 mm2) was situated over T10-T13; the reference electrode (Ref) was situated subcutaneously over the lateral aspect of the abdominal muscles. The surrounding tissue was removed from the sciatic nerve and TS muscle, and the TS muscle was connected to force transducers. A recording microelectrode (R) was inserted into the tibial nerve. A concentric stimulating electrode (S) was placed over the contralateral motor cortex. The spinal column and skull were rigidly supported using a clamping system (not shown).

DC was induced through a gold surface electrode (0.8 cm2; Grass Technologies, West Warwick, R.I., USA) situated over the vertebral column from T10-L1. A similar reference electrode (0.8 cm2) was situated over the lateral aspect of the abdominal muscles, as shown in FIG. 12. A layer of salt-free electrode gel (Parker Laboratories, Inc., Fairfield, N.J., USA) was applied between the electrodes and the tissue. Cortical stimulation was induced by a concentric electrode (shaft diameter, 500 μm; tip, 125 μm; FHC Inc., Bowdoinham, Me., USA), which was placed over the motor cortex presentational field of the TS muscle. Extracellular recordings were made from the TS branch of the sciatic nerve with pure iridium microelectrodes (shaft diameter, 180 μm; tip, 1-2 μm; resistance, 5.0 MΩ; WPI, Sarasota, Fla., USA). Tibial nerve potentials were recorded from the same location (about 3 mm from the TS muscle) in all animals. The proper location was confirmed by penetration-elicited motor nerve spikes, which were correlated with muscle twitches.

Muscle Force Recording

The hindlimb and the proximal end of the tail were rigidly fixed to the base of the apparatus. The knee was also fixed to the base to prevent any movements from being transmitted between the stimulated muscles and the body. The tendon of the TS muscle was attached to force displacement transducers (FT10, Grass Technologies), and the muscle length was adjusted to obtain the strongest twitch force (optimal length). The head was fixed in a custom-made clamping system. Animals were kept warm during the experiment with radiant heat.

Data Acquisition

Extracellular activity was passed through a standard head stage, amplified (Neuro Amp EX, ADInstruments, Inc., Colorado Springs, Colo., USA), filtered (bandpass, 100 Hz to 5 KHz), digitized at 4 KHz, and stored in the computer for further processing. A power lab data acquisition system and LabChart 7 software (ADInstruments, Inc.) were used to acquire and analyze the data.

Polarization and Stimulation Protocols

DC was delivered by a battery-driven constant current stimulator (North Coast Medical, Inc., Morgan Hill, Calif., USA). A pre-test of cortical stimulation consisting of 10 pulses delivered at 1 Hz (intensity, 5.5 mA; pulse duration, 1 ms) was used to elicit TS muscle twitches. The intensity of anodal tsDC was increased in 30-s steps (0.5, 1, 1.5, 2, 2.5, and 3 mA) over a total duration of 3 min. Thus, the maximal current density was 3.75 A/m2 (0.003 A/0.008 m2). To avoid a stimulation break effect, the current intensity was ramped for 10 s. During each tsDC step, a test (identical to the pre-test) was conducted; this test was repeated immediately (about 10 s) after termination of tsDC, and then again 5 and 20 min later. To avoid complications by excitability changes resulting from current applications, each a-tsDC and c-tsDC protocol was tested in different group of animals (n=5/group).

In addition, in two different groups of animals (n=5/group), paired stimulation was delivered, consisting of rCES (5.5 mA, 1 ms, 1 Hz, 180 pulses) combined with either a-tsDC (+2 mA) or c-tsDC (−2 mA). A pre-test and three post-tests (0, 5 and 20 min after) of cortical stimulation (5.5 mA, 1 ms, 1 Hz, 10 pulses) were also performed.

Control Experiments

To control for possible effects of conducting the testing procedure during tsDC, we performed experiments (n=3/group) in which only pre- and post-tests were conducted, but no tests were performed during tsDC stimulation. The procedure was performed identically to the procedure previously described, in which tsDC was increased in 30-s steps. In addition, to control for the possible tsDC-independent effects of rCES used in a paired stimulation protocol, we also performed experiments (n=2), in which rCES (180 pulses, 1 Hz) was performed alone.

Histological Analysis

After mice were exposed to a-tsDC (n=2) or c-tsDC (n=2), segments of spinal cord (~1 cm) located directly below the stimulating electrode were dissected for Hoechst stains to evaluate whether tsDC damaged spinal cord tissue. A similar spinal cord segment from an unstimulated control animal (n=1) was also analyzed. Tissues were kept overnight (4° C.) in 4% paraformaldehyde in 0.1 M PBS, then cryoprotected in 20% sucrose in PBS at 4° C. for 24 h. The spinal segments were freeze-mounted, cut into 30 μm sections, and placed on poly-L-lysine-coated glass slides. Sections were treated with Hoechst stain (5 μg/ml; Sigma) for 30 min, then washed with PBS four times. The sections were mounted and glass cover-slipped using mounting medium. Immunofluorescence was visualized using a Leica TCS SP2 confocal microscope with 405 and 488 nm lasers.

Injection of Glycine and GABA Blockers

Spinal cord segments (T13-L3) were exposed by laminectomy in anesthetized animals (n=2). The spinal column was clamped, and gastrocnemius muscles and sciatic nerves of both hindlimbs were exposed. The muscles were attached to force transducers, and recording microelectrodes and stimulating electrodes were situated as shown in FIG. 12. The spinal cord was injected at the level of L3-L4 with the inhibitory neurotransmitter blockers picrotoxin and strychnine (5 μM in 200 nl/2 min) using a microinjection pump (WPI, Sarasota, Fla., USA).

Calculations and Statistics

Cortically-elicited TS muscle twitches were calculated as the height of the twitch force relative to the baseline. The results of the pre-test, tests during tsDC, and post-tests were calculated as the average of 10 responses evoked at one Hz. Spike Histogram software (ADInstruments, Colorado Springs, Colo., USA) was used to discriminate and analyze extracellular spontaneous motoneuronal activity. Amplitude and frequency of spontaneous activity were measured as the average activity during a 20-s recording period before and at different points during and after stimulation. One-way ANOVA, repeated measures ANOVA, and Kruskal-Wallis one-way ANOVA on Ranks were used to test differences between the various treatment conditions. Post hoc tests (Holm-Sidak method or Dunn's Method) were then performed to compare cortically-elicited TS twitches at baseline or during paired stimulation with those post-stimulation. In addition, paired t-tests and Wilcoxon signed rank tests were used to compare the two treatment conditions. All data are reported as group means±standard error of the mean (S.E.M.). Statistical analyses were performed using SigmaPlot (SPSS, Chicago, Ill., USA) and LabChart software (ADInstruments, Inc.) with the level of significance set at $p<0.05$.

Results

Figure 13:
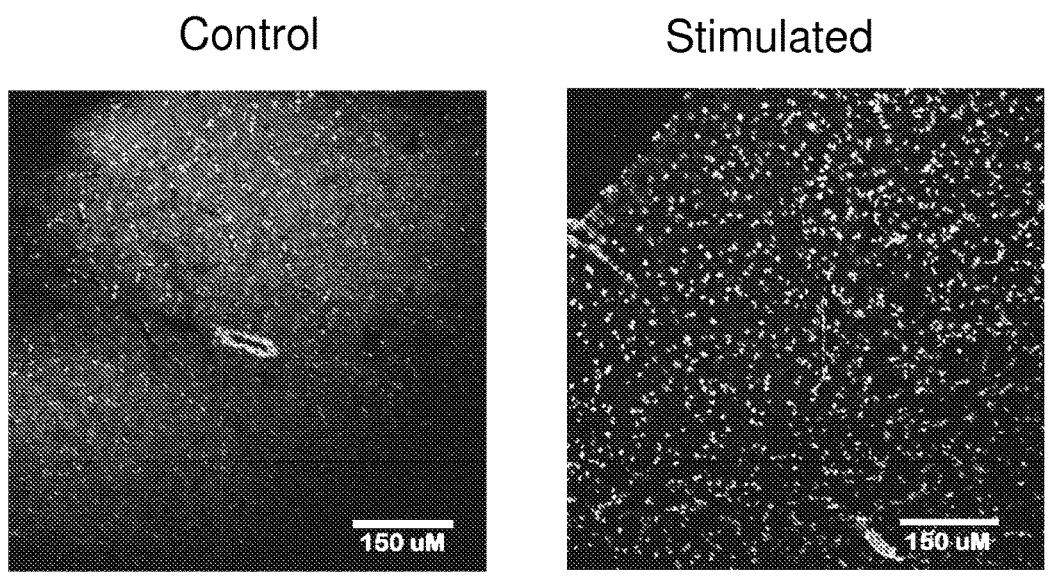
FIG. 13 shows Hoechst stains of transverse spinal cord sections from a segment (~1 cm in length) located directly under the stimulating tsDC electrode. Spinal cord sections from mice that received stimulation (right) were similar to sections from unstimulated controls (left), showing no evidence of morphological changes.

No morphological alterations were observed in the histochemical analysis of the spinal cord after a-tsDC or c-tsDC, as shown in FIG. 13.

1. tsDC Stimulation Modulates Spontaneous Activity of the Tibial Nerve

Figures 14A, 14B:
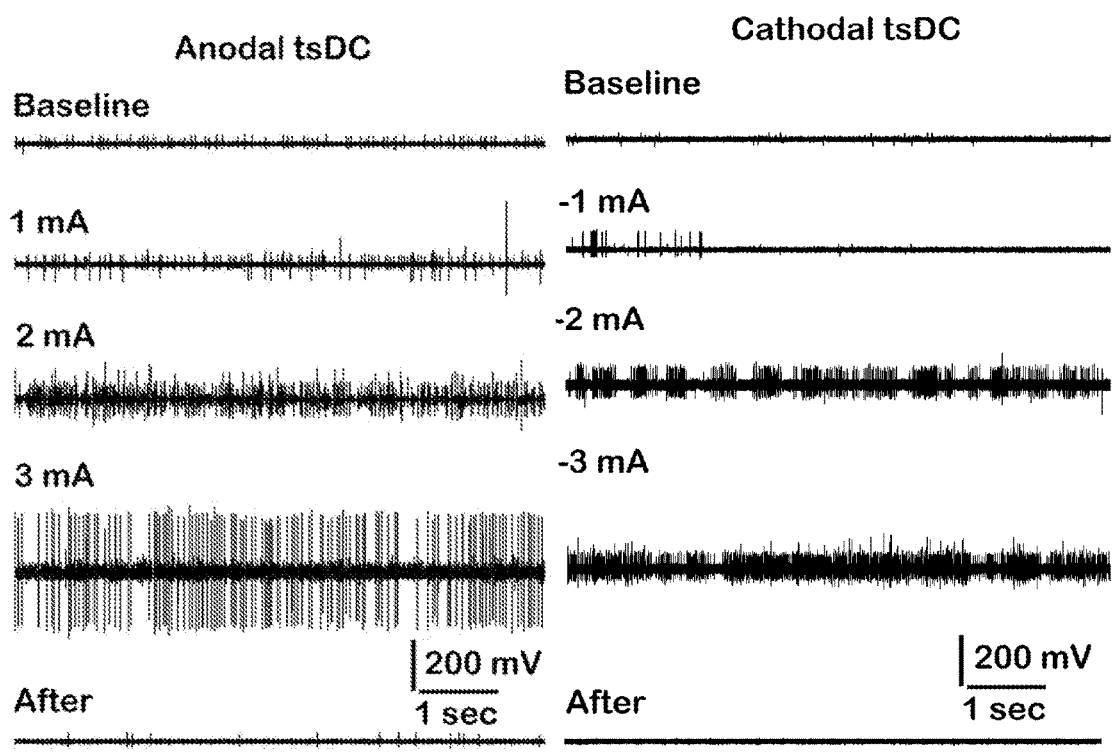
FIGS. 14A-14F illustrate that changes caused by tsDC in the frequency, amplitude, and pattern of spontaneous activity recorded from the tibial nerve.
Figure 14C:
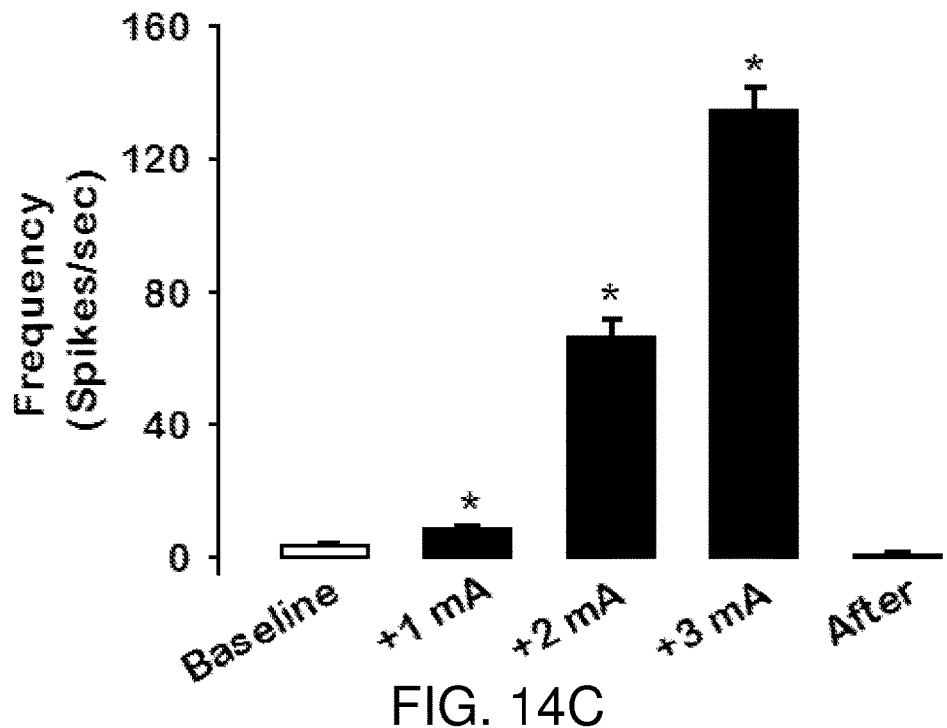
Figure 14D:
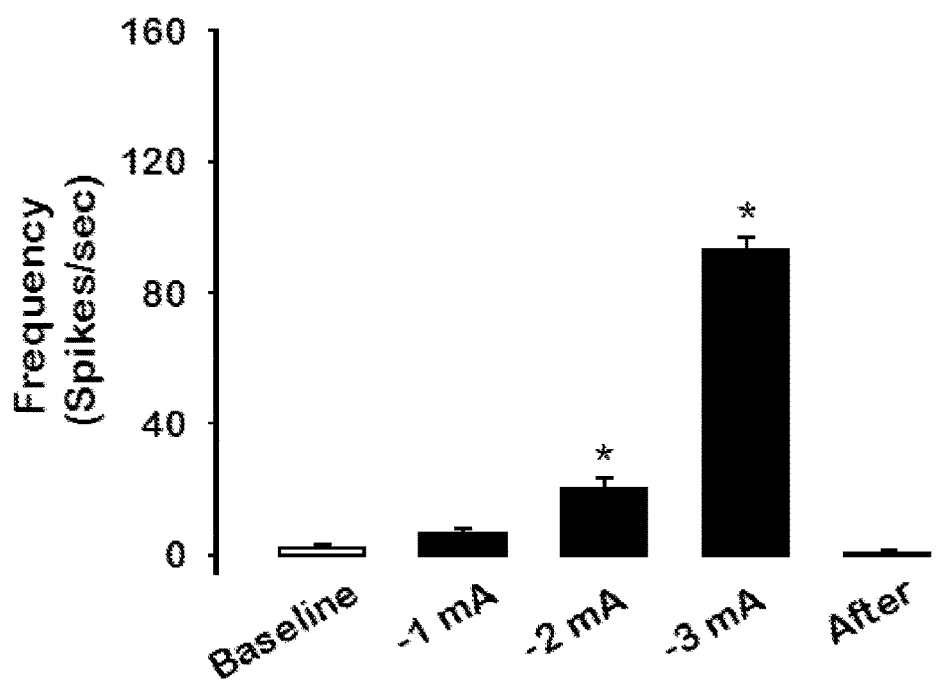

To characterize the effect of tsDC on spontaneous activity of spinal neurons, firing frequency was examined before, during and after tsDC, as shown in FIG. 14A (a-tsDC) and B (c-tsDC). As shown in FIG. 14C, a-tsDC increased the firing frequency from a baseline of 3.3±0.3 spikes/sec to 8.5±0.5, 66.5±4.9 spikes/sec, and 134.2±6.7 spikes/sec at +1, +2, and +3 mA, respectively, yielding a significant effect of condition (repeated measures ANOVA). Immediately following the termination of a-tsDC, the spontaneous firing frequency returned to baseline levels. As shown in FIG. 14D, c-tsDC increased the firing frequency from a baseline of 2.2±0.6 spikes/sec to 6.5±3.0, 20.1±3.1 spikes/sec, and 93.1±3.8 spikes/sec at −1, −2, and −3 mA, respectively, yielding a significant effect of condition (repeated measures ANOVA). Immediately following the termination of c-tsDC, spontaneous firing frequency returned to baseline levels, was not statistically significantly different from baseline ($p>0.05$).

The a-tsDC effect on spontaneous firing frequency was significantly greater than that of c-tsDC (Kruskal-Wallis ANOVA). Post hoc tests revealed that all three a-tsDC intensity steps induced significantly higher changes in the frequency of spontaneous activity compared to the changes induced by corresponding intensities of c-tsDC (p<0.05).

Figure 14E:
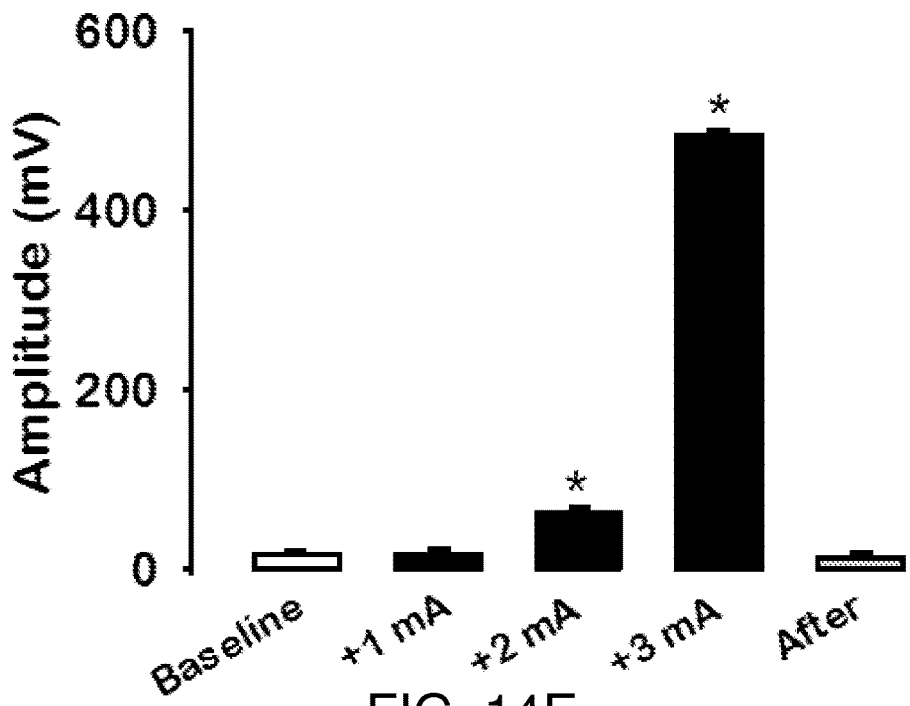
Figure 14F:
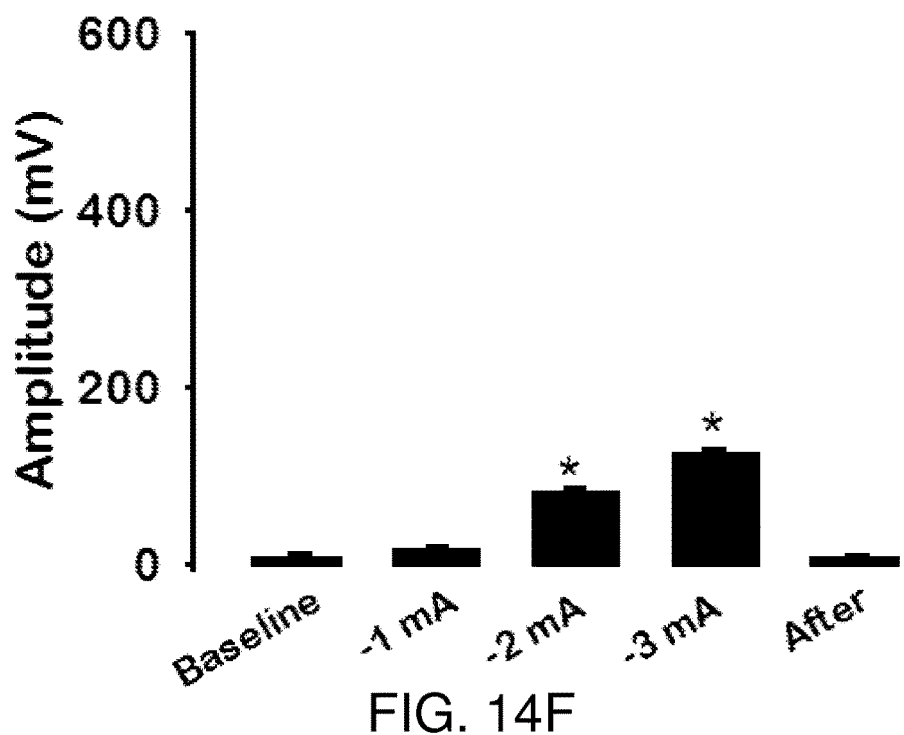

Changes in spike amplitude recorded during different intensities and polarities of tsDC were recorded across conditions (at baseline, at each intensity step, and after tsDC was terminated). Repeated measures ANOVA showed a significant overall effect of condition on the amplitude of activity recorded during baseline (16.8±0.3 mV), which increased during a-tsDC steps (step of +1=16.7±0.5 mV; step of +2=63.2 mV; step of +3=484.2±3.5 mV), then decreased after termination (11.9±0.7 mV), as shown in FIG. 14E. Subsequent post hoc tests showed that spike amplitude of activity recorded during intensity steps +2 mA and +3 mA were significantly higher than baseline activity (p<0.05). Repeated measures ANOVA also showed a significant overall difference in the amplitude of activity recorded at baseline (7.0±0.3 mV), during c-tsDC (step of −1=17.3±1.5 mV; step of −2=80.4±2.2 mV; step −3=123.7±4.3 mV), and after termination (5.6±0.29 mV), as shown in FIG. 14F. Subsequent post hoc tests showed that the amplitude of activity recorded during steps of −2 mA and −3 mA was significantly higher than baseline (p<0.05).

These findings suggest that a higher intensity of tsDC can recruit more spinal neurons or potentially more classes of spinal neurons. Furthermore, the differences between amplitudes of activity recorded during a-tsDC of +2 mA and c-tsDC of −2 mA and between a-tsDC of +3 mA and c-tsDC of −3 mA were statistically significant (t tests, p's<0.001). Overall, these findings indicate that a-tsDC and c-tsDC affect spinal neuron excitability through different mechanisms.

Figure 15A:
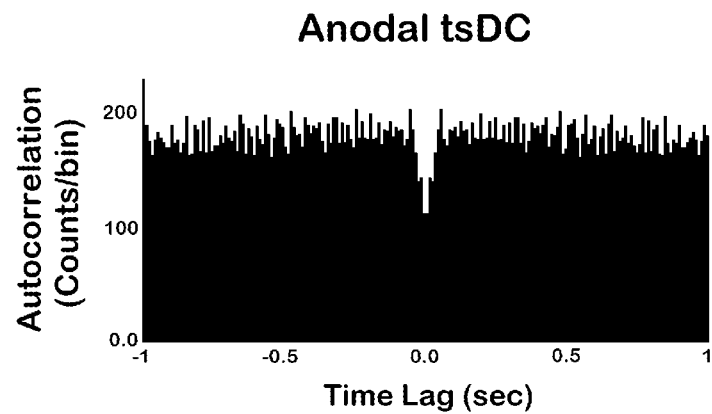
FIGS. 15A-15C show that cathodal stimulation may access rhythm-generating circuitry in the spinal cord.
Figure 15B:
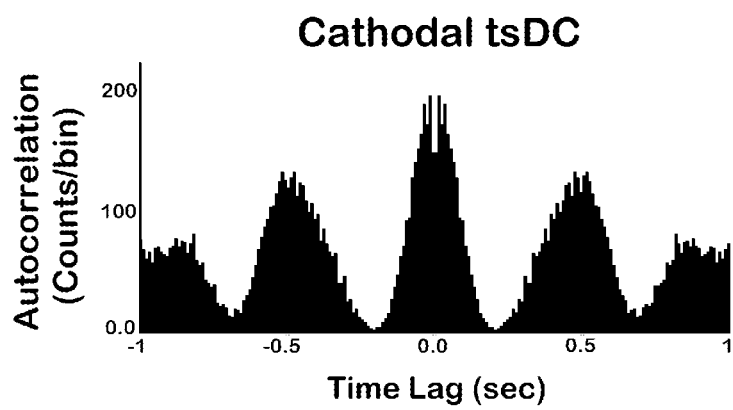
Figure 15C:
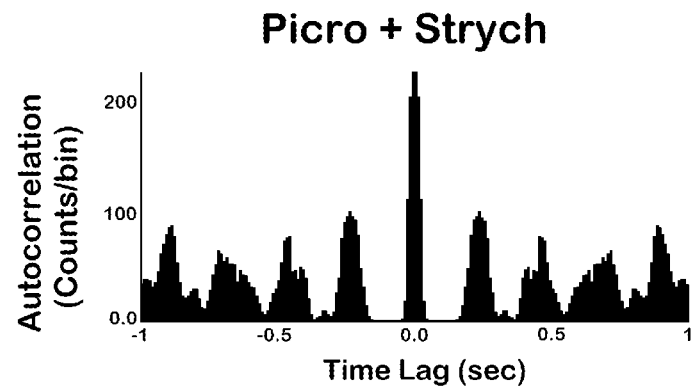

To further investigate the differential effects of a-tsDC and c-tsDC on spontaneous activity, we generated autocorrelograms for activity induced by these two conditions, as well as by injection of glycine and GABA receptor blockers. The results show tonic activity with no bursting or oscillation during a-tsDC, as shown in FIG. 15A. Conversely, c-tsDC induced bursting, as well as oscillatory activity, as shown in FIG. 15B. Similar to c-tsDC, glycine and GABA receptor blockers induced bursting and oscillatory activity, as shown in FIG. 15C. This similarity indicates that c-tsDC and glycine and GABA receptor blockers may share a mechanism of effect, which involves rhythmic-generating circuitry in the spinal cord.

2. tsDC Modulated Cortically-elicited TS Twitches

Figure 16A:
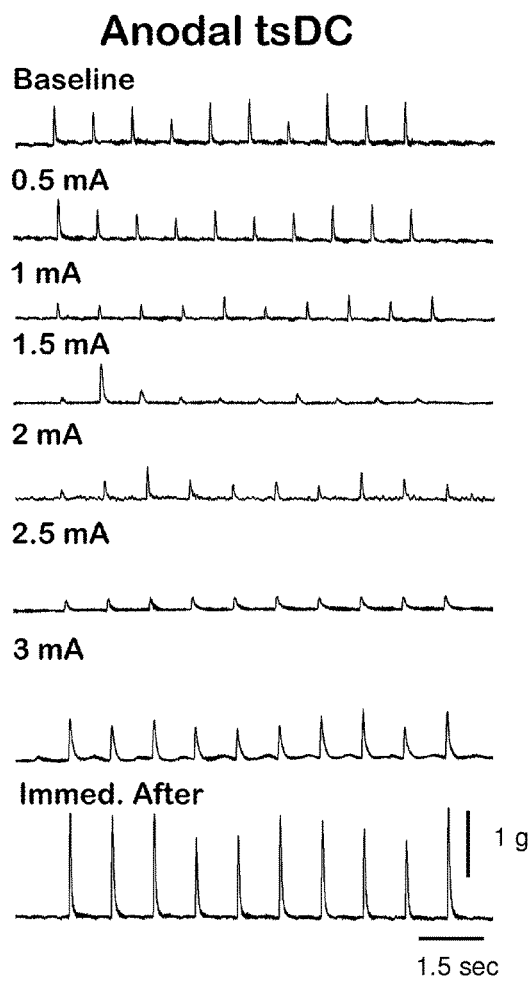
FIGS. 16A-16D illustrate that a-tsDC and c-tsDC differently modulated cortically-elicited TS twitches.
Figure 16B:
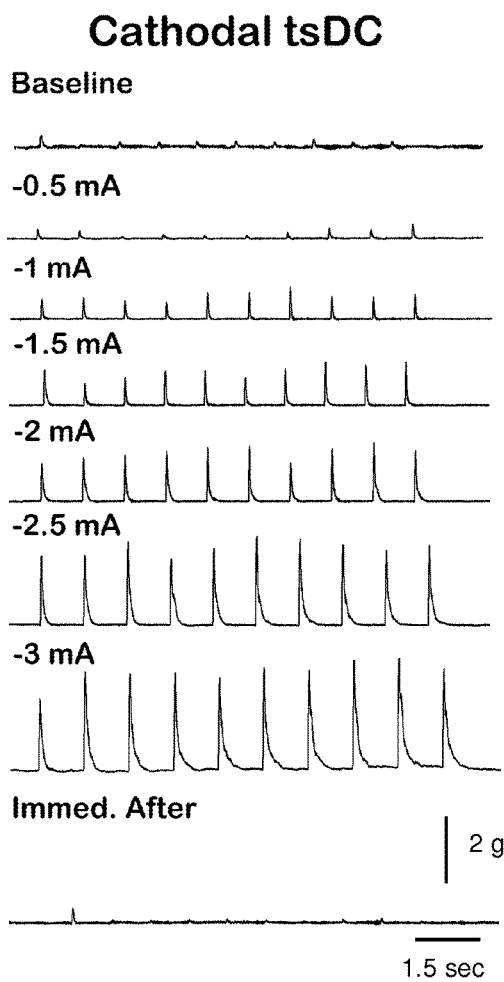
Figure 16C:
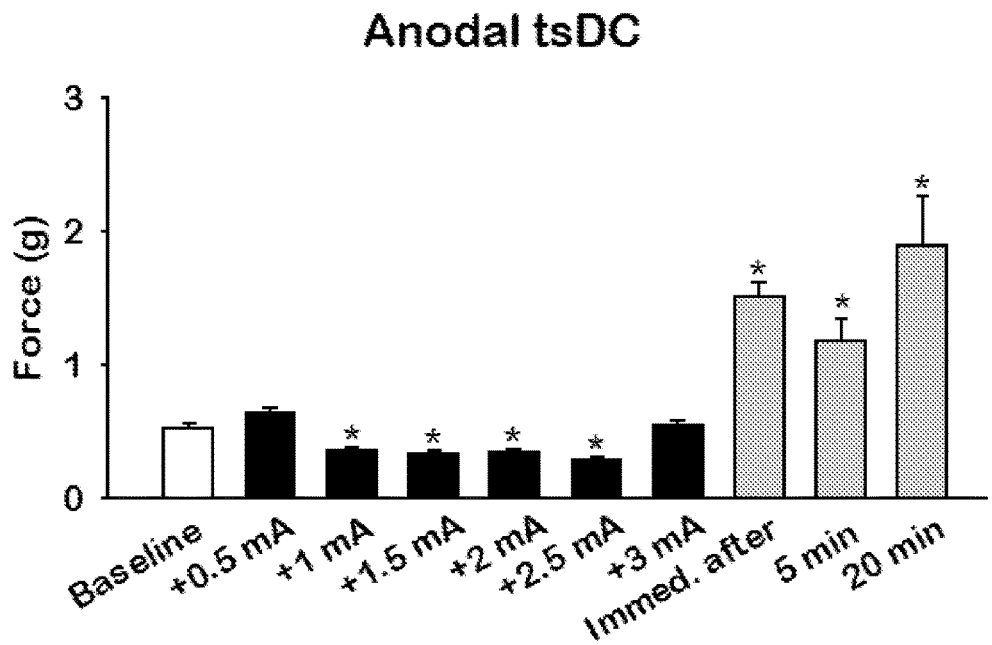

To address whether tsDC could modulate cortically-elicited TS twitches in an intensity- and polarity-dependent manner, TS twitches were elicited by stimulating the motor cortex before stimulation, at five intensity steps during tsDC, and after stimulation (at 0, 5, and 20 min). Repeated measures ANOVA, combined with post hoc tests, showed that a-tsDC affects the ability of the motor cortex to elicit TS twitches (p<0.001). Examples are shown in FIG. 16A. As shown in FIG. 16C, the baseline average of TS twitch peak force was 0.52±0.04 g, which was depressed to 0.35±0.02 g, 0.32±0.01 g, 0.34±0.02 g, and 0.28±0.01 g at intensities of +1 mA, +1.5 m, +2 mA, and +2.5 mA, respectively. In contrast, immediately after termination of a-tsDC, cortically-elicited TS twitches were significantly improved (1.51±0.12 g), and this improvement persisted at 5 min (1.20±0.15 g), and at 20 min (1.9±0.38) after a-tsDC.

In the a-tsDC group, there was a main effect of group (F=19.60, p<0.001, repeated measures ANOVA), and post hocs showed that TS twitches were significantly weaker during intensities 1 to 2.5 mA and were significantly stronger at all three time points after a-tsDC, compared to baseline. In the c-tsDC group, there was also a main effect of group (F=489.60, p<0.001, repeated measures ANOVA), and post hocs showed that TS twitches were significantly stronger during intensities −1 to −3 mA and significantly weaker afterwards, compared to baseline. Error bars represent S.E.M. *p<0.05 relative to baseline.

Figure 16D:
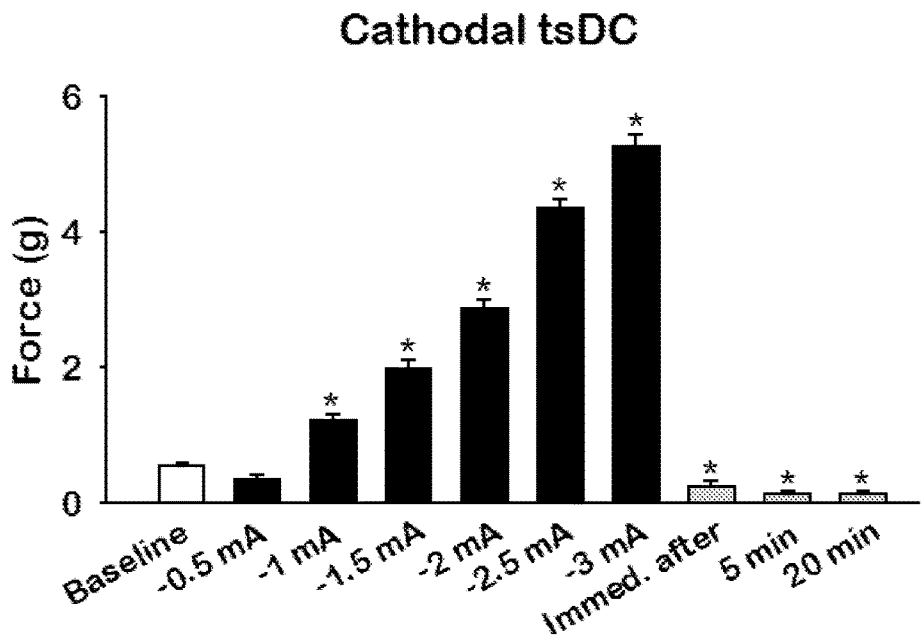

Compared to a-tsDC, the application of c-tsDC had an opposite effect on cortically-elicited twitches. Repeated measures ANOVA, combined with post hoc tests, showed a significant enhancement of cortically-elicited TS twitches during c-tsDC and depression after c-tsDC. Examples are shown in FIG. 16B. As shown in FIG. 16D, the average baseline TS twitch peak force was 0.53±0.04, which was enhanced to 1.23±0.08 g, 1.98±0.13 g, 2.88±0.13 g, 4.35±0.14 g, and 5.28±0.17 g at −1 mA, −1.5 mA, −2 mA, −2.5 mA, and −3 mA, respectively. A depressive effect was seen after termination of c-tsDC with a peak force of 0.23±0.10 g, 0.12±0.12 g, and 0.12±0.012 g at 0, 5, and 20 min, respectively. Taken together with the a-tsDC results, these data indicate that trans-spinal application of direct current can modulate the ability of the motor cortex to elicit activity at the level of the lumbar spine. This modulation depends on the polarity and intensity of the stimulation, as well as the timing of test relative to stimulation.

3. Testing Procedure Did not Change tsDC After-effects

To investigate a possible effect of conducting the testing procedure during a-tsDC or c-tsDC, we repeated these experiments (n=3/group) with only pre- and post-tests, but no tests during the tsDC stimulation. For a-tsDC, there was no significant difference between conditions that included or excluded testing during the a-tsDC stimulation (H=5.3, p=0.06, Kruskal-Wallis ANOVA). In conditions with and without testing during stimulation, a-tsDC induced immediate improvement of TS twitches (301.14±49.33% vs. 366.9±46.9%), which persisted after 5 min (229.59±66.03% vs. 325.9±170.14%), and 20 min (387.87±117.13% vs. 299.6±137.57%). Similarly, there was no effect of the testing procedure on the c-tsDC depressive after-effect (H=5.3, p>0.05, Kruskal-Wallis ANOVA). In conditions with and without testing during stimulation, c-tsDC depressed cortically-elicited TS twitches immediately (33.48±6.40% vs. 17.65±6.40%), after 5 min (21.24±3.8% vs. 25.45±2.98%), and after 20 min (23.95±3.44% vs. 25.35±3.0%). These results confirm that the testing procedure used in this study had no effect on the after-effects induced by a-tsDC or c-tsDC.

4. Effects of a-tsDC and c-tsDC on Latency of Cortically-elicited Tibial Nerve Potentials Latency of cortically-elicited tibial nerve potentials was measured before, during, and after a-tsDC and c-tsDC. Only latencies measured at a-tsDC of +2 mA and c-tsDC of −2 mA are presented because no differences were found between latencies at these intensities and those at other intensities that caused significant increases in TS twitches. However, the mean latency was calculated based on measurements at all time points following tsDC. For a-tsDC, Kruskal-Wallis ANOVA showed a significant effect of time (baseline, during, and after stimulation), as shown in FIG. 17A. Post hoc tests revealed that the latency of cortically-elicited tibial nerve potentials was significantly longer during +2 mA stimulation (21.5±0.34 ms) and shorter after termination (17.92±0.21 ms) relative to baseline (19.82±0.17 ms). Similarly, for c-tsDC application, Kruskal-Wallis ANOVA showed a significant effect of time. Post hoc tests revealed that the latency of cortically-elicited tibial nerve potentials was significantly shorter during −2 mA stimulation (17.42±0.22 ms) and longer after termination (23.90±1.19 ms) relative to baseline (20.33±0.19 ms).

Taken together, these data indicate that tsDC affects the excitability of spinal neurons in a way that changes their ability to respond to the motor cortex. Thus, changes in latency may be due to redirection of the intra-spinal pathway to a faster or slower route depending on the number of synapses or simply due to changes in the recruitment pattern of spinal neurons.

5. Paired rCES and tsDC Stimulation

Figure 18A:
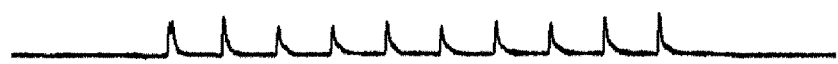
FIGS. 18A-18D illustrate the effect of paired tsDC and repetitive cortical stimulation (rCES) on cortically-elicited TS twitches. Representative recordings of TS twitches before stimulation (baseline), during stimulation, and after stimulation are shown for a-tsDC (+2 mA) paired with rCES in FIGS. 18A and c-tsDC (−2 mA) paired with rCES in FIG. 18B. rCES was adjusted to give the maximal response (~5.5 mA) and was delivered at 1 Hz for 3 min. Both a-tsDC paired with rCES in FIGS. 18C and c-tsDC paired with rCES in FIG. 18D significantly improved cortically-elicited TS twitches compared to baseline. Error bars represent S.E.M. *p<0.001 compared to baseline, Wilcoxon Signed Rank Test
Figure 18A:
Figure 18A:
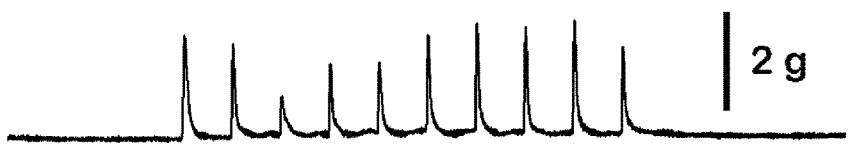
Figure 18B:
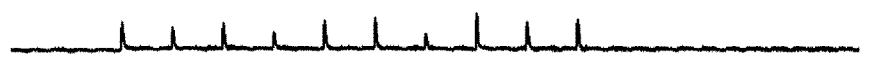
Figure 18B:
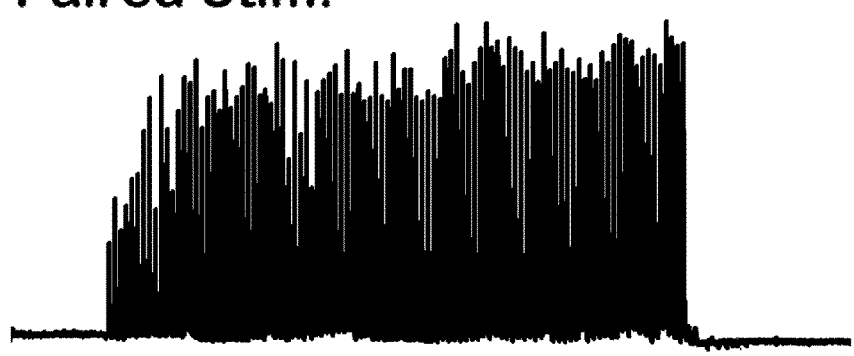
Figure 18B:
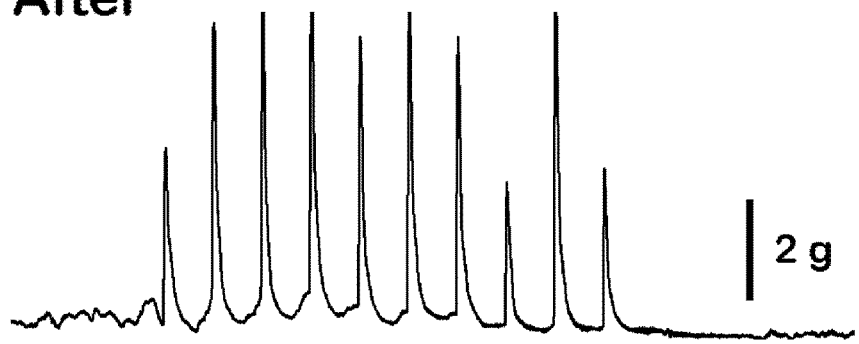
Figure 18C:
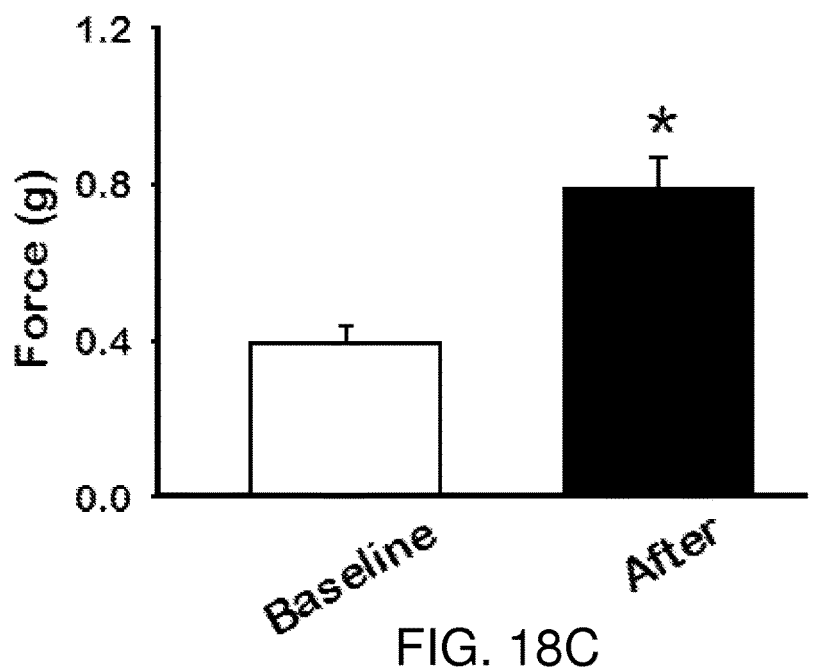
Figure 18D:
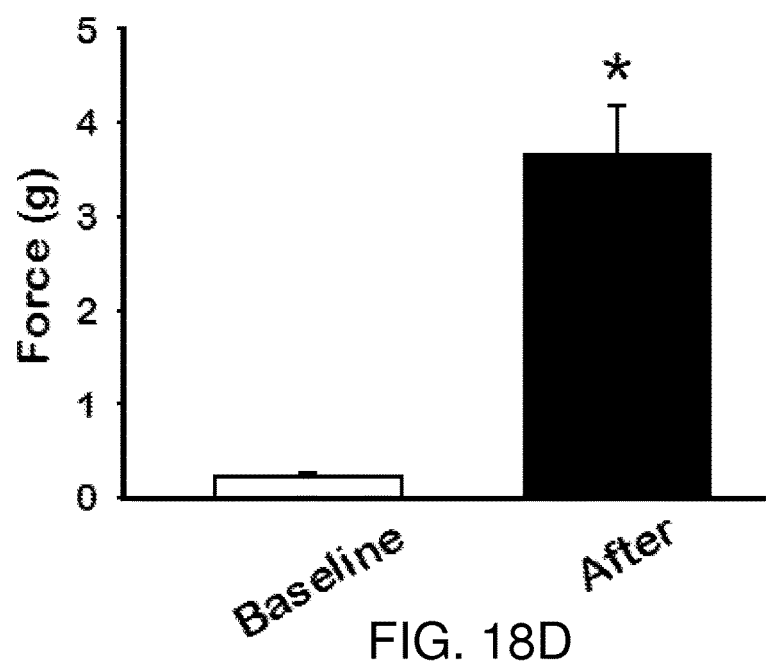

The motor cortex was stimulated for 3 min (180 pulses, 1 Hz, maximal intensity ~5.5 mA) during either a-tsDC (+2 mA) or c-tsDC (−2 mA), as shown in FIGS. 18A and 18B. Paired rCES and a-tsDC was associated with a significant improvement in cortically-elicited TS twitches after termination of stimulation (0.80±0.10 g) compared to baseline (0.39±0.05 g) ($p<0.001$), as shown in FIG. 18C. Notably, paired rCES and c-tsDC showed a similar improvement after termination (3.67±0.51 g) compared to baseline (0.21±0.51 g) ($p<0.001$), as shown in FIG. 18D. Improvement following those two different stimulation paradigms persisted with no notable change immediately, at 5 min and at 20 min after termination. Thus, results presented after termination represent the average of these three time points. The effect of rCES alone was tested in separate group of animals (n=2), and no change was found after termination compared to baseline (t test, $p>0.05$) (data not shown).

A total of four stimulation paradigms used in the current experiment affected cortically-elicited TS contraction: a-tsDC, c-tsDC, a-tsDC with rCES, and c-tsDC with rCES. Kruskal-Wallis ANOVA showed a significant effect of condition (H=66.97, $p<0.001$). Multiple comparisons showed that paired c-tsDC and rCES was more effective than all other paradigms (2287.07±342.49%) ($p<0.05$), especially for reversing the depressive effect seen after c-tsDC (33.66±9.82%). Paired a-tsDC and rCES showed no significant difference (252.88±30.79%) compared to a-tsDC alone (329.18±38.79%) ($p>0.05$). These findings indicate that cortical activity had a strong influence on c-tsDC after-effects, however, it had no influence on a-tsDC after-effects.

Discussion

Histological analysis demonstrated no harmful morphological effects of the tsDC parameters used in the present study. The maximal current density used was 3.75 A/m² for a duration of 3 min, which is much lower than the range typically used in rats and mice as known in the art. In this study, spinal cord stimulation differed from cranial stimulation in three respects: (1) the distance from the electrode surface to the ventral aspect of the spinal cord was ~7 mm, as opposed to the distance to the cranium of ~0.3 mm; (2) bone, muscle and fat tissue was present between the electrode and spinal cord, while only bone was present at the cranium; and (3) the volume of the conductor surrounding the target tissue was much larger in the spinal cord than in the brain, potentially deforming the current and reducing its density.

Both a- and c-tsDC markedly increased the frequency and amplitude of spontaneous tibial nerve activity in an intensity-dependent fashion. Interestingly, a-tsDC was more effective than c-tsDC in increasing firing frequency and recruiting units with larger amplitude. These results are in agreement with data from a-tsDC stimulation of the cerebral cortex, hippocampal slices, and cerebellum. The effects of c-tsDC on neuronal discharges were more complex in three respects. First, c-tsDC only caused significant changes at higher intensities (−2 and −3 mA). Second, c-tsDC did not cause firing of neurons with large spikes, but was observed in some experiments to inhibit firing of large spikes (1 mV), while increasing firing of smaller spikes. Third, as seen in FIG. 14B, c-tsDC evoked rhythmic firing. The c-tsDC-induced increase in firing rate supports previous observations in which negative currents occasionally increased firing rate. See Bindman L. J., Lippold O. C., and Redfearn J. W., The action of brief polarizing currents on the cerebral cortex of the rat (1) during current flow and (2) in the production of long-lasting after-effects, J. Physiol. 172: 369-382 (1964).

During stimulation, a-tsDC depressed cortically-elicited TS twitches, while c-tsDC markedly potentiated twitches. From immediately after termination of tsDC until at least 20 min later, cortically-elicited TS twitches were markedly potentiated after a-tsDC and depressed after c-tsDC. Moreover, while a-tsDC increased the latency of cortically-elicited tibial nerve potentials, c-tsDC decreased this latency. After a-tsDC or c-tsDC stimulation was terminated, the effect on latency was reversed.

Changes in latency were observed despite a steady intensity of cortical stimulation, suggesting that factors underlying these changes are not likely to include the switch from a cortical site of activation to a deeper location (Rothwell et al. 1994). Instead, these factors may include: (1) axonal hyperpolarization (Moore and Westerfield 1983) by c-tsDC or (2) activating preferential spinal circuits that mediate corticomotoneuronal transmission. In rodents, the corticomotoneural pathway has two indirect routes, a faster route mediated via reticulospinal neurons and a slower route mediated via segmental interneurons. The present findings suggest that c-tsDC may shift the pattern of excitability at the spinal cord toward the faster reticulospinal route. Interestingly, pairing a-tsDC with rCES (1 Hz) potentiated cortically-elicited TS twitches, but was not different from a-tsDC alone. Conversely, pairing c-tsDC with rCES potentiated cortically-elicited TS twitches and had the greatest effects of any stimulation condition.

The differences in the effects of a-tsDC and c-tsDC on neuronal activity suggest that the two conditions affect distinctive neuronal types through different mechanisms. The topography of spinal neurons relative to the direction of current determines the current locus and type of effect (i.e., increase or decrease in excitability). As illustrated in FIG. 19, a dorsal cathodal current should depolarize neuronal compartments closer to the electrode and hyperpolarize compartments farther from the electrode. Thus, an interneuron with its dendrites and soma at the ventral aspect of the spinal cord and its axon at the dorsal aspect would have a hyperpolarized dendritic tree and soma and a depolarized axon and nerve terminal. Such a neuron would be less responsive to synaptic activation, but would have a lower threshold to spontaneously fire an axonally-generated action potential. A spinal neuron oriented in the opposite direction would show an opposite response to cathodal stimulation. This argument is supported by the finding that motoneuron responses to dorsolateral and medial funiculus stimulation were facilitated by depolarizing currents in the dendrites and soma, but were not affected by hyperpolarizing currents, which have also been shown to occur in the hippocampus (Bikson 2004). See Delgado-Lezama R., Perrier J. F., and Hounsgaard J., Local facilitation of plateau potentials in dendrites of turtle motoneurones by synaptic activation of metabotropic receptors, J. Physiol. 515 (Pt 1): 203-207 (1999) and Bikson M., Effects of uniform extracellular DC electric fields on excitability in rat hippocampal slices in vitro, J. Physiol. 557: 175-190 (2004).

Presynaptic depolarization has been shown to decrease presynaptic nerve action potentials and EPSPs. See Hubbard J. I. and Willis W. D., The effects of depolarization of motor nerve terminals upon the release of transmitter by nerve impulses, J. Physiol. 194: 381-405 (1968); Hubbard J. I. and Willis W. D., Reduction of transmitter output by depolarization, Nature 193: 1294-1295 (1962). The decrease in the presynaptic nerve action potentials and EPSPs may play a role in depressing cortically-elicited TS twitches during a-tsDC. In addition, hyperpolarization of the soma and dendrites could depress motoneuron responses to cortical stimulation during a-tsDC. Alternative explanations could include: (1) increased numbers of refractory motor neurons due to increased spontaneous firing, or (2) preferential activation of the spinal or supraspinal inhibitory pathway.

Rhythmic activity was observed during c-tsDC but not a-tsDC, indicating that c-tsDC may have a depressive effect on spinal inhibitory interneurons. Such interneurons might be inhibited because of their topography relative to the applied electrical field. C-tsDC might hyperpolarize both excitatory and inhibitory spinal interneurons. If it is assumed that inhibitory and excitatory spinal interneurons contain different membrane channels (e.g., fewer low-voltage-activated T-type calcium channels and hyperpolarization-activated cation channels in inhibitory interneurons), then hyperpolarization would silence inhibitory interneurons, hence disinhibiting the excitatory interneurons. In contrast, in spinal rhythmogenic neurons, hyperpolarizing tsDC might activate the hyperpolarization-activated, nonselective cation current (Ih). In combination with T-type Ca channels, Ih should gradually depolarize the cell membrane to reach the threshold for an action potential, which could be another mechanism mediating c-tsDC-induced potentiation of cortically-elicited TS twitches.

Moreover, cathodal stimulation has been shown to increase the excitability of axons aligned perpendicular to the direction of current. See Ardolino G., Bossi B., Barbieri S., and Priori A., Non-synaptic mechanisms underlie the after-effects of cathodal transcutaneous direct current stimulation of the human brain, J. Physiol. 568: 653-663 (2005). Therefore, in the present study, the corticospinal tract, which passes below the cathodal electrode, would be expected to increase axonal excitability and hence spinal output. Conversely, the dendrites and soma of motoneurons would be hyperpolarized and axons would be depolarized in response to a-tsDC stimulation. Axonal depolarization at locations that affect voltage-sensitive membrane conductances could increase the firing rate and amplitude of spontaneous activity during a-tsDC.

In the spinal cord, L-type $Ca^{+2}$ channels present in motoneuron dendrites mediate the facilitatory action of depolarizing currents. However, the exact cellular mechanisms mediating DC stimulation after-effects are not clear. Notably, mechanisms mediating the depressive after-effects of cathodal DC stimulation are completely unknown. We suggest that the pattern of c-tsDC-induced polarization (e.g., pre-synaptic hyperpolarization and post-synaptic depolarization) might activate depression-mediating mechanisms, such as retrograde signaling by endocannabinoids that selectively depresses inhibitory pre-synaptic terminals.

Eighth Experiment (Employing aCENS)

In the seventh experiment, tsDC stimulation was applied to the same nine-month-old baby girl with quadriplegic paralysis as described in the fifth experiment in the fall of 2010. This child had been completely paralyzed without movement in the head, the neck, the trunk, and the upper and lower extremities. While her upper extremities responded to the dCMS treatment, her lower extremities did not respond to the pulsing electrical stimulation signals.

Over a course of three weeks, the child was treated in four tsMC treatment sessions that lasted about 15 minutes each. Two first electrodes were connected to her left motor cortex and her right motor cortex. Multiple second electrodes were connected to her right fibular nerve ending, her left fibular nerve ending, the belly of her right calf muscle, the belly of her left calf muscle, her right sole, and her left sole. A third electrode was placed on her spine between the T9 and T12 vertebrae. The same electrical stimulation signal including bipolar electrical pulses with a duration of 400 microseconds as illustrated in FIG. 24 was commonly applied to the two first electrodes, the six second electrodes, and to the third electrode at the frequency of 1 Hz. The amplitude of the same electrical stimulation signal was selected at a signal strength that initiated twitches in her lower extremities.

After treatment, her muscle tone in her lower distal muscles increased, and she was able to sit with hand support. She was able to move her toes and her lower extremities.

While the invention has been described in terms of specific embodiments, it is evident in view of the foregoing description that numerous alternatives, modifications and variations will be apparent to those skilled in the art. Accordingly, the invention is intended to encompass all such alternatives, modifications and variations which fall within the scope and spirit of the invention and the following claims.

What is claimed is:

1. A neural stimulation system for improving neural communication between a cognitive area and a target area of a vertebrate being, said neural stimulation system being adapted to stimulate cortical and target areas coupled by neuronal connections defining a neural pathway of the being, said system comprising:
   a) a first stimulation signal source, said first signal source configured to deliver a first pulsed DC stimulation signal having a first set of pulses to stimulate said cognitive area on said neural pathway, said first signal source being further configured to induce a first pulsed handshake signal on said neural pathway associated with said cognitive area;
   b) a second stimulation signal source, said second signal source configured to deliver a second pulsed DC stimulation signal having a second set of pulses to stimulate said target area on said neural pathway, said second signal source also being configured to induce a second pulsed handshake signal on said neural pathway associated with said target area;
   c) a charging signal source, said charging signal source configured to supply a constant DC charging signal to said neural pathway, the neural pathway including a spinal neural communication site of the being; and
   d) a synchronizing component, said synchronizing component having a computer part and configured: to initiate application of said charging signal to charge-enhance performance of the neural pathway including of the spinal neural communication trigger site, and to synchronize contemporaneous convergence of the first and second pulsed handshake signals at the spinal neural communication trigger site.

2. The system of claim 1 wherein said first and second stimulation signal sources respectively comprise a first electric pulse generator and a second electric pulse generator and said charging signal source comprises a charging signal generator.

3. The system of claim 2 wherein said synchronizing component comprises a multi-function computer having at least one program that allows user-selectable setting of treatment parameters, said computer including a digital interface device and a display screen.

4. The system of claim 1 wherein at least one of said first stimulation signal sources provides said first set of pulses at a frequency that does not exceed 100 Hz and having a duration from 40 microseconds to 10 milliseconds.

5. The system of claim 1 wherein said charging signal source is configured to apply a positive signal at a constant level selected between 1 and 2.5 mA.

6. The system of claim 1 wherein said charging signal source is configured to apply a negative signal at a constant level selected between −1 and −3 mA.

7. The system of claim 1 wherein said charging signal source is configured to apply a charging signal at a level selected from the set of: at or below 30 mA to 5 mA, at or below 20 mA to 10 mA, and at or below 2.5 mA to −3 mA.

8. The system of claim 1 wherein said charging signal source is configured to apply an modal tsDC charging signal between 1 and 2.5 mA.

9. The system of claim 1 wherein said charging signal source is configured to apply a cathodal tsDC charging signal between −1 and −3 mA.

10. The system of claim 7 wherein said charging signal source is configured to apply a constant charging signal at a milliamp level.

11. The system of claim 1 wherein said synchronizing component is configured to initiate application of said charging signal to charge-enhance performance of the neural pathway including of the spinal neural communication trigger site, a location of the spinal neural communication trigger site being selected from one of: between the C5 and T1 vertebrae to innervate an upper extremity of the being, and between the T9 and T12 vertebrae to innervate a lower extremity of the being.

12. The system of claim 1, wherein at least two of said signal sources share a common housing and are coupled to said synchronizing component, wherein at least one of said signal sources is configured to issue a stimulation signal having electrical pulses while said constant DC charging signal is applied to said neural pathway.

13. The system of claim 12, wherein several of said signal sources are housed together, said several signal sources being coupled to said synchronizing components for achieving one of synchronous or asynchronous stimulation of said spinal neural communication trigger site.

14. The system of claim 12, wherein said first signal source and second signal source provide respectively a first set of pulsed signals and a second set of pulsed signals, wherein said charging signal source provides a constant negative DC charging signal to be applied to charge said spinal neural communication trigger site contemporaneously with overlap of said pulsed signals at said spinal neural communication trigger site.

15. The system of claim 13, further comprising said housing presenting pairs of outputs for connection to electrodes, wherein one of said pairs supplies one of said first or second stimulation signals and another of said pairs supplies said charging signal.

16. The system of claim 2, wherein said housing further comprises a structure for a mounting a synchronizing computer component coupled to a plurality of said signal sources.

17. The system of claim 2, wherein one of said signal sources provides said continuous charging signal as a negative direct current.

18. The system of claim 1, wherein said first and second sources are selected from the set including electrical signal, sonic signal, ultrasonic signal, magnetic signal, light signal, thermal signal, cryogenic signal, vibrational signal, pressure signal, suction signal.

19. The system of claim 16, further comprising a signal type selector for selecting characteristics of said first and second stimulation signals according to stored user-selectable treatment parameters.

20. The system of claim 16, further comprising a signal type selector for independently selecting said first and said second pulsed signal as derived from the group including magnetic, sonic, vibrational, and electric signal sources.

21. The system of claim 2, wherein said first and said second pulsed handshake signals are each adjusted in shape, magnitude, and polarity.

22. The system of claim 1 wherein said neural stimulation system is adapted to stimulate cognitive and target areas, the target area being neuronally connected to said neural pathway.

23. The system of claim 1 wherein said neural stimulation system is adapted to stimulate cognitive and target areas, the target area being a neuromuscular body part of the being.

24. The system of claim 23 wherein said neural stimulation system is adapted to stimulate cognitive and target areas, the cortical area being a motor cortex of the being.

25. The system of claim 23 wherein the synchronizing component is configured to synchronize contemporaneous convergence of the first and second pulsed handshake signals at the spinal neural communication trigger site, the spinal neural communication trigger site being associated with neural control of said neuromuscular body part from said motor cortex.

\* \* \* \* \*

UNITED STATES PATENT AND TRADEMARK OFFICE
CERTIFICATE OF CORRECTION

PATENT NO. : 9,821,157 B2
APPLICATION NO. : 14/157689
DATED : November 21, 2017
INVENTOR(S) : Zaghloul Ahmed et al.

Page 1 of 1

It is certified that error appears in the above-identified patent and that said Letters Patent is hereby corrected as shown below:

In the Claims

In Column 86, Line 32 (Claim 1), "cognitive" should read -- cortical --
In Column 86, Line 38 (Claim 1), "pulsed DC stimulation" should read -- pulsed stimulation --
In Column 86, Lines 45-46 (Claim 1), "pulsed DC stimulation" should read -- pulsed stimulation --
In Column 86, Line 56 (Claim 1), "configured: to" should read -- configured to --
In Column 88, Line 35 (Claim 22), "cognitive" should read -- cortical --
In Column 88, Line 39 (Claim 23), "cognitive" should read -- cortical --
In Column 88, Line 42 (Claim 24), "cognitive" should read -- cortical --

Signed and Sealed this
Fifteenth Day of May, 2018

Andrei Iancu
*Director of the United States Patent and Trademark Office*